US012708316B2

(12) United States Patent
Ruppersberg et al.

(10) Patent No.: US 12,708,316 B2
(45) Date of Patent: Aug. 18, 2026

(54) SYSTEMS, DEVICES, COMPONENTS AND METHODS FOR HIGH RESOLUTION ELECTROGRAPHIC FLOW (EGF) MAPPING AND ANALYSIS

(71) Applicant: Cortex, Inc., Menlo Park, CA (US)

(72) Inventors: Peter Ruppersberg, Blonay (CH); Philip Haeusser, Munich (DE); Melissa Huang Szu-Min Kong, Austin, TX (US); Josef Vincent Koblish, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 159 days.

(21) Appl. No.: 18/427,790

(22) Filed: Jan. 30, 2024

(65) Prior Publication Data

US 2025/0040860 A1 Feb. 6, 2025

Related U.S. Application Data

(60) Provisional application No. 63/442,421, filed on Jan. 31, 2023.

(51) Int. Cl.
*A61B 5/00* (2006.01)
*A61B 5/282* (2021.01)
(Continued)

(52) U.S. Cl.
CPC .............. *A61B 5/367* (2021.01); *A61B 5/287* (2021.01); *A61B 5/343* (2021.01); *A61B 5/352* (2021.01)

(58) Field of Classification Search
CPC ......... A61B 5/367; A61B 5/287; A61B 5/343; A61B 5/352; A61B 2562/0209;
(Continued)

(56) References Cited

U.S. PATENT DOCUMENTS

2017/0065198 A1* 3/2017 Ruppersberg .......... A61B 5/341
2022/0400951 A1* 12/2022 Haeusser ............. A61B 5/6852

FOREIGN PATENT DOCUMENTS

EP 4029449 A1 7/2022
WO WO 2019/063861 A1 4/2019
WO WO 2019/144103 A1 7/2019

OTHER PUBLICATIONS

EESR EP24154786 EP4410209, Jun. 27, 2024, Ablacon Inc.

(Continued)

*Primary Examiner* — Carl H Layno
*Assistant Examiner* — Anh-Khoa N Dinh
(74) *Attorney, Agent, or Firm* — Nelson Mullins Riley & Scarborough LLP

(57) ABSTRACT

The disclosures described are various examples and embodiments of systems, devices, components and methods configured to provide enhanced resolution electrographic flow (EGF) spatial mapes of a patient's heart, and subsequently to detect at least one location or type or at lease one source, rotational phenomenon, or slow electrical conduction zone or area associated with at least one cardiac rhythm disorder within such maps. Data acquired using intracardiac electrodes and/or body surface electrodes are used in conjunction with EGF techniques to generate an enhanced resolution map corresponding to a spatial map. The enhanced resolution map is configured to reveal on a monitor or display to a user or the at least one location or type of the at least one source, rotational phenomenon, or slow electrical conduction zone or area associated with at least one cardiac rhythm disorder.

27 Claims, 56 Drawing Sheets
(35 of 56 Drawing Sheet(s) Filed in Color)

(51) Int. Cl.
*A61B 5/287* (2021.01)
*A61B 5/343* (2021.01)
*A61B 5/352* (2021.01)
*A61B 5/367* (2021.01)

(58) Field of Classification Search
CPC . A61B 2562/046; A61B 5/0022; A61B 5/725; A61B 5/0044; A61B 5/282; A61B 5/361; A61B 5/4836; A61B 5/6823; A61B 5/6858; A61B 5/6869; A61B 5/7267; A61B 5/7275; A61B 5/743; A61B 18/1492; A61N 1/365; G16H 20/30; G16H 30/40; G16H 40/63
See application file for complete search history.

(56) References Cited

OTHER PUBLICATIONS

G. Rios-Munoz et al., "Real-Time Rotational Activity Detection in Atrial Fibrillation," Frontiers in Physiology, vol. 9, Art. 208, Mar. 19, 2018, pp. 1-17, Lausanne, Switzerland.
B. Bellmann et al., "Identification of active atrial fibrillation sources . . . ," May 9, 2018, Clin. Res. Cardiology., vol. 107, No. 11, 1021-1032, Springer, Berlin, Germany.

* cited by examiner

ABLAMAP IMAGE
SINGLE ACTIVE ROTOR
(64 ELECTRODES)

Example of Potential Distribution During the Sinus Rhythm P-Wave

SYSTEMS, DEVICES, COMPONENTS AND METHODS FOR HIGH RESOLUTION ELECTROGRAPHIC FLOW (EGF) MAPPING AND ANALYSIS

RELATED APPLICATIONS

This application is related to, and claims priority and other benefits from, U.S. Provisional Patent Application Ser. No. 63/442,421 entitled "Systems, Devices, Components and Methods for High Resolution Electrographic Flow (EGF) Mapping and Analysis" to Ruppersberg et al. filed Jan. 31, 2023 (hereafter "the '421 patent application"). The entirety of the '421 patent application is hereby incorporated by reference herein.

FIELD OF THE INVENTION

Various embodiments described and disclosed herein relate to the field of medicine generally, and more particularly to detecting, diagnosing, predicting and treating cardiac rhythm disorders such as atrial fibrillation in a patient's heart.

BACKGROUND

Persistent atrial fibrillation (AF) is a prevalent human cardiac arrhythmia that can lead to severe illness, and is assumed to be caused by structural changes in atrial tissue, which can manifest themselves as multiwavelet re-entry and/or stable rotor mechanisms (see, e.g., De Groot N. M. S. et al., "Electropathological Substrate of Longstanding Persistent Atrial Fibrillation in Patients with Structural Heart Disease Epicardial Breakthrough," Circulation, 2010, 3: 1674-1682). In addition to pharmaceutical treatments, catheter-based atrial ablation is a commonly used therapy for AF. AF is characterized by chaotic irregular patterns of excitation-wave propagation in the atria which lead to an absolute arrhythmic heartbeat.

Radiofrequency (RF) ablation targeting host drivers of AF is generally accepted as the best therapeutic approach. RF ablation success rates in treating AF cases are currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

In many patients, circular ablation of the pulmonary veins (pulmonary vein isolation or PVI) is effective in achieving freedom from AF. However, in about 40% of patients, it is necessary to ablate additional targets in the atrial wall that are thought to represent ectopic sources of excitation which compete with the sinus node (SN), the pacemaker of normal sinus rhythm (NSR). Ablation of putative is sources has been shown to improve therapeutic outcome and often leads to acute termination of AF to NSR or sometimes atrial flutter (AFL) a more regular arrhythmia which can be treated by another systematic ablation strategy.

To identify and locate ectopic sources of excitation it is necessary to analyze the electrical behavior of the atrial surface, i.e.; the traveling of excitation waves, also designated as the electrographic flow (EGF).

What is needed are improved means and methods of acquiring and processing intracardiac and/or body surface electrogram signals that reliably and accurately yield the precise locations and sources of cardiac rhythm disorders in a patient's heart. Doing so would enable cardiac ablation procedures to be carried out with greater locational precision, and would result in higher rates of success in treating cardiac rhythm disorders such as AF.

SUMMARY

In one embodiment, there is provided a system configured to detecting at least one location of: (a) at least one intracardiac source or rotational phenomenon; and (b) at least one intracardiac zone or area of slow electrical conduction velocity, such source, phenomenon, zone or area being associated with at least one cardiac rhythm disorder in a patient's heart, the system comprising: (a) at least one computing device; (b) at least one data acquisition device operably connected to the at least one computing device or configured to provide as outputs therefrom at least one of intracardiac electrophysiological EP mapping signals and/or body surface electrophysiological EP mapping signals (EP mapping signals); (c) a display or monitor operably connected to the at least one computing device and configured to visually display to the user one or more maps generated by the at least one computing device; wherein the computing device comprises at least one non-transitory computer readable medium configured to store instructions executable by at least one processor to determine the at least one location of the at least one source, rotational phenomenon, and/or zone of slow electrical conduction, associated with the at least one cardiac rhythm disorder in the patient's heart, the computing device being configured to: (i) receive the EP mapping signals from at least one of a plurality of intracardiac electrodes located inside the patient's heart and/or the body surface electrodes located on the surface of the patient's body (electrodes), the electrodes having spatial 2D and/or 3D positions on or in the patient's body associated therewith; (ii) preprocess the EP mapping signals; (iii) analyzing the preprocessed EP mapping signals and determining reconstruction constraint parameters to apply thereto; (iii) apply the reconstruction constraint parameters to the EP mapping data and generating, using one or more correlation matrices, reconstructed EP mapping signals having spatial positions associated therewith and located between, or not at the same locations as, the spatial positions of the electrodes; (iv) assign or relate positional data corresponding to spatial positions of: (a) the electrodes and their associated EP mapping signals, and (b) the reconstructed EP mapping signals; (v) generate at least one spatial map of the electrode positions and the positions of the reconstructed EP mapping signals; (vi) for each or selected discrete times over which the EP mapping signals and the reconstructed EP mapping signals are being processed, process the EP mapping signals and the reconstructed EP mapping signals to generate a plurality of surfaces or data grids, each such surface or data grid corresponding at least partially to the at least one spatial map, at least one surface or data grid being generated for each such time, and (v) using a multi-frame Horn-Schunck algorithm to process the plurality of surfaces or data grids through time to generate at least one enhanced resolution map corresponding at least partially to the spatial map, the at least one enhanced resolution map being configured to reveal the at least one location of the at least one source or rotational phenomenon, and/or at least one zone or area of slow electrical conduction velocity, associated with the at least one cardiac rhythm disorder, the at least one enhanced resolution map being shown to the user on the display or monitor.

In some embodiments, such a system may further comprise one or more of: (a) wherein analyzing and determining the constraint reconstruction parameters to apply to the EP mapping signals is further based upon the shapes and velocities of the EP mapping signals; (b) wherein preprocessing of the EP mapping signals comprises generating at least one histogram of all R-peak intervals and determining the width(s) thereof; (c) subtracting averaged R-peak traces from all traces of the EP mapping signals; (d) detecting F-wave peaks in the EP mapping signals; (e) determining average intervals between R-peaks and F-waves before determining constraint reconstruction parameters; (f) wherein the intracardiac electrodes are mounted on or form a portion of a basket catheter; (g) wherein the basket catheter has between 32 and 64 electrodes; (h) wherein the surfaces or data grids are generated by the computing device using Green's function; (i) wherein the map generated by the computing device is configured to reveal a location in the patient's heart of one or more of: (1) an active rotor; (2) a passive rotor; (3) a breakthrough point, (4) a focal point, and (5) a slow electrical conduction velocity zone or area; (j) wherein the reconstructed EP mapping signals are generated using one or more of the following image reconstruction methods or techniques, alone or in combination: (1) spatio-temporal constraint reconstruction (STCR) methods or techniques; (2) Bayesian or extended Bayesian back-filtered projection methods or techniques; (3) machine learning methods or techniques; (4) deep learning or cascaded deep learning methods or techniques; (5) domain-transform manifold learning methods or techniques; (6) neural network methods or techniques; (7) convolutional neural network methods or techniques; (8) deep generative adversarial network methods or techniques; (9) dual domain cascading U-net methods or techniques; and/or (10) de-aliasing network methods or techniques; (k) wherein the at least one enhanced resolution map represents between 64 and 1,024 combined spatial positions of the electrodes and the reconstructed EP mapping signals; and (I) wherein the enhanced resolution map comprises or displays optimized intensity points (EDFs).

In some embodiments, there is provided a method of detecting at least one location of at least one intracardiac source or rotational phenomenon and/or at least one intracardiac zone or area of slow electrical conduction velocity, such source, phenomenon, zone or area being associated with at least one cardiac rhythm disorder in a patient's heart, the system comprising at least one computing device, at least one data acquisition device operably connected to the at least one computing device or configured to provide as outputs therefrom at least one of intracardiac electrophysiological EP mapping signals and/or body surface electrophysiological EP mapping signals (EP mapping signals), a display or monitor operably connected to the at least one computing device and configured to visually display to the user one or more maps generated by the at least one computing device, wherein the computing device comprises at least one non-transitory computer readable medium configured to store instructions executable by at least one processor to determine the at least one location of the at least one source, rotational phenomenon, and/or zone of slow electrical conduction, associated with the at least one cardiac rhythm disorder in the patient's heart, the computing device being configured to: (i) receive the EP mapping signals from at least one of a plurality of intracardiac electrodes located inside the patient's heart and/or the body surface electrodes located on the surface of the patient's body (electrodes), the electrodes having spatial 2D and/or 3D positions on or in the patient's body associated therewith; (ii) preprocess the EP mapping signals: (iii) analyze the preprocessed EP mapping signals and determining reconstruction constraint parameters to apply thereto; (iii) apply the reconstruction constraint parameters to the EP mapping data and generating, using one or more correlation matrices, reconstructed EP mapping signals having spatial positions associated therewith and located between, or not at the same locations as, the spatial positions of the electrodes; (iv) assign or relate positional data corresponding to spatial positions of: (a) the electrodes and their associated EP mapping signals, and (b) the reconstructed EP mapping signals; (v) generate at least one spatial map of the electrode positions and the positions of the reconstructed EP mapping signals; (vi) for each or selected discrete times over which the EP mapping signals and the reconstructed EP mapping signals are being processed, process the EP mapping signals and the reconstructed EP mapping signals to generate a plurality of surfaces or data grids, each such surface or data grid corresponding at least partially to the at least one spatial map, at least one surface or data grid being generated for each such time, and (v) using a multi-frame Horn-Schunck algorithm to process the plurality of surfaces or data grids through time to generate at least one enhanced resolution map corresponding at least partially to the spatial map, the at least one enhanced resolution map being configured to reveal the at least one location of the at least one source or rotational phenomenon, and/or at least one zone or area of slow electrical conduction velocity, associated with the at least one cardiac rhythm disorder, the at least one enhanced resolution map being shown to the user on the display or monitor, the method comprising: (a) acquiring, using the data acquisition device, the EP mapping signals; (b) using the computing device, assigning positions or identifiers for the electrodes and the reconstructed EP mapping signals; (d) using the computing device and the assigned positions or identifiers, providing or generating a spatial map of the intracardiac electrode and reconstructed EP mapping signal positions; (e) using the computing device, for each or selected discrete times over which the EP mapping signals are being processed, processing the EP mapping signals to generate a plurality of surfaces or data grids corresponding at least partially to the spatial map, one surface or data grid being generated for each such time, and (f) using the computing device to process the plurality of surfaces or data grids through time to generate an enhanced resolution map corresponding at least partially to the spatial map, the enhanced resolution map being configured to reveal on the monitor or display to a user the at least one location of the at least one source, phenomenon, zone or area associated with the at least one cardiac rhythm disorder.

Such a method may further comprise one or more of: (a) using at least one of the computing device and the data acquisition device, at least one of conditioning, filtering, normalizing and adjusting the amplitudes of at least one of the acquired EP mapping signals; (b) generating the surfaces or data grids using Green's function; (c) wherein analyzing and determining the constraint reconstruction parameters to apply to the EP mapping signals is further based upon the shapes and velocities of the EP mapping signals; (d) wherein preprocessing of the EP mapping signals comprises generating at least one histogram of all R-peak intervals and determining the width(s) thereof; (e) subtracting averaged R-peak traces from all traces of the EP mapping signals; (f) detecting F-wave peaks in the EP mapping signals; (g) determining average intervals between R-peaks and F-waves before determining constraint reconstruction parameters; (h) wherein the intracardiac electrodes are mounted on or form a portion of a basket catheter; (i) wherein the basket catheter has between 32 and 64 electrodes; (j) wherein the enhanced resolution map generated by the computing device is configured to reveal a location in the patient's heart of one or more of: (1) an active rotor; (2) a passive rotor; (3) a breakthrough point, (4) a focal point, and (5) a slow electrical conduction velocity zone or area; (k) wherein the reconstructed EP mapping signals are generated using one or more of the following image reconstruction methods or techniques, alone or in combination: (1) spatio-temporal constraint reconstruction (STCR) methods or techniques; (2) Bayesian or extended Bayesian back-filtered projection methods or techniques; (3) machine learning methods or techniques; (4) deep learning or cascaded deep learning methods or techniques; (5) domain-transform manifold learning methods or techniques; (6) neural network methods or techniques; (7) convolutional neural network methods or techniques; (8) deep generative adversarial network methods or techniques; (9) dual domain cascading U-net methods or techniques; and/or (10) de-aliasing network methods or techniques; (1) wherein the at least one enhanced resolution map represents between 64 and 1,024 combined spatial positions of the electrodes and the reconstructed EP mapping signals, and (m) wherein the enhanced resolution map comprises or displays optimized intensity points (EDFs).

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

FIG. 30 shows an STCR-enhanced EGF map from the same procedure as in FIG. 29, but where intensive pacing has converted the rhythm to AT;

FIG. 36 shows unipolar recordings from the RA of a patient exhibiting AF, where excitation wave propagation from a focal source in the posterior wall is displayed.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for diagnosing and treating cardiac rhythm disorders in a patient's heart using electrophysiological mapping or electrographic flow (EGF) techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Various embodiments of EGF techniques, methods, systems, devices, and components are described and disclosed herein, which involve the acquisition of intra-cardiac and/or body surface electrograms, and the subsequent processing and analysis of such electrograms to reveal the locations of sources of cardiac rhythm disorders in a patient's heart, such as rotors and sources that cause or contribute to AF. That is, many of the various techniques, methods, systems, devices, and components described and disclosed herein may be referred to collectively as pertaining to "EGF."

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
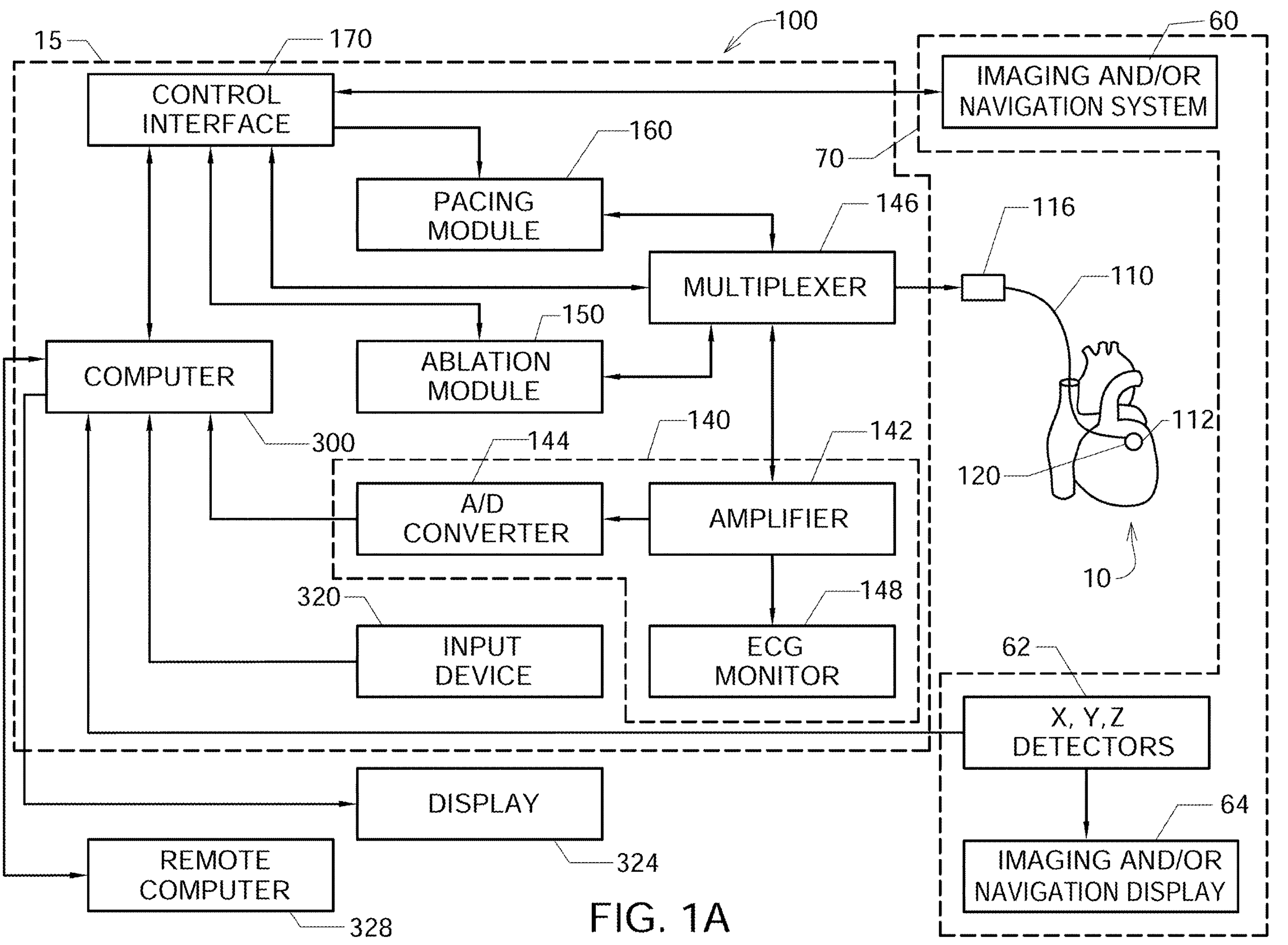
FIG. 1A shows one embodiment of a combined cardiac electrophysiological mapping (EP), pacing and ablation system 100.

Referring now to FIG. 1A, there is illustrated one embodiment of a combined cardiac electrophysiological mapping (EP), pacing and ablation system 100. Note that in some embodiments system 100 may not include ablation module 150 and/or pacing module 160. Among other things, the embodiment of system 100 shown in FIG. 1A is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1A comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, is control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Instead of being operably connected (e.g., through Bluetooth signals, a LAN or WAN network, or through the cloud), or directly connected, to computing device 300, data acquisition device 140 may be configured to provide as outputs therefrom saved or stored body surface electrogram signals, which can be, by way of example, saved or stored on a hard drive, in a memory, on a USB stick, or other suitable storage device, and where the saved or stored body surface electrogram signals are later or subsequently provided as inputs to computing device 300 for processing and analysis.

Computer or computing device 300 may be configured to receive operator inputs from an input device 320 such as a keyboard, mouse and/or control panel. Outputs from computer 300 may be displayed on display or monitor 324 or other output devices (not shown in FIG. 1A). Computer 300 may also be operably connected to a remote computer or analytic database or server 328. At least each of components, devices, modules and systems 60, 110, 140, 146, 148, 150, 170, 300, 324 and 328 may be operably connected to other components or devices by 11 wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes, probes and/or sensors A1 through H8 arranged in an 8×8 grid that are included in electrode mapping assembly 120, which is configured for insertion into the patient's heart through the patient's blood is vessels and/or veins. Other numbers, arrangements, configurations and types of electrodes in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140. In still further embodiments, multiplexer 146 is optional or not provided at all, and data acquisition device 140, ablation module 150, and/or pacing module 160 are employed separately and/or operate independently from one another. In addition, in some embodiments computing device 300 may be combined or integrated with one or more of data acquisition device 140, ablation module 150, and/or pacing module 160.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to move interactively and quickly the electrodes of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magnetocardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1A, EP mapping system or data acquisition is device 140 is configured to condition the analog electrogram signals delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate 11 from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1A, and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1A). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1A). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1A). One embodiment of a pacing module is disclosed in M. E. Josephson et al., in "VENTRICULAR ENDOCARDIAL PACING 11, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1A, system 100 also comprises a physical imaging and/or navigation system 70. Physical imaging and/or navigation device 60 included in system 70 may be, by way of example, a 2- or 3-axis is fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments is described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as processes, methods, data processing systems, and/or computer methods. Accordingly, these portions of the devices and methods described herein may take the form of a hardware embodiment, a software embodiment, or an embodiment combining software and hardware, such as shown and described with respect to computer system 300 illustrated in FIG. 1B. Furthermore, portions of the devices and methods described herein may be a process or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, processes, and systems. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 18:
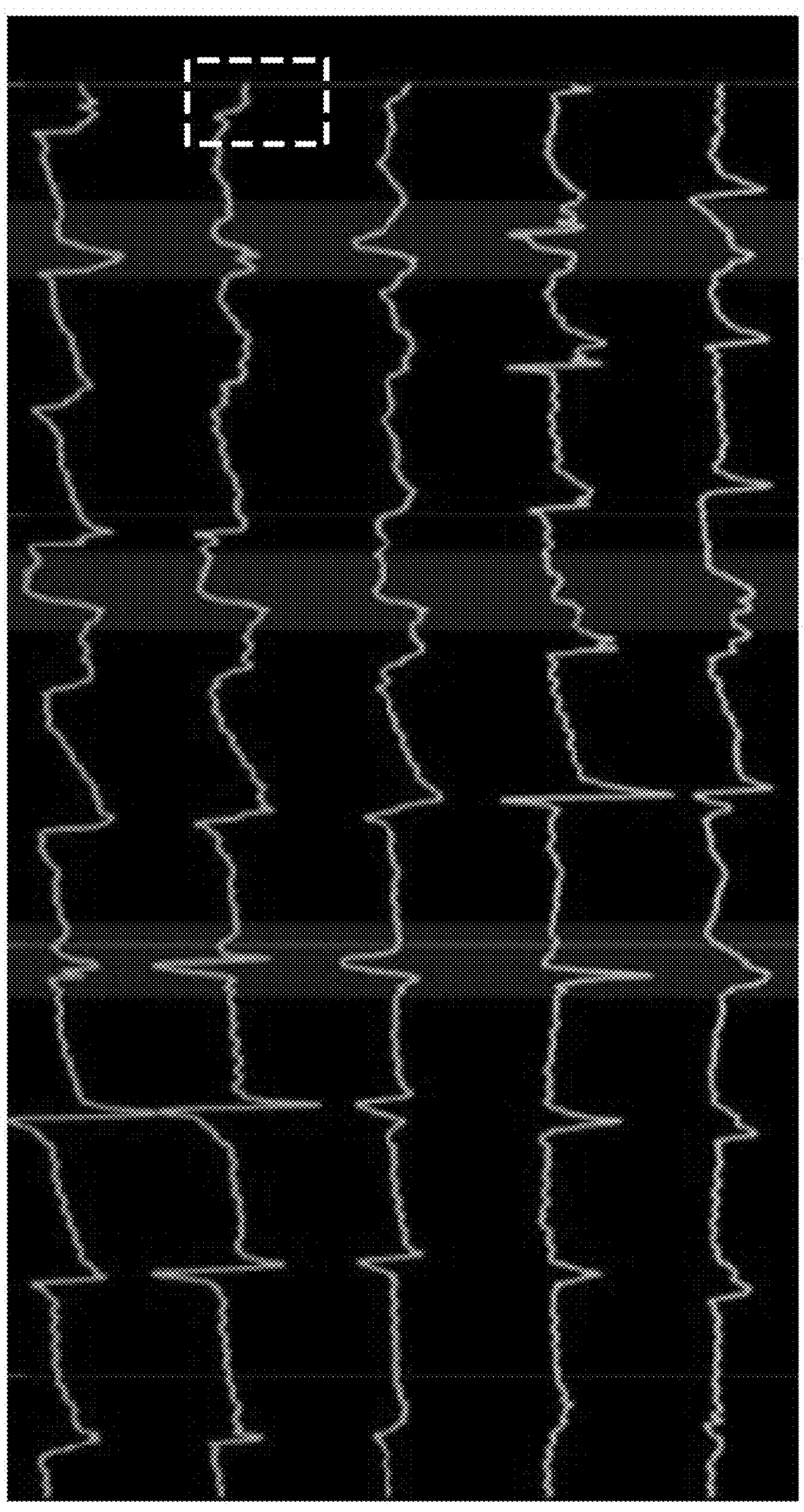
FIG. 18 shows unipolar electrograms recorded from electrodes of a basket catheter.

In this regard, FIG. 18 illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate is devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, is other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein with respect to FIGS. 1-10F.

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
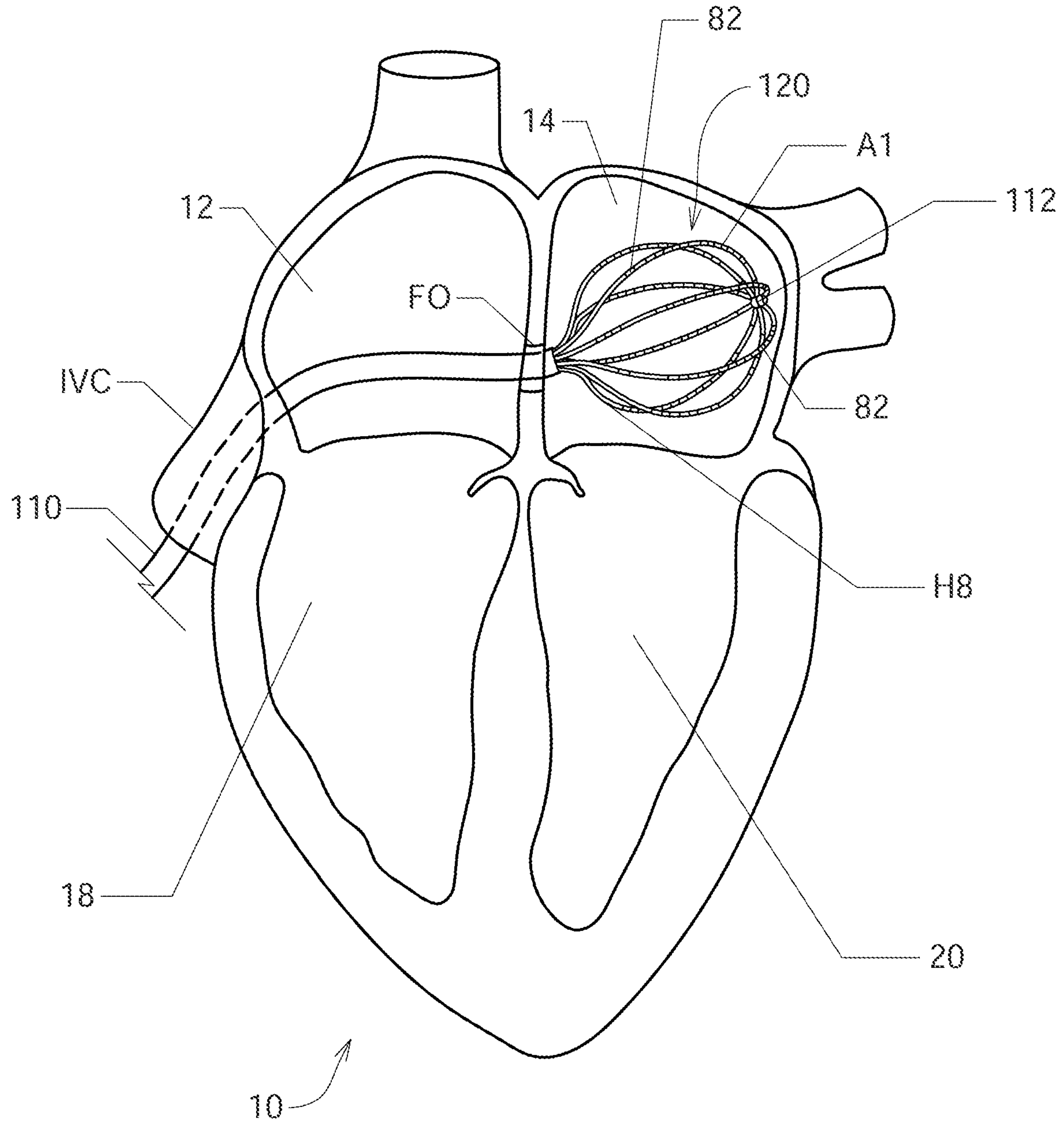
FIG. 2 shows an illustrative view of one embodiment of a distal portion of catheter 110 inside a patient's left atrium 14.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalen ("IVC" and "FO" in FIG. 2), and in one embodiment is configured to obtain electrogram signals from left atrium 12 via an 8×8 array of electrodes A1 through H8, which as shown comprises individual electrodes 82. Mapping electrode assembly and catheter 110 may also be positioned within the patient's right atrium 12, left ventricle 18 and right ventricle 20.

Figure 3:
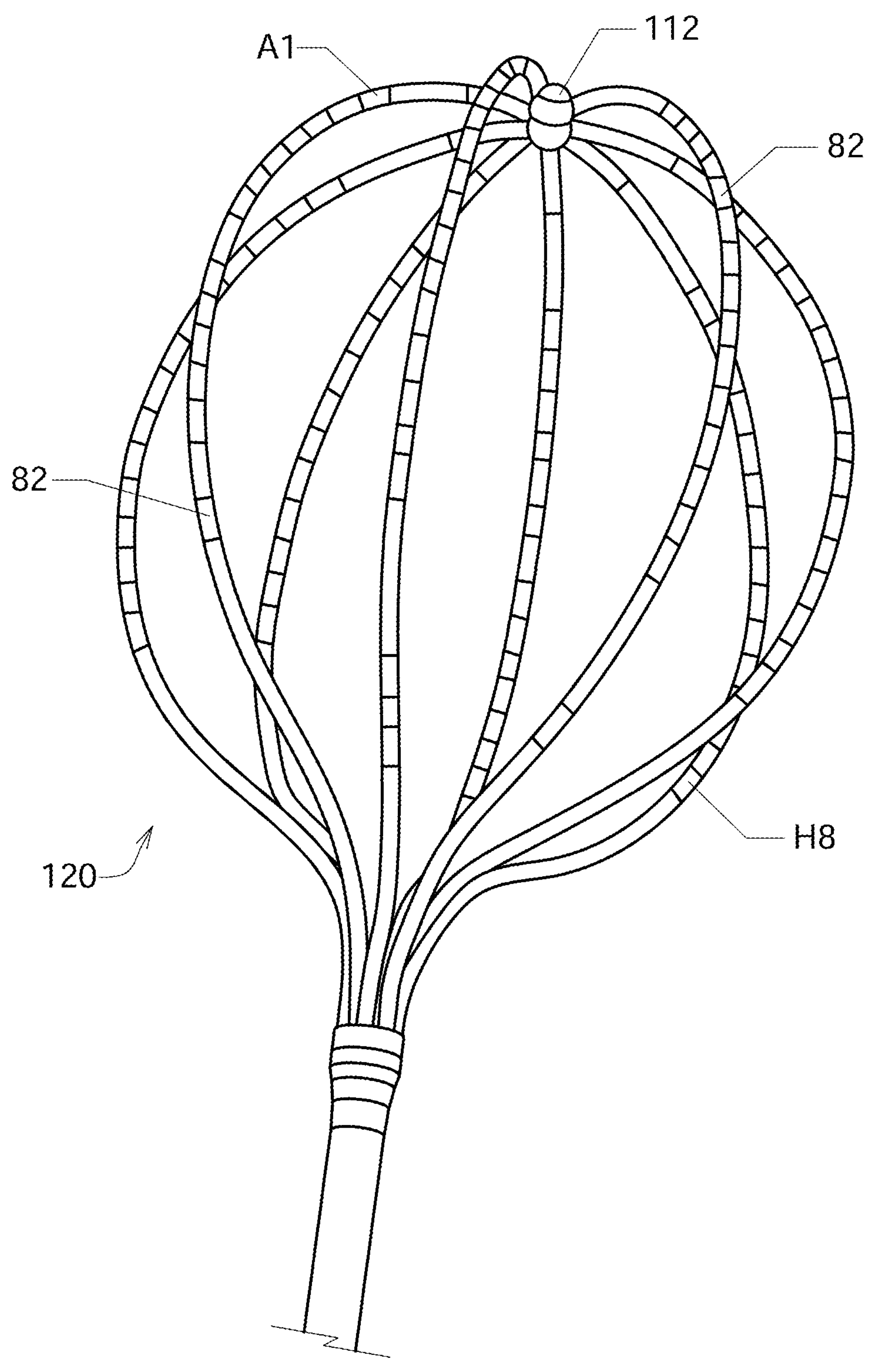
FIG. 3 shows an illustrative embodiment of a mapping electrode assembly 120.

FIG. 3 shows an illustrative embodiment of a basket catheter or mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes A1 through H8 (or individual electrodes 82) can provide comprehensive, real-time 3-D information over a single heartbeat.

Figure 4:
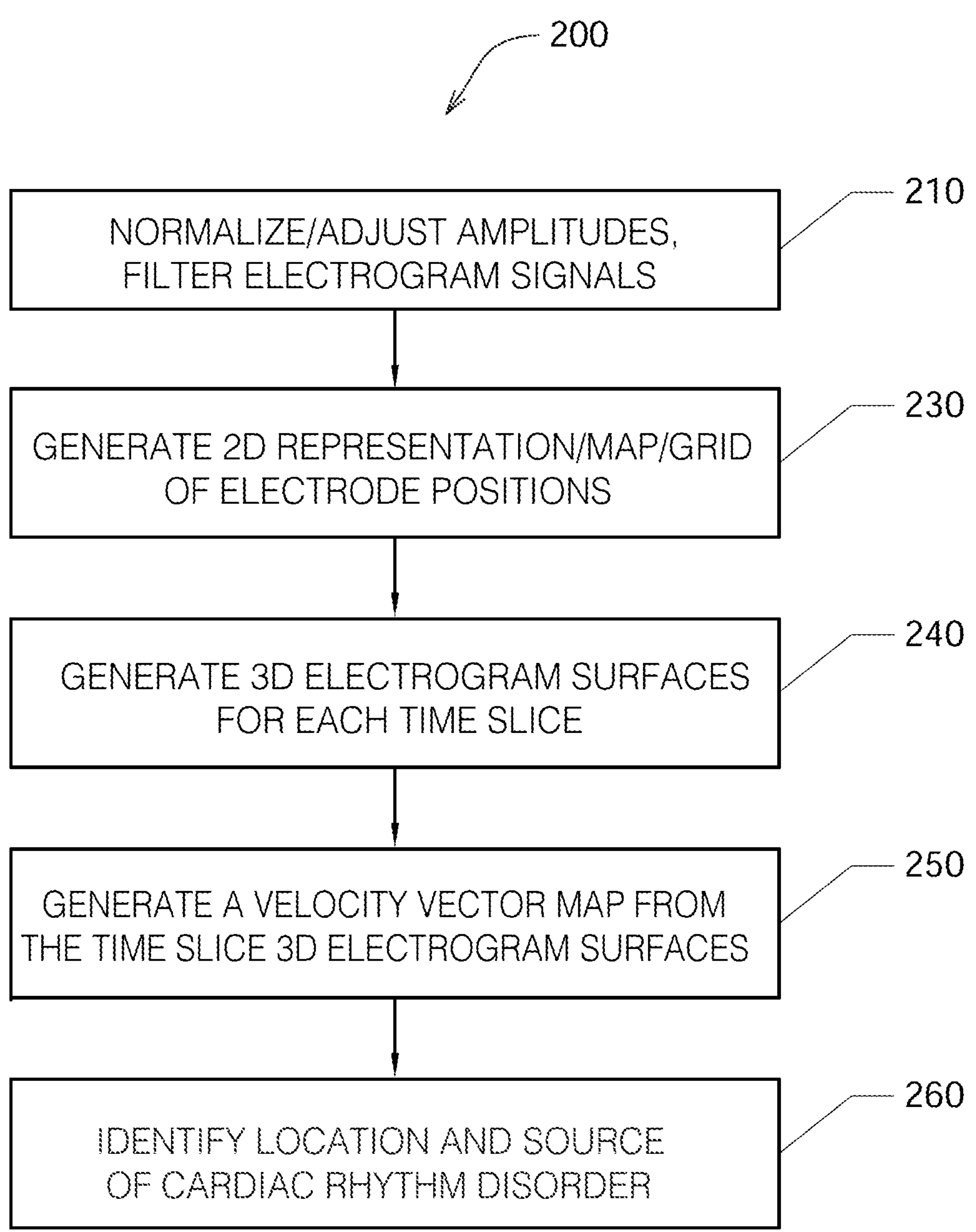
FIG. 4 shows one embodiment of a method 200 of detecting a location of a source of at least one cardiac rhythm disorder in a patient's heart.

FIG. 4 shows one embodiment of a method 200 of detecting a location of a source of at least one cardiac rhythm disorder in a patient's heart. At step 210, the amplitudes of electrogram signals acquired from electrodes located inside a patient's heart are normalized or adjusted. At step 230, positions A1 through H8 corresponding to each of the electrodes of mapping electrode assembly 120 are assigned to the individual electrogram signals that have been acquired. At step 230, a two-dimensional (2D) spatial map of electrode positions A1 through H8 is generated or provided. In some embodiments, a three-dimensional (3D) spatial map of electrode positions A1 through H8 is generated or provided. (As discussed above, fewer or more than 64 electrodes may be used to measure electrogram signals and/or surface ECGs, and electrode arrays other than 8×8 or rectangular grids are contemplated in the various embodiments.)

For discrete or selected times over which the electrogram signals are being analyzed and processed, at step 240 the amplitude-adjusted electrogram signals are processed to generate a plurality of three-dimensional electrogram surfaces (which according to one embodiment may be smoothed electrogram surfaces) corresponding at least partially to the 2D (or 3D) map, one surface being generated for each such discrete time. At step 250, the plurality of three-dimensional electrogram surfaces that have been generated through time are processed to generate a velocity vector map corresponding at least partially to the 2D (or 3D) map, which can also be called a three-dimensional electrographic flow or EGF map. The velocity vector map or EGF map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Method 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, method 200 has the advantages that it is robust against artifacts and provides a virtual resolution that is higher than the actual electrode density employed to acquire the EP mapping data through the use of a fitting method that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two- or three-dimensional bi-harmonic spline interpolation functions to generate such surfaces.

In one embodiment, electrogram signal data acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 2D projection of a grid representative of the interior surface of the patient's heart that is being mapped. In many applications, it has been discovered that such approximations of electrode locations yield perfectly useable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by, for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which as described above may be employed in conjunction with Green's function, has also been discovered to work especially well in the context of processing and analyzing electrogram signal data. In some embodiments, undesirable oscillations between data points are removed by interpolation with splines in tension, also using Green's function. A Green's function technique for interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step 240.

In one embodiment, Green's function G(x; x') is employed in step 240 for a chosen spline and geometry to interpolate data at regular or arbitrary output locations. Mathematically, the solution is w(x)=sum {c(i) G(x'; x(i))}, for i=1, n, and a number of data points {x(i), w(i)}. Once the n coefficients c(i) have been calculated, the sum may be evaluated at any output point x. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients c(i) may be determined by solving the n by n linear system w(j)=sum-over-i {c(i) G(x(j); x(i))}, for j=1, n; this solution is yields an exact interpolation of the supplied data points. For further details regarding the methods and mathematics underlying Green's function, see, for example: (1) "Moving Surface Spline Interpolation Based on Green's Function," Xingsheng Deng and Zhong-an Tang, Math. Geosci (2011), 43:663-680 ("the Deng paper"), and (2) "Interpolation with Splines in Tension: A Green's Function Approach," Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: 1. Theory and implementation, Mitasova, H., and L. Mitas, 1993, Math. Geol., 25, 641-655; Parker, R. L., 1994, Geophysical Inverse Theory, 386 pp., Princeton Univ. Press, Princeton, N.J.; Sandwell, D. T., 1987, Biharmonic spline interpolation of Geos-3 and Seasat altimeter data, Geophys. Res. Lett., 14, 139-142; Wessel, P., and J. M. Becker, 2008, Interpolation using a generalized Green's function for a spherical surface spline in tension, Geophys. J. Int, 174, 21-28, and Wessel, P., 2009, A general-purpose Green's function interpolator, Computers & Geosciences, 35, 1247-1254. Moving Surface Spline Interpolation Based on Green's Function, Xingsheng Deng, Zhong-an Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, or use in conjunction with Green's function, and which include, but are not limited to, inverse distance weighted methods of interpolation, triangulation with linear interpolation, bilinear surface interpolation methods, bivariate surface interpolation methods, cubic convolution interpolation methods, Kriging interpolation methods, Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting interpolation methods, simple weighted-average operator interpolation methods, multi-quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley. pp. 21-36), and "Surfaces generated by Moving Least Squares Methods," P. Lancaster et al., Mathematics of Computation, Vol. 37, No. 155 (July, 1981), 141-158).

As described above, in step 250 of FIG. 4, the plurality of three-dimensional electrogram surfaces may be processed through time to generate a velocity vector map or EGF map corresponding at least partially to the 2D (or 3D) map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Horn-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Horn-Schunck method has so far been discovered to provide superior results in the context of processing and analyzing cardiac electrogram signals, for reasons that are discussed in further detail below.

Two papers describe the Horn-Schunck method particularly well: (1) 15 "SimpleFlow: A Non-iterative, Sublinear Optical Flow Algorithm," Michael Tao et al., Eurographics 2012, Vol. 31 (2012), No. 2 ("the Tao paper"), and (2) "Horn-Schunck Optical Flow with a Multi-Scale Strategy," Enric Meinhardt-Llopis et al., Image Processing On Line, 3 (2013), pp. 151-172 ("the Meinhardt-Lopis paper"). The respective entireties of the Tao and Meinhardt-Lopis papers are hereby incorporated by reference herein.

In "Determining Optical Flow," by B. K. P. Horn and B. G. Schunck, Artificial Intelligence, Vol. 17, pp. 185-204, 1981, the entirety of which is also hereby incorporated by reference herein, a method for finding an optical flow pattern is described which assumes that the apparent velocity of a brightness pattern varies smoothly throughout most of an image. The Horn-Schunck method assumes smoothness in flow over most or all of an image. Thus, the Horn-Schunck method attempts to minimize distortions in flow and prefers solutions which exhibit smoothness. The Horn-Schunck method of estimating optical flow is a global method which introduces a global constraint of smoothness to solve the aperture problem of optical flow.

A description of some aspects of conventional application of the Horn-Schunck method is set forth in U.S. Pat. No. 6,480,615 to Sun et al. entitled "Motion estimation within a sequence of data frames using optical flow with adaptive gradients," the entirety of which is also hereby incorporated by reference herein. As described by Sun et al., the Horn-Schunck computation is based on the observation that flow velocity has two components, and that a rate of change of image brightness requires only one constraint. Smoothness of flow is introduced as a second constraint to solve for optical flow. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis, image brightness is considered at pixel (x,y) in an image plane at time t to be represented as a function I(x,y,t). Based on initial assumptions that the intensity structures of local time-varying image regions are approximately constant under motion for at least a short duration, the brightness of a particular point in the image is constant, so that dl/dt =C. Based on the chain rule of differentiation, an optical flow constraint equation (I) can be represented as follows:

$$Ix(x, y, t) \cdot u + I\ y(x, y, t) \cdot v + I\ t(x, y, t) = 0,$$

where

Ix=≠I(x,y,t)/≠x=horizontal spatial gradient of the image intensity;

Iy=≠I(x,y,t)/≠y=vertical spatial gradient of the image intensity;

It=≠I(x,y,t)≠t=temporal image gradient of the image intensity;

u=dx/dt=horizontal image velocity (or displacement); and v=dyidt=vertical image velocity (or displacement).

The above optical flow equation is a linear equation having two unknowns, (i.e., u and v). The component of motion in the direction of the brightness gradient is known to be It/(Ix 2+Iy 2)½. However, one cannot determine the component of movement in the direction of the iso-brightness contours at right angles to the is brightness gradient. As a consequence, the optical flow velocity (u,v) cannot be computed locally without introducing additional constraints. Horn and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will vary smoothly almost everywhere.

Advantages of the Horn-Schunck method include that it yields a high density of flow vectors, i.e., the flow information missing in inner parts of homogeneous objects is filled in from the motion boundaries. On the negative side, the Horn-Schunck method can be sensitive to noise.

The foregoing discussion regarding how the Horn-Schunck optical flow technique typically focuses on conventional applications, where the brightness or intensity of an object changes over time (which is where the term "optical flow" is derived from). Here, the brightness or intensity of an object is not the issue at hand. Instead, the amplitudes of electrogram signals, and how they change shape and propagate in time and space over a patient's heart, are sought to be determined. One underlying objective of method 200 is to produce a vector velocity map, which is a representation of electrographical flow (and not optical flow) within a patient's heart. Instead of looking for differences or changes in optical brightness or intensity, changes in the velocity, direction and shape of electrical signals (i.e., changes in electrographical flow) across a patient's heart are determined. That is, method 200 does not process optical measurement data corresponding to intensity or brightness, but processes electrical measurement data corresponding to amplitude, potential shape, and/or voltage.

One reason why method 200 works so well in detecting the locations of the sources of cardiac rhythm disorders and irregularities is that ion channels in a patient's heart produce action potential voltages that are relatively constant (except in areas of fibrosis). As described above, the Horn-Schunck method assumes "brightness constancy" as one of its key constraints. The normalized/amplitude-adjusted electrogram signals provided by step 210 help satisfy this key constraint of the Horn-Schunck method so that this method may be applied successfully in step 250.

In addition, because of the stability imparted to electrographical flow solutions determined using the Horn-Schunck method, artifacts and noise are generally low in velocity vector maps generated in step 250. In fact, it is believed that the Horn-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Method 200 described and disclosed herein also does not employ spatial derivatives of electrical potentials (as is done by Deno et al. and Kumaraswamy Nanthakumar using "omnipolar" signals) or time derivatives of electrogram signals (as is done in the TOPERA system). Time derivatives of signals are known to increase noise. Method 200 has as its key inputs the potentials of electrogram signals (not their derivatives). As a result, method 200 is notably free from the effects of spurious noise and artifacts introduced by time-derivative data processing techniques, including in step 250.

In another embodiment, the velocity vector map of step 250 is generated using the Lucas-Kanade optical flow method, which is a differential method for optical flow estimation developed by Bruce D. Lucas and Takeo Kanade. It assumes that the flow is essentially constant in a local neighbourhood of a pixel under consideration, and solves the basic optical flow equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, it cannot provide flow information in the interior of uniform regions of the image. See "An Iterative Image Registration Technique with an Application to Stereo Vision," Bruce D. Lucase, Takeo Kanade, Proceedings of Imaging Understanding Workshop, pp. 121-130 (1981), the entirety of which is hereby incorporated by reference herein.

In yet another embodiment, various aspects of the Horn-Schunck and Lucas-Kanade methods are combined to yield an optical flow method that exhibits the local methods inherent in Lucas-Kanade techniques and the global methods inherent in the Horn-Schunck approach and its extensions. Often local methods are more robust under noise, while global techniques yield dense flow fields. See, for example, "Lucas/Kanade Meets Horn/Schunck: Combining Local and Global Optic Flow Methods," Andrés Bruhn, Joachim Weickert, Christoph Schnörr, International Journal of Computer Vision, February 2005, Volume 61, Issue 3, pp 211-231, the entirety of which is hereby incorporated by reference herein.

Various embodiments of method 200 feature several advantages with respect to prior art systems and methods that generate intracardiac images and attempt to detect the locations of cardiac rhythm disorders or irregularities. A key underlying assumption of signal processing techniques that employ Hilbert Transform, Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of method 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of method 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by method 200 are not assumed to be singularities in a phase map (as is assumed in techniques based upon frequency domain or Hilbert transform signal processing). This key difference also explains why the rotational direction of a rotor can be revealed or detected accurately by method 200 (and not at all, or very unsatisfactorily, using the frequency domain or Hilbert transforms of other methods employed to detect rotors). Note that in some embodiments, however, Hilbert, DFT and/or FFT signal processing components may be or are included in the data processing flow of method 200 (e.g., DSP filtering, deconvolution, etc.).

Figure 5A:
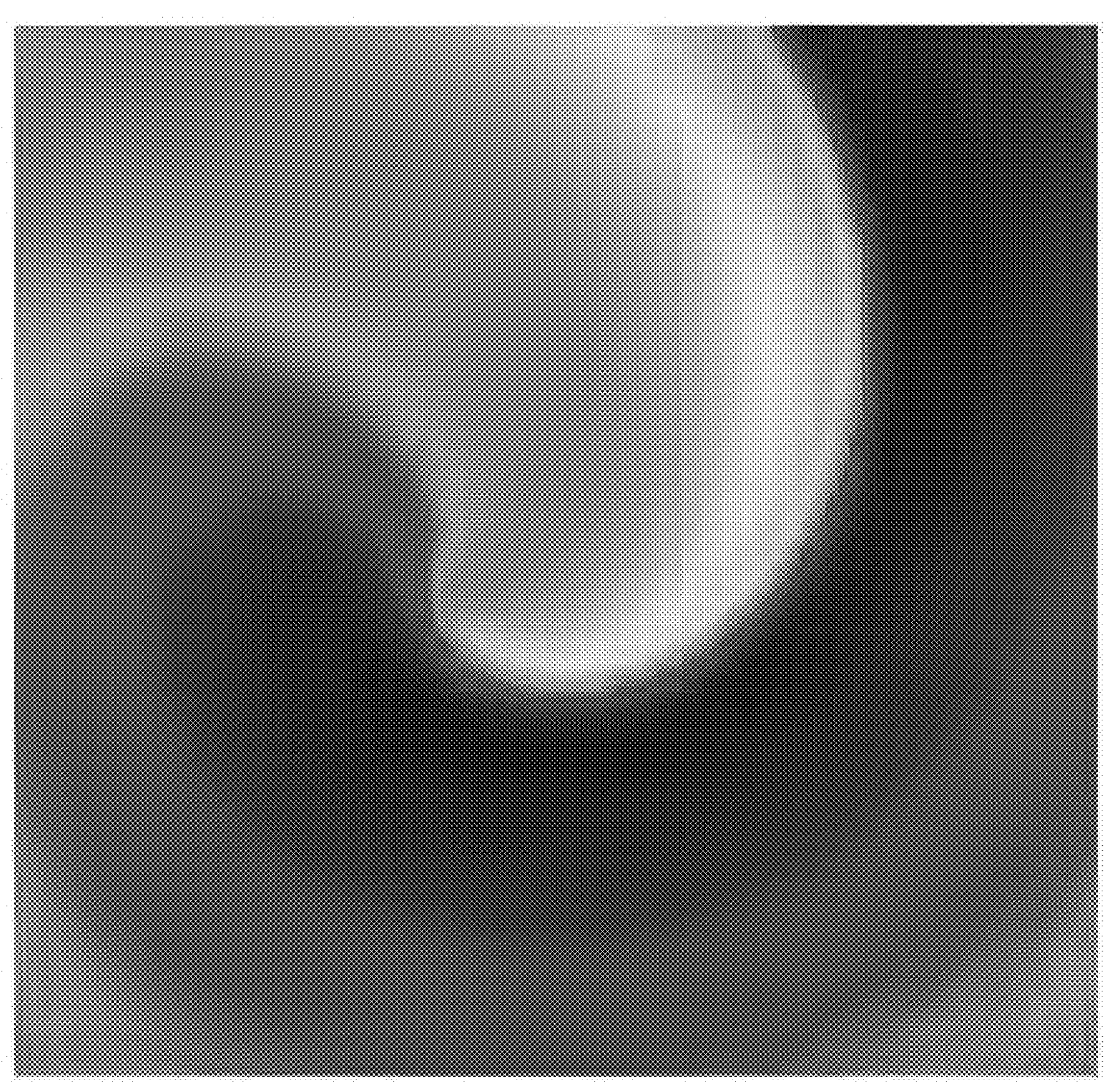
FIG. 5A shows a simple rotor model.

Referring now to FIG. 5A, there is shown a simple rotor model. This model was used to generate simulated ECG signals sensed by an 8×8 array of virtual electrodes. The simple rotor model shown in FIG. 5A is from "Chaste: An Open Source C++ Library for Computational Physiology and Biology, "Gary R. Mirams, et al. PLOS Computational Biology, Mar. 14, 2013, Vol. 9, Issue 3, e1002970, the entirety of which is hereby incorporated by reference herein.

Figure 5B:
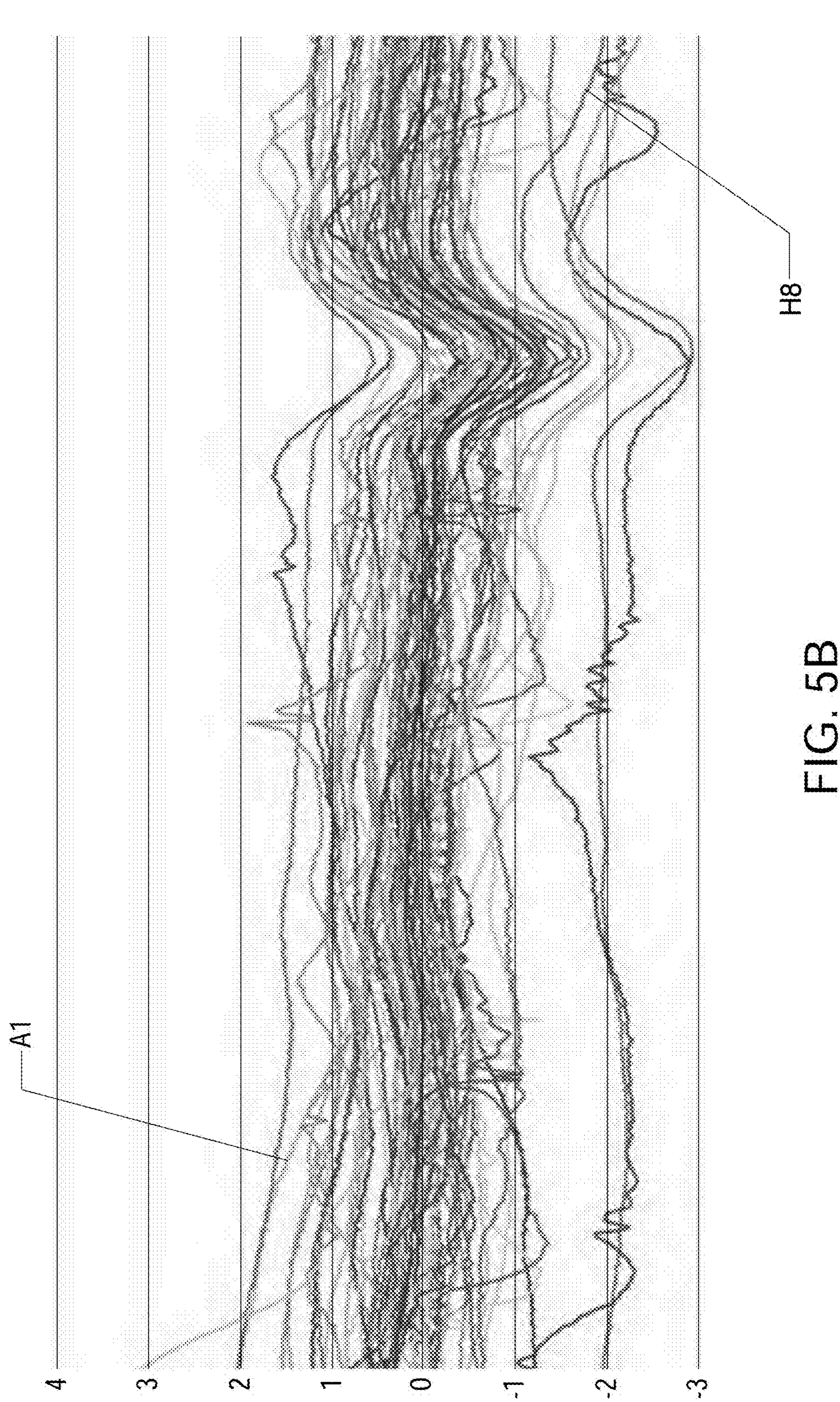
FIG. 5B shows sensed artifacts in electrogram signals.

FIG. 5B shows artifacts in electrogram signals derived from actual patient is data, where 400 msec traces were recorded using a 64-electrode basket catheter located in the left atrium of a patient suffering from atrial fibrillation. As shown in FIG. 5B, the sensed artifacts in the electrogram signals include DC offsets of several millivolts that shift with time, a common far-field ventricular depolarization superimposed on the local potentials sensed by individual electrodes, and noise. Moreover, the amplitudes of the various sensed electrogram signals shown in FIG. 5B will be seen to vary considerably. These amplitude variations result at least in part on from varying degrees to which individual electrodes touch, or are physically coupled to, the patient's endocardial surface. Electrogram signals corresponding to electrodes in loose, poor or no contact with a patient's endocardium may be an order of magnitude smaller than those where electrodes are well coupled to the endocardial surface.

Figure 5C:
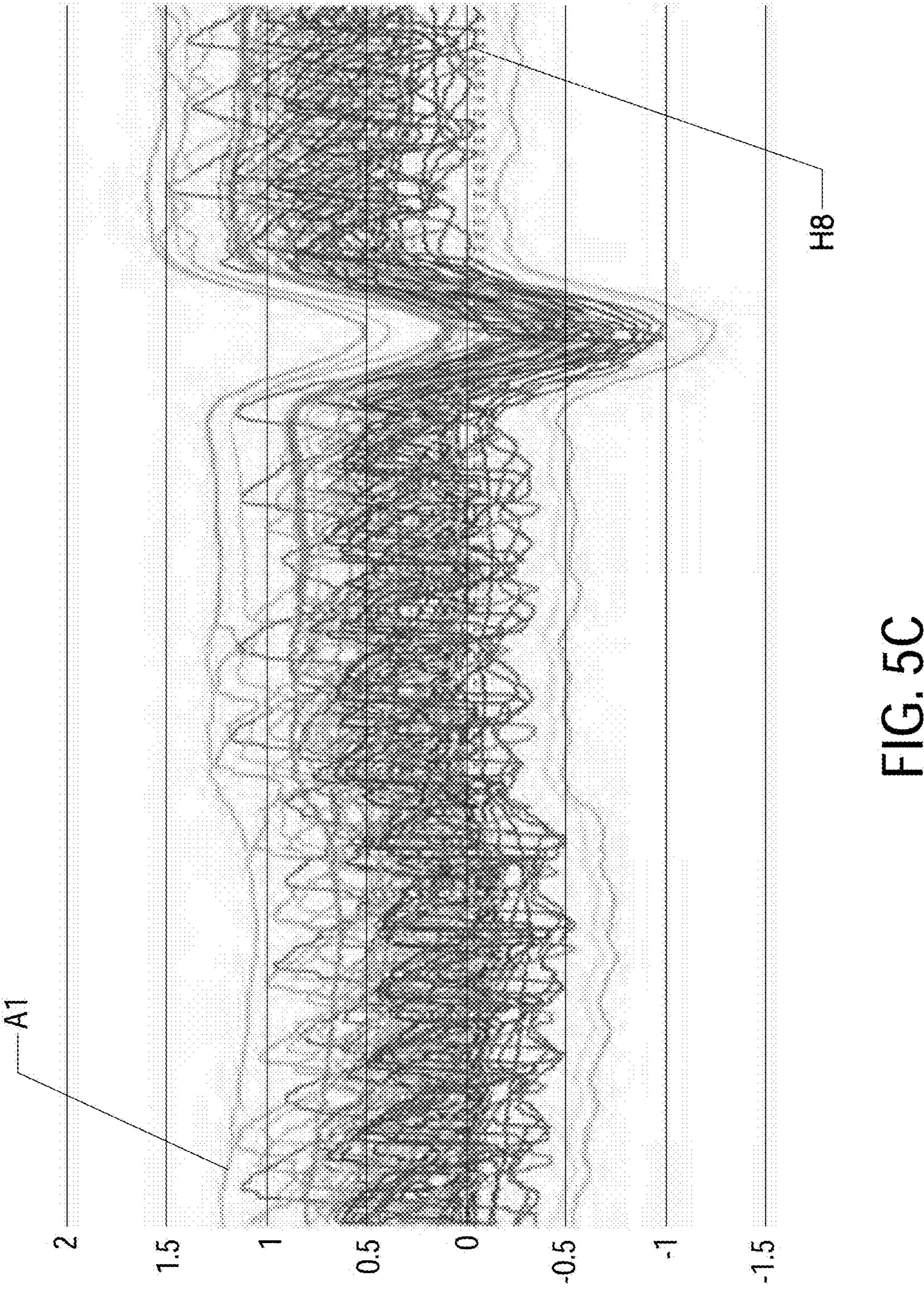
FIG. 5C shows the artifacts of FIG. 5B superimposed on simulated ECG signals.
Figure 5D:
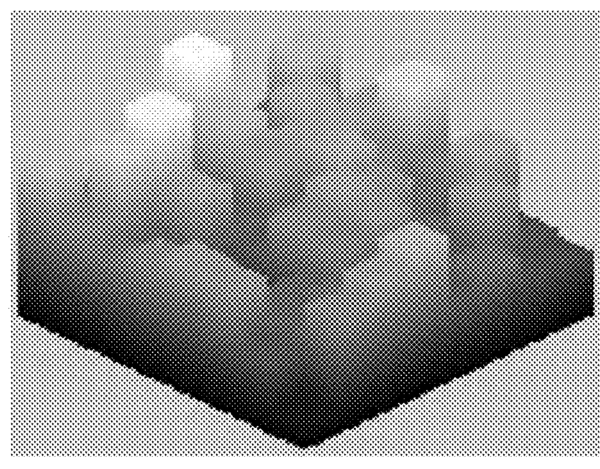
FIG. 5D shows a box plot corresponding to an 8×8 array of 64 electrode signals.

FIG. 5C shows the artifacts of FIG. 5B superimposed on the simulated ECG signals generated from the rotor model of FIG. 5A. FIG. 5D shows a box plot corresponding to the 8×8 array of 64 electrode signals shown in FIG. 5A at a selected common time for all traces. Because of the artifacts from FIG. 5B introduced into the electrogram signals of FIG. 5C, the box plot of FIG. 5D appears quite irregular and chaotic, and the original spiral shape of the underlying rotor of FIG. 5A is not discernable to the eye.

The data shown in FIG. 5C were used to perform an analysis in accordance with method 200, which was carried out in three main steps: (1) normalization/adjustment/filtering of electrogram signals; (2) generating three-11 dimensional smoothed electrogram surfaces for discrete times or time slices from the normalized/adjusted/filtered electrogram signals generated in the first main step, and (3) generating a velocity vector map based on the smoothed electrogram surfaces generated in the second main step.

Figure 5E:
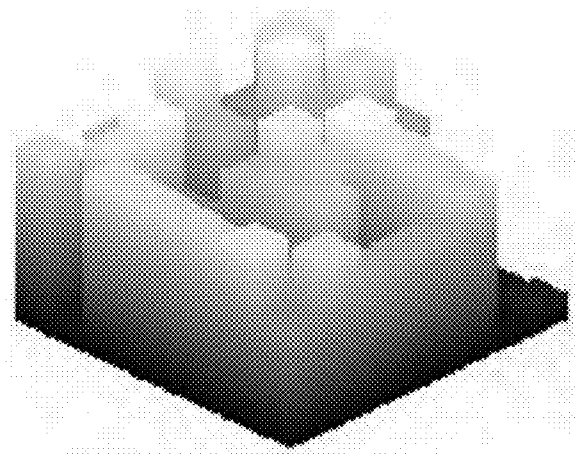
FIG. 5E shows the data of FIG. 5D after they have been subjected to an electrode signal normalization, adjustment and filtering process.

Described now is one embodiment and illustrative example of the first main is step of the method 200 (normalization/adjustment/filtering of electrogram signals). Referring now to FIG. 5E, there are shown the data of FIG. 5D after they have been subjected to one embodiment of an electrode signal normalization, adjustment and filtering process. After normalization and filtering, the simple rotor structure shown in FIG. 5A becomes visible in FIG. 5E. Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5E.

Next, a sliding time window ranging between about 0.1 seconds and about to 1 second in length was applied to each filtered electrogram signal to generate individual amplitude-adjusted electrogram signals. (in some embodiments, the length of the sliding time window corresponds to, or is less than, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now I describe one embodiment and illustrative example of the second main step of the method 200 (generating three-dimensional electrogram surfaces for discrete times or time slices, or estimation of spatial wave shapes). The second step of method 200 takes the spatial distributions of all electrodes and their normalized voltage values at discrete times (e.g., the data represented by the box plots corresponding to selected discrete times within the selected time window over which electrogram signals were acquired and measured), and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity (e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, method 200 is capable of detecting spatial changes in action potential wavefronts or wave shapes using time domain information (i.e., small amplitude changes between time samples) to estimate changes in the spatial domain (where relatively small shifts in action potentials occur at given electrode measurement locations).

Figure 5F:
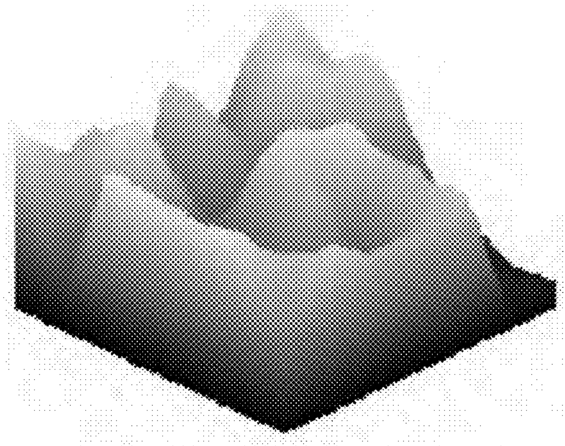
FIG. 5F shows a surface generated from the data shown in FIG. 5E.

One embodiment of a method for estimating action potential wavefronts or wave shapes employs an 8×8 rectangular electrode grid (e.g., TOPERA®-like) model, which operates in two principal steps. First, each electrode/electrogram signal value at a discrete moment in time defines the height of its respective box in the "chess field" box plots shown in FIGS. 5D and 5E. Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 2D biharmonic spline interpolation techniques in combination with Green's function. Using the foregoing simple averaging approach, the smoothed electrogram surface of FIG. 5F was generated from the data shown in FIG. 5E. As shown in FIG. 5F, a spatial wave shape estimate of a rotor appears prominently in the forward center portion of the resulting smoothed surface, which tracks closely the original spiral wave shown in FIG. 5A.

Described now is one embodiment and illustrative example of the third main step of method 200 (generating a velocity vector map based on the electrogram surfaces). The third main step of method 200 uses the action potential wave shape estimates or electrogram surfaces generated at discrete times or time splices provided by the second main step to calculate a velocity vector map. For each sample interval a spatial wave shape or smoothed surface is calculated according to the second main step described above. Since the wave shapes differ only by a small delta between individual samples, and minimum and maximum values are normalized, shift vectors can be calculated at a spatial resolution that is higher than the spatial resolution of the electrodes (e.g., 30×30 samples). Since individual shifts between samples may differ according to random error, a velocity vector fit can be generated using 40 to 100 samples, where an average of observed shift vectors of the action potential wave shape care calculated. If the angle of a rotating wavefront is shifted by a few degrees per sample, the vector arrows will exhibit a circular pattern and in fact can resolve circles that are much smaller than inter-electrode distances. In one embodiment, the third main step of the method employs a vector pattern equation that best fits the observed movement of the evaluated spatial element or wavefront. In one embodiment that has been discovered to provide excellent results, and as described above, the velocity vector map is calculated using the Horn-Schunck optical flow method described above. That is, in one embodiment the Horn-Schunck optical flow method is used in the third main step of method 200 to estimate the velocity and direction of wavefronts or wave shapes between sampled times. Velocities of 40 to 100 samples are typically averaged to yield the most stable results.

Figure 5G:
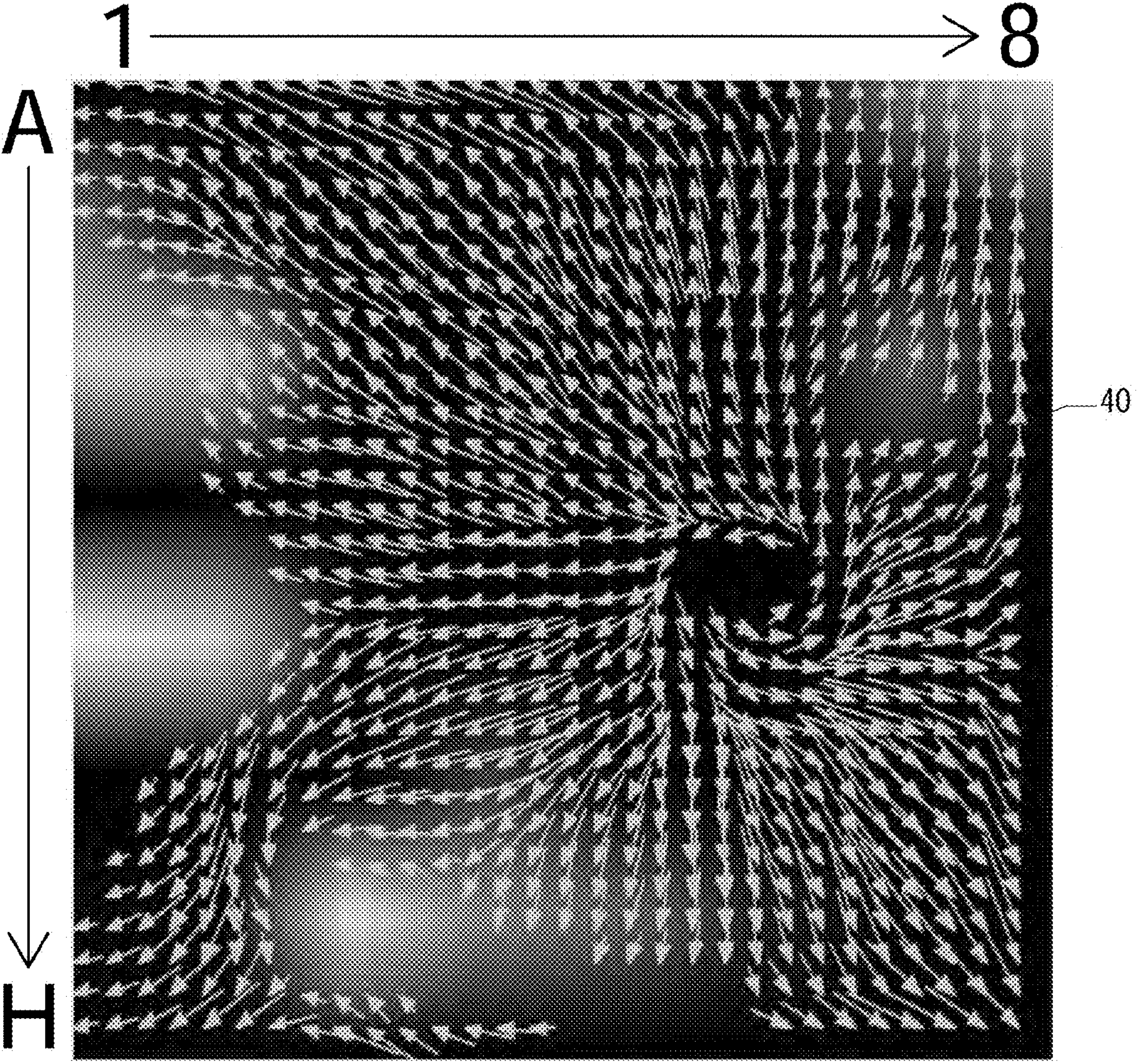
FIG. 5G shows wavefront velocity vectors.

FIG. 5G shows the resulting wavefront velocity vectors, which are shown in FIG. 5G and elsewhere in the Figures as arrows 40 having directions and magnitudes associated therewith, calculated from a series of 60 averaged time slices of smoothed surfaces samples corresponding to the data shown in FIG. 5F. An active rotor is distinctly visible in the right-hand central portion of FIG. 5G, where arrows are flowing tightly in a counterclockwise direction. In FIG. 5G, action is potential wavefronts are seen to be moving outwardly away from the detected active rotor (as would be expected in the case of an active rotor)).

Figure 6A:
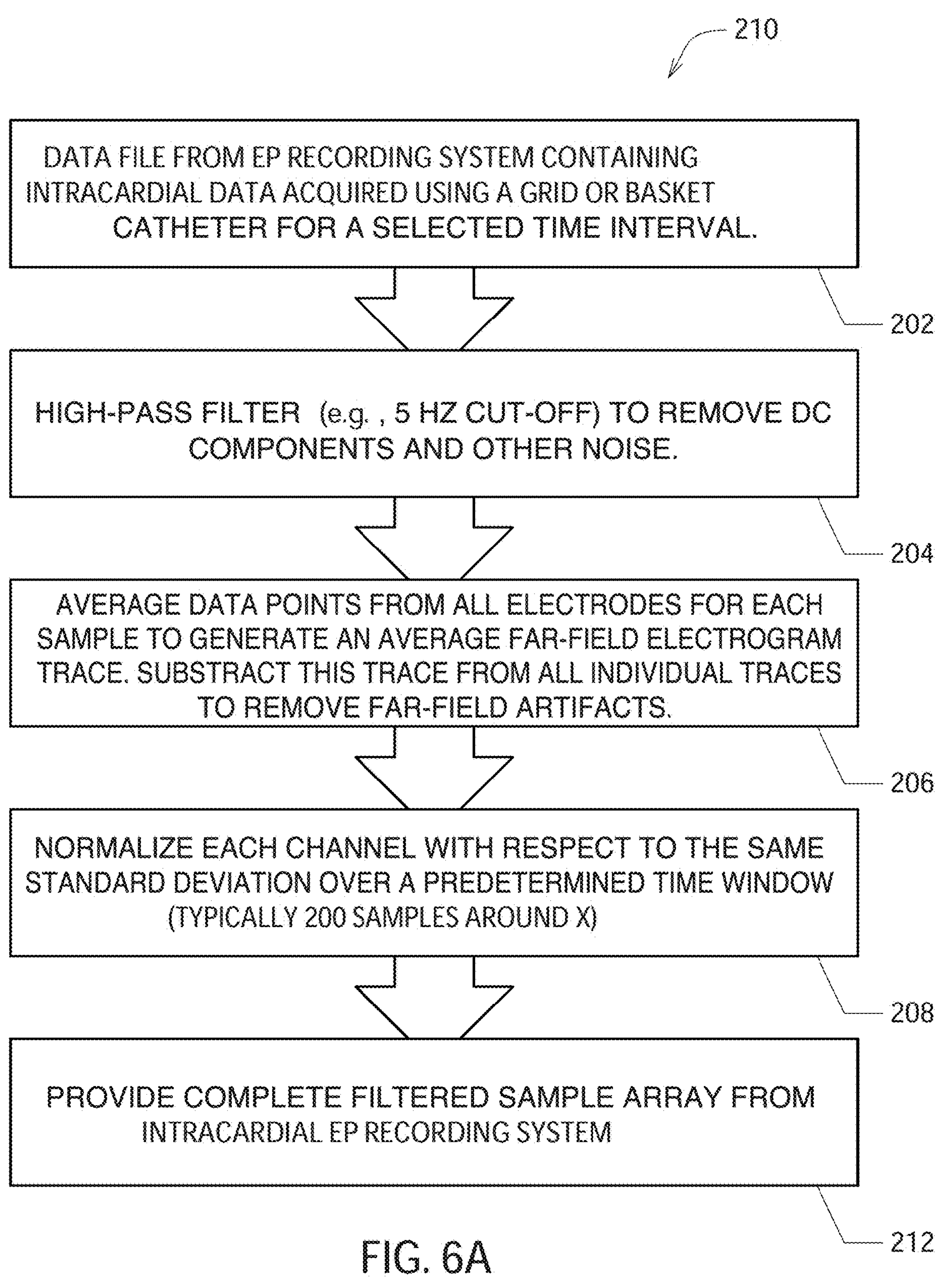
FIGS. 6A through 6C show details regarding one embodiment of a method 200 shown in FIG. 4.
Figure 6B:
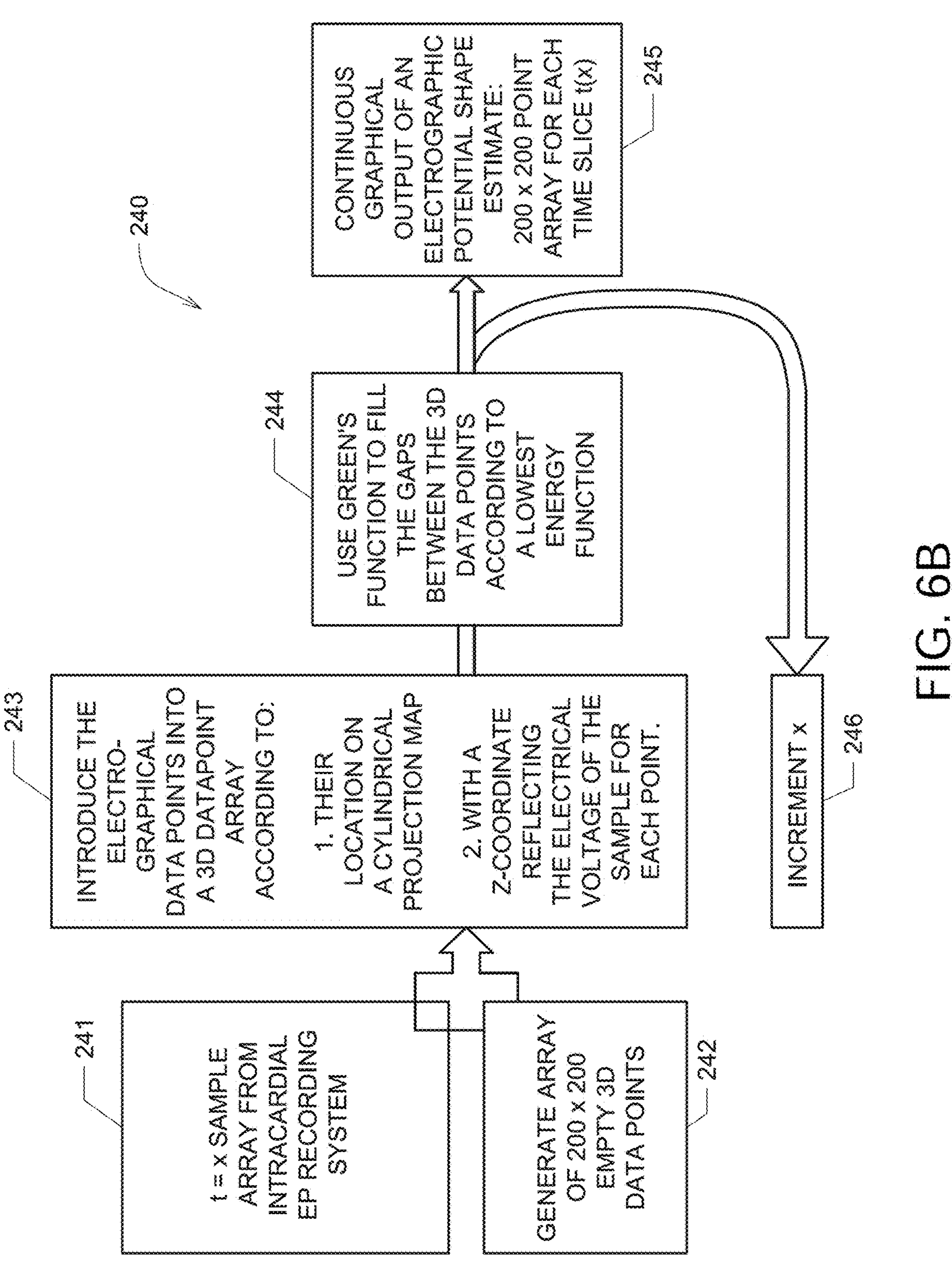
Figure 6C:
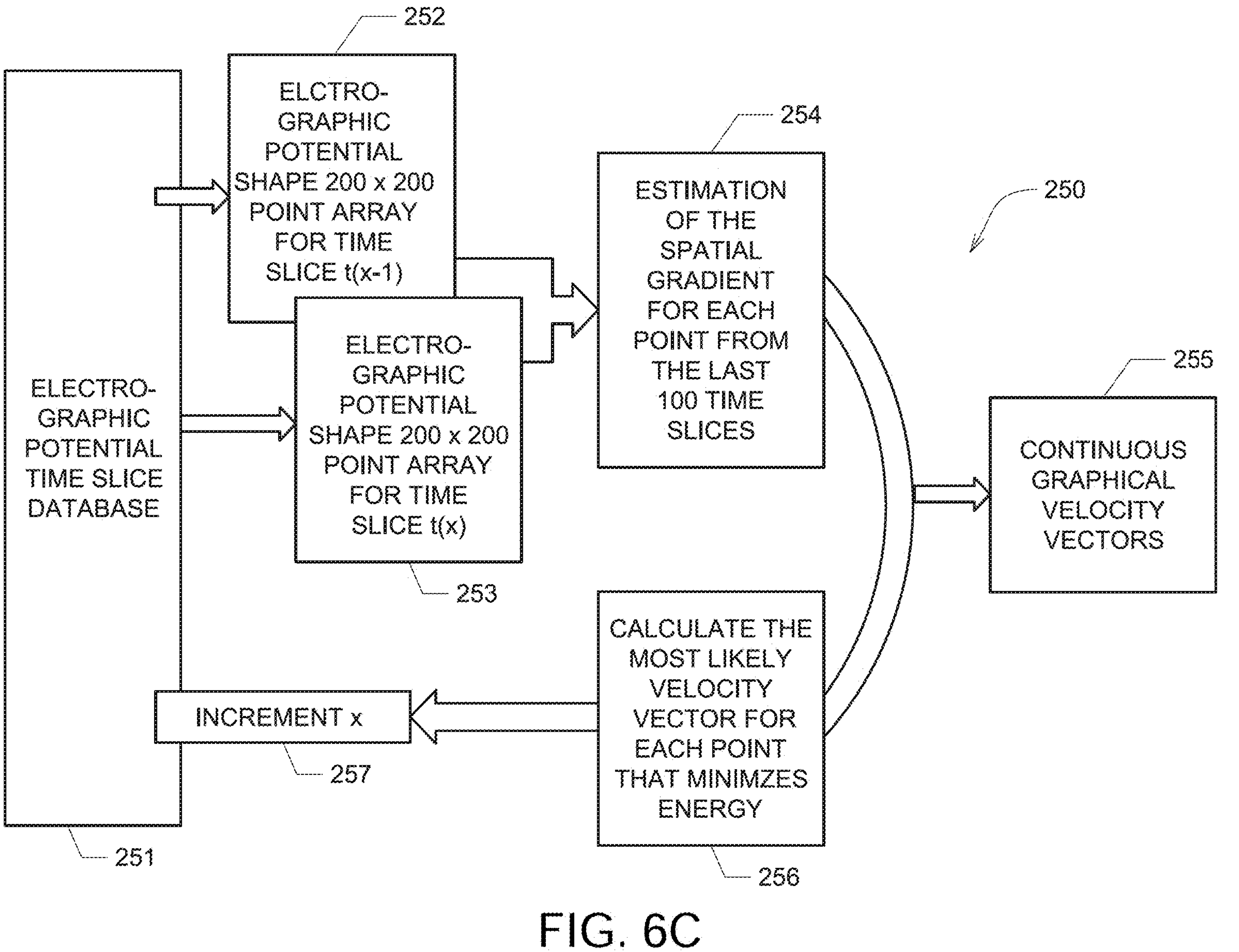

Referring now to FIGS. 6A, 68 and 6C, and with further reference to FIG. 4, there are shown some of the individual steps corresponding to the three main steps 230, 240 and 250 carried out according to one embodiment of method 200 disclosed and described herein, FIG. 6A shows one embodiment of steps 202 through 212 of main step 210 of FIG. 4 ("normalize/adjust amplitudes, filter electrogram signals). In FIG. 6A, step 202 is shown as comprising receiving a data file corresponding to the EP recording of electrogram signals from a basket or other type of EP recording catheter positioned in a patient's heart 10. The time interval over which such electrogram signals are recorded inside the patient's heart 10 may, of course, vary according to, among other things, the requirements of the diagnosis, examination, monitoring and/or treatment that is to be performed, and/or the suspected or known cardiac rhythm disorder from which the patient suffers. Illustrative, but non-limiting, examples of such time intervals range between about a second and one minute or more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high-pass filter is applied, although other filters, including band-pass filters, are contemplated, including, but not limited to, 10 Hz high-pass filters, 5-20 Hz band-pass filters, and 5-50 Hz band-pass filters. Notch- and low-pass filtering may also be applied in step 204. Hanning, trapezoidal and other digital filtering and/or Fast Fourier Transform (FFT) filtering techniques may also be applied.

At step 206, an average far-field electrogram signal is generated by stacking and averaging all electrogram traces. In the case of atrial EP recordings, the resulting estimate of a far-field ventricular depolarization is subtracted from each trace individually, thereby removing or at least reducing the far-field component therefrom.

At step 208, the amplitudes of individual filtered electrogram signals are normalized with respect to a given standard deviation occurring over a predetermined time window (e.g., a moving window of 200 samples around a time value "x").

At step 212, a complete filtered sample array from the grid or basket catheter is provided as an output from first main step 210.

Referring now to FIG. 6B, there is shown one embodiment of the second main step 230 of method 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time slice).

In FIG. 68, second main step 240 is shown as including steps 241 and 243, which according to one embodiment are performed in parallel or near-parallel. At step 241, digitally sampled and processed electrogram signals from step 212 of FIG. 6A are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110. Positional data from imaging or navigation system 70 can be provided at this stage to improve the positional accuracy of the individual locations within such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating method, is used to generate a surface of Z-values for each time slice or sampled time (more about which is said below). In one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each time slice or sampled time. Note that in some embodiments the intervals at which time slices are selected, or the individual time slices themselves, may be predetermined, or may be selected automatically or by the user.

FIG. 6C shows step 250 corresponding to one embodiment of the third main step of FIG. 4 (processing the plurality of three-dimensional electrogram surfaces generated through time to generate a velocity vector map corresponding at least partially to the 2D or 3D map) carried out, by way of non-limiting example, using optical flow analysis and estimation techniques described and disclosed elsewhere herein. In FIG. 6C, third main step 250 is shown as including step 251, which in one embodiment entails sequentially accessing the individual surfaces generated for selected time slices and/or discrete times in step 240. At steps 252 and 253, adjacent time slices are analyzed and processed sequentially. In step 254, a spatial gradient corresponding to each point of the representation, map or grid is calculated say over, for example, the last 100 time slices. At step 255, a continuous graphical output of calculated flow vectors can be provided as a real-time or near-real-time output. At step 256, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5G, 7E, 7I, 7J, 7K, 7L, 8, 9, 10A, 10C, and 10E.

FIGS. 7A through 7J show the results of processing simulated atrial cardiac rhythm disorder data using the methods and techniques described and disclosed above, where the concept of analyzing complex rotor structures was applied to a data set of simulated data. The simulated data shown in FIG. 7A primarily comprised stable active and passive rotors, as described in Carrick et al. in "Prospectively Quantifying the Propensity for Atrial Fibrillation: A Mechanistic Formulation," R. T. Carrick, P. S. Spector et al.; Mar. 13, 2015, PLOS ONE, DOI:10.1371, journal.pone.0118746, the entirety of which is hereby incorporated 1c by reference herein. From Carrick, et al.'s video corresponding to the foregoing publication, and referring now to FIG. 7A herein, stable rotor data were recorded for a frame delineated by the indicated blue square, where there are seven rotors. The recording was accomplished using the luminance of the video frame in an 8×8 matrix with an 8-bit signal depth, thereby to simulate electrogram signal data acquired using a conventional 64-electrode 8×8 basket catheter. The overall video comprised 90 frames. All data shown n FIG. 7A were taken from frame 60. Signal amplitudes from frame 60 are shown in the chess field and box plots of FIGS. 7B and 7C, respectively.

Figure 7A:
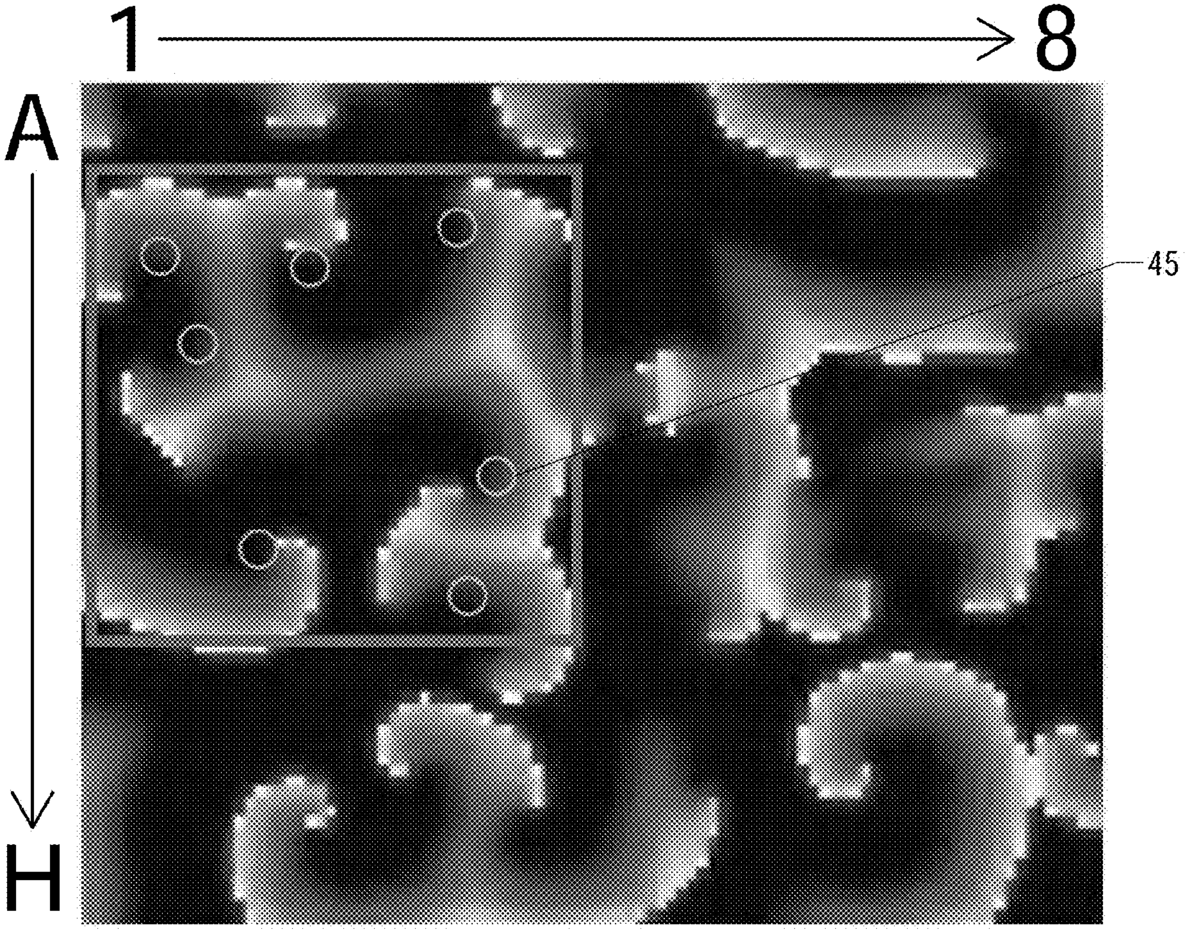
FIGS. 7A through 7J show the results of processing simulated atrial cardiac rhythm disorder data in accordance with one embodiment of method 200.

In FIG. 7A, 7 rotors are shown as green circles 45 lying within the blue rectangle. In FIGS. 7B and 7C, box plots of 8×8 matrix amplitudes are shown having amplitudes corresponding to frame 60. FIG. 7D shows the estimated wavefront or smoothed surface corresponding to frame 60. FIG. 7E shows the vector velocity map generated from the data corresponding to FIG. 7A (which was generated on the basis of all 90 frames or times slices). Reference to FIG. 7E shows that seven active rotors (marked as green circles 45) are apparent, as are two passive rotors (marked as red stars 46).

Figure 7B:
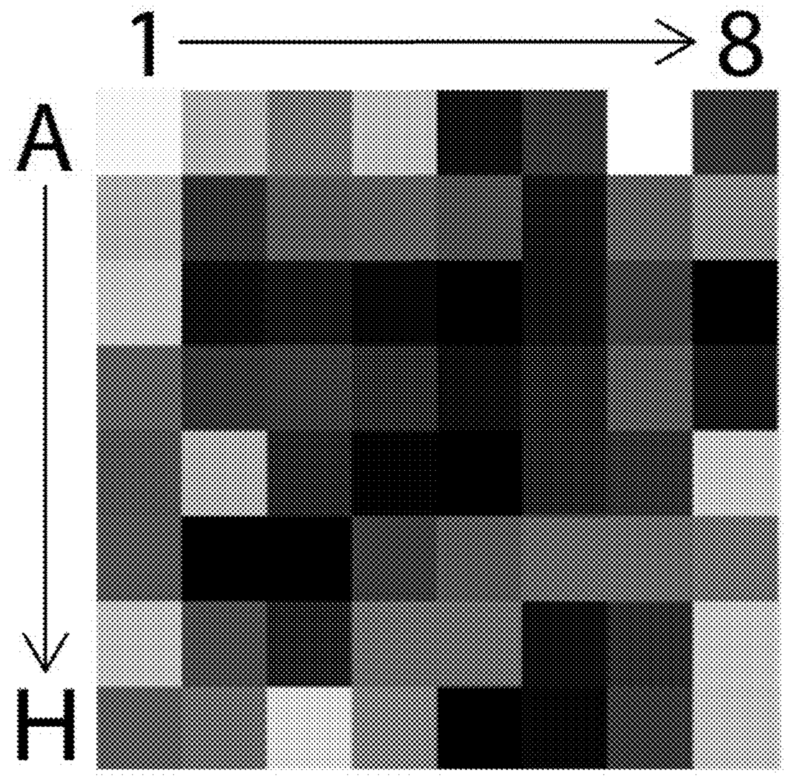
Figure 7C:
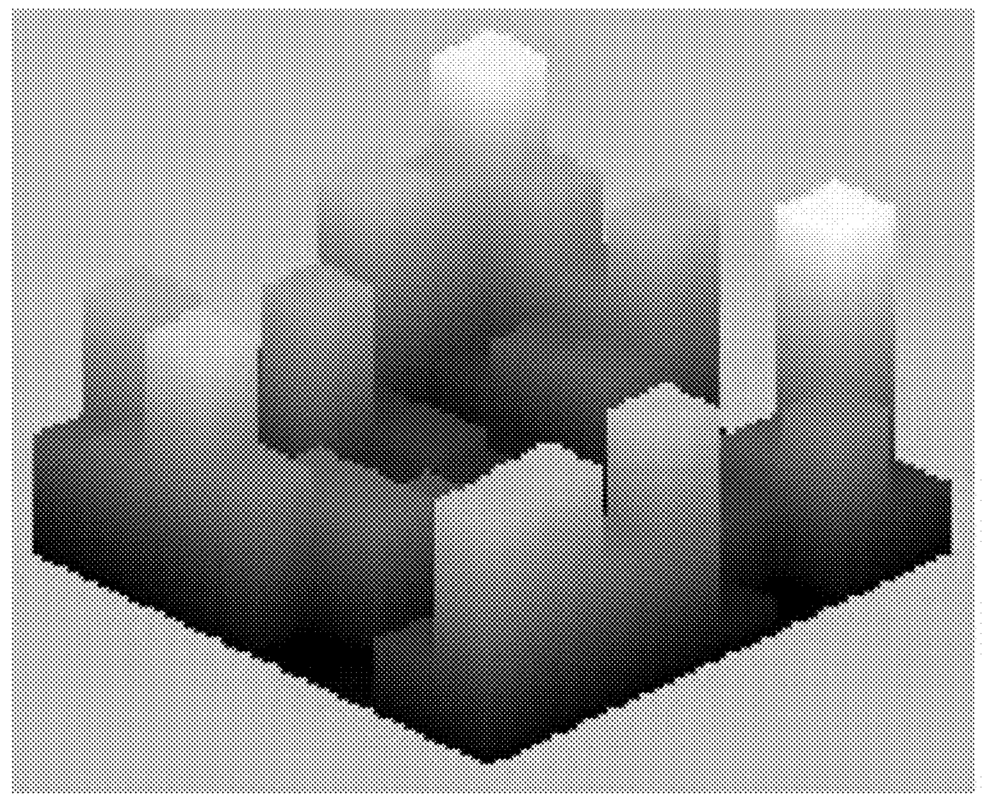
Figure 7D:
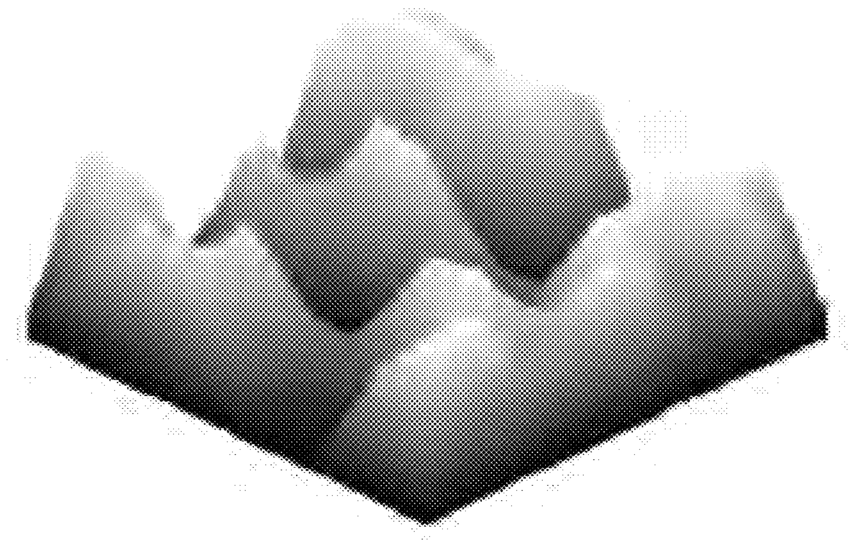
Figure 7E:
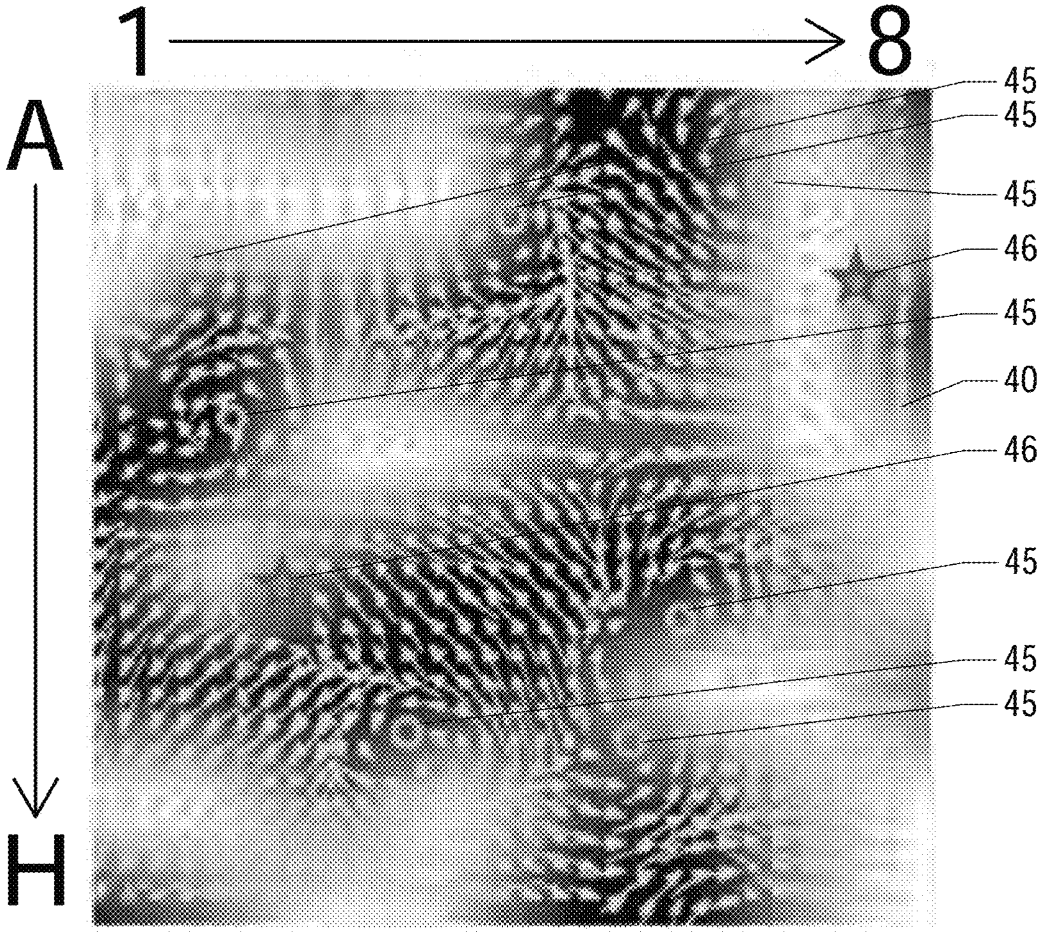

Referring now to FIGS. 7B and 7C, it will be seen that the 2D and 3D box patterns shown therein provide rough estimates of the spatial wavefronts shown in FIG. 7A. In FIG. 7D, however, the original data shown in FIG. 7A are reproduced fairly accurately, and also provide a good input to the vector velocity map of FIG. 7E (which nicely reveals the 7 active rotors visible in FIG. 7A). The yellow vector arrows in FIG. 7E not only show the rotational centers of the individual rotors, but also show that active rotors indicated by green circles are driving sources of the wave fronts because the calculated vectors of the active rotors always point centrifugally away from the rotor centers. In contrast, the two red stars shown in FIG. 7E indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown In FIGS. 7A through 7D were determined by introducing simulated variable amplitude DC-offset noise and artifacts into the electrogram signals. The objective was to test the extent to which such artifacts and noise might impair or disable the ability of method 200 to detect rotors in the data.

Figure 7F:
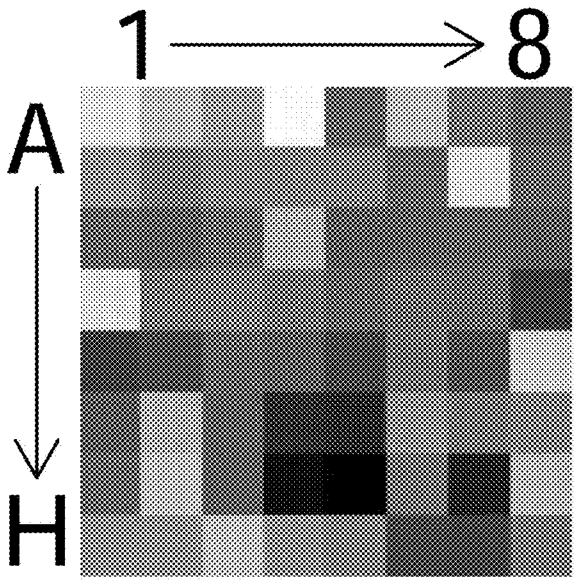
Figure 7G:
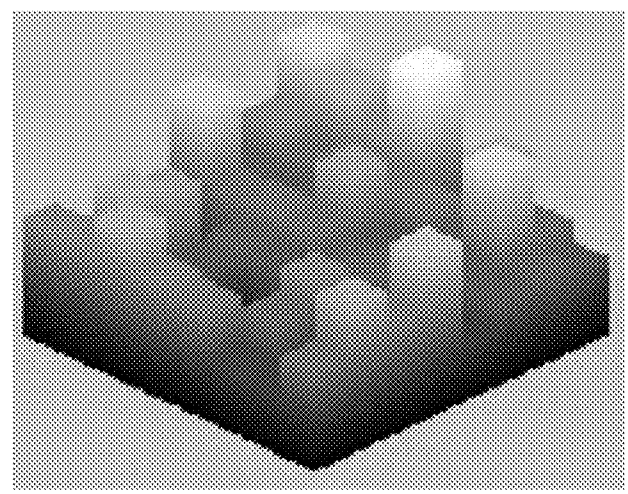
Figure 7H:
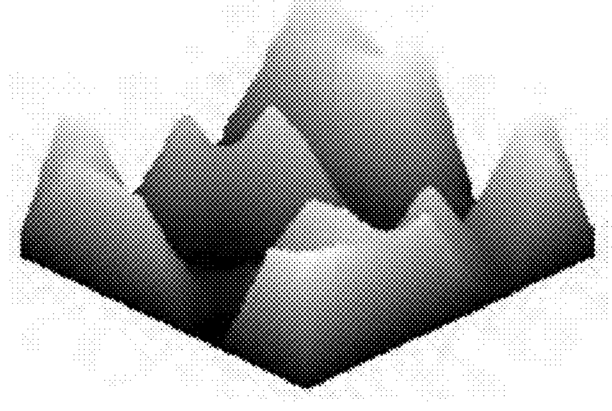

FIGS. 7F and 7G show the same box plot data as FIGS. 7B and 7C, respectively, but with the foregoing-described superimposed and introduced artifacts. That is, FIGS. 7F and 7G show the chess field and box plots of the is disturbed electrogram signals corresponding to frame 60. After filtering and normalization in step 210, the original rotor structure shown in FIG. 7A once again becomes visible in FIG. 7H following completion of the main second step 240 of the method.

Figures 7I, 7J:
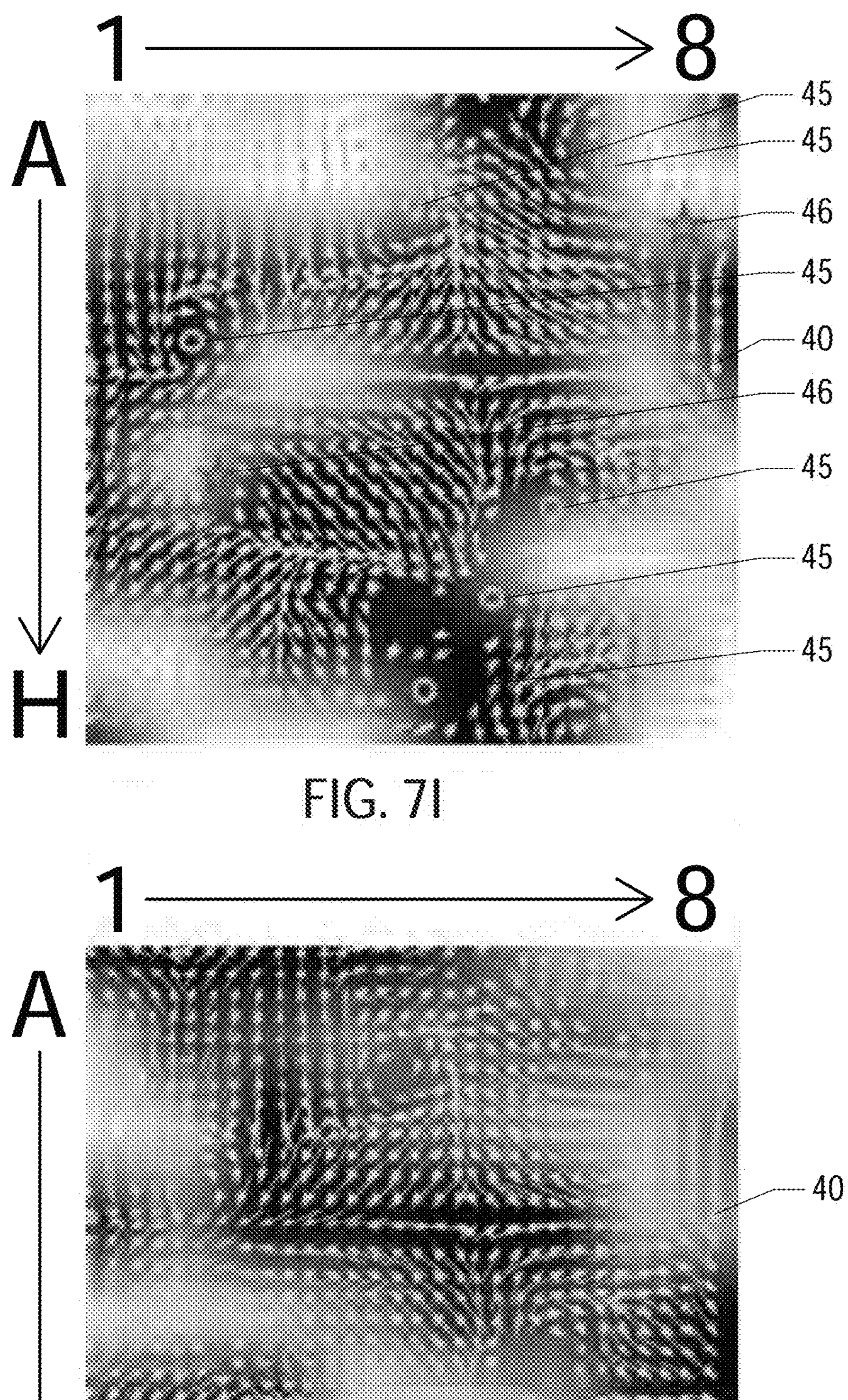

Upon applying smoothed surface calculations and fitting (as shown in FIG. 7I), method 200 is seen to detect only five of the seven active rotors shown in FIG. 7A. One additional active rotor, however, was detected at a different location (see FIG. 7I).

The largest variation in results was seen at positions where the introduction of the artifacts and noise reduced relative amplitude values by the greatest amount, as indicated by the white areas shown in FIG. 7J. The white areas shown in FIG. 7J were generated by using the sliding-window amplitude-adjusted electrogram signal techniques described above, where electrograms processed using sliding-window techniques were used to generate the image background (including the white areas) shown in the velocity vector map of FIG. 7J. The white areas in FIG. 7J thus correspond to low amplitude areas potentially indicative of valve defects or artifacts, loose electrode contact, and/or areas of fibrosis in the patient's myocardium. It is important to point out that the low-amplitude areas shown in white in the various velocity vector maps presented herein are not calculated using Green's function or optical flow data processing techniques. Instead, and as described above, these low-amplitude regions or areas may be detected by assessing the relative amplitudes of electrogram signals in step 210.

In the white areas of FIG. 7J, the resulting velocity vector map shows that the active rotors indicated therein are slightly moved closer together than in FIG. 7I, and on the left center side of FIG. 7J two rotors appearing in FIG. 7I are revealed as a single active rotor n FIG. 7J. FIGS. 7A through 7J show that there are limits to the resolution that can be achieved using a conventional 8×8 array of sensing is electrodes in a basket catheter having standard inter-electrode spacing. Thus, higher electrode densities and more recording channels could increase the resolution and accuracy of the results obtained using method 200.

After confirming that method 200 was capable of detecting complex rotor structures accurately in a patient's myocardium—even in the presence of strong artifacts and noise—method 200 was applied to different time portions of the actual patient data shown in FIG. 5B so as to test further the method's efficacy and accuracy. A velocity vector map corresponding to data acquired between 4,700 milliseconds and 5,100 milliseconds in the original EP recording of FIG. 5B is shown in FIG. 8A.

Figure 8A:
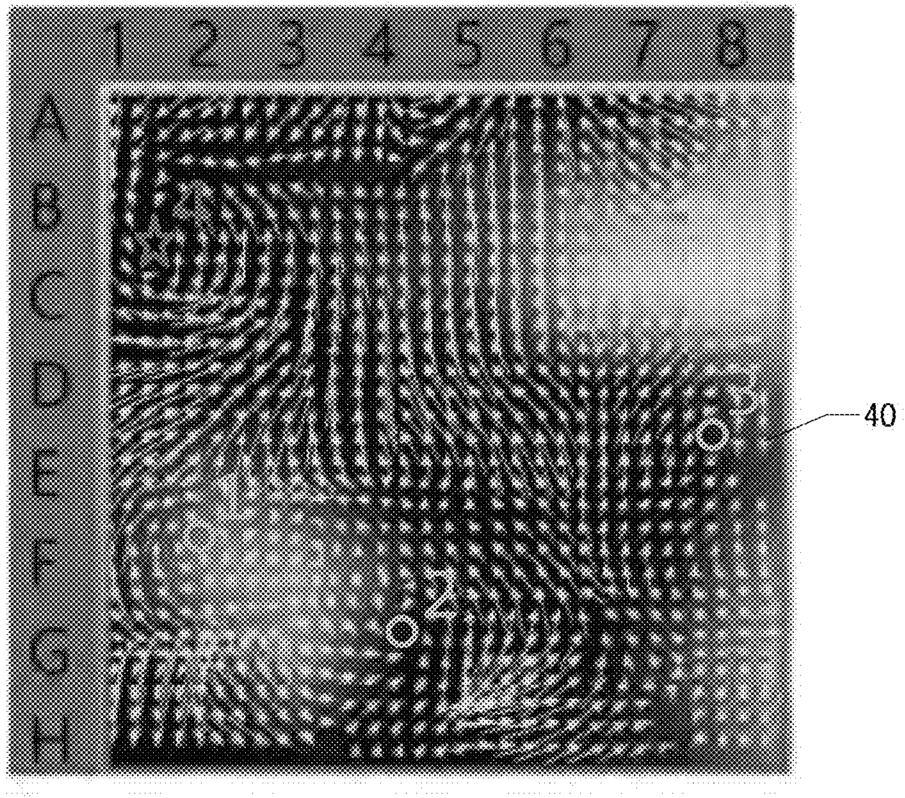
FIGS. 8A and 8B show velocity vector maps generated from actual patient data using different time windows and method 200.

As shown in FIG. 8A, four rotors indicated by circles 1, 2 and 3 and a star 4 were detected. Circles 1 and 2 in FIG. 8A appear to denote active rotors that are interacting with one another. Circle (3) in FIG. 8A may be an active rotor, but exhibits some centripetal components. Star 4 in FIG. 8A clearly corresponds to a passive rotor. Next, a velocity vector map corresponding to the same data set for data acquired between samples 0 seconds and 400 milliseconds was generated, the results of which are shown in FIG. 8B.

Figure 8B:
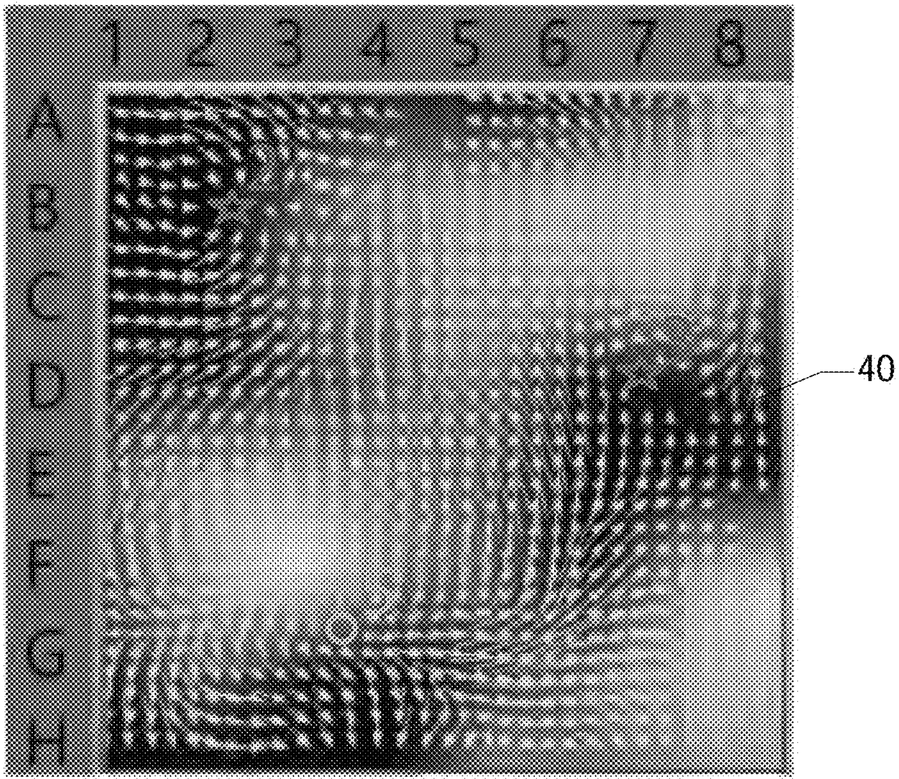

Differences between the results shown in FIGS. 8A and 8B permit a deeper insight into the true rotor structure of this patient's myocardium, as best shown in FIG. 8B. In the earlier time interval (0 msec to 400 msec) of FIG. 8B, the two associated rotors 1 and 2 shown in FIG. 8A are not yet active, while there is only a single active rotor 5 in FIG. 8B located between the positions of rotors 1 and 2 shown in FIG. 8A. Rotors 1 and 2 in FIG. 8B show up at slightly different positions, but now appear clearly as passive rotors representing likely turbulences generated at the border of a mitral valve artifact.

Thus, a health care professional can select differing time windows over which to apply method 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector maps generated by method 200 permit a health care professional to identify such cardiac rhythm disorders in a patient's myocardium with a degree of precision and accuracy that has heretofore not been possible using conventional EP mapping and intravascular basket or spline catheter devices and methods.

Figure 9:
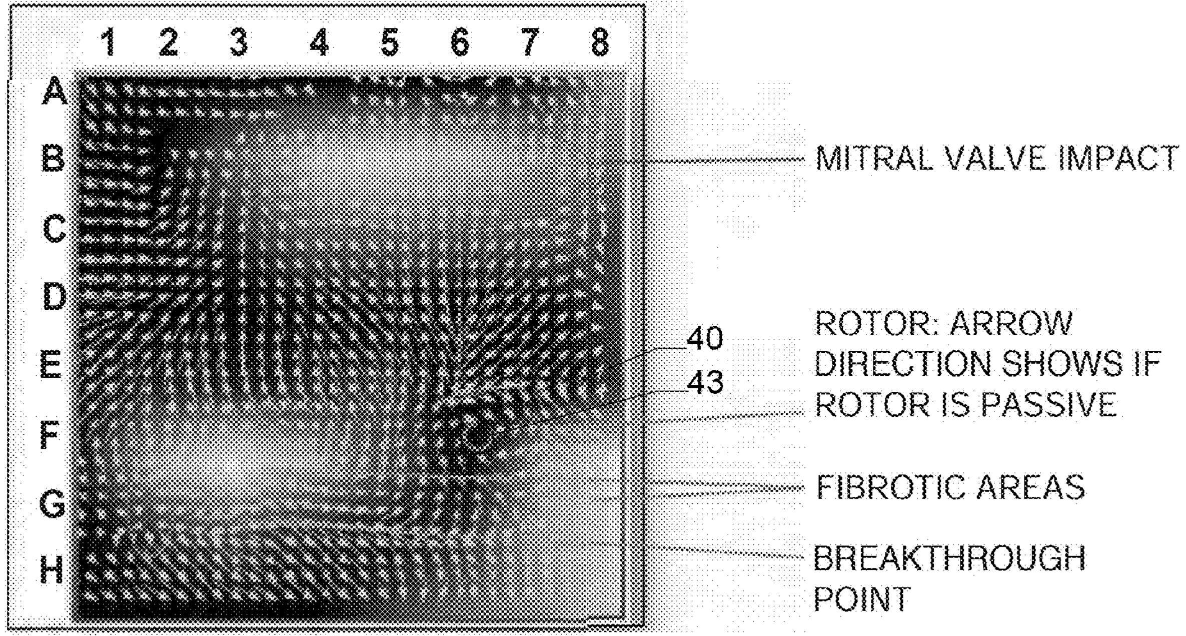
FIG. 9 shows another vector velocity map generated from actual patient data using of method 200.

Referring now to FIG. 9, there is shown another example of a vector velocity map generated from actual patient data using method 200. In FIG. 9, arrows 40 correspond to action potential wavefront velocity vectors, which as illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom right of FIG. 9 by green circle 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Figure 10A:
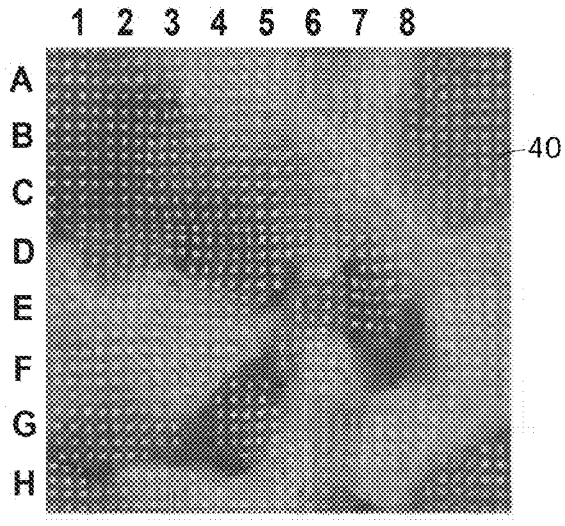
FIGS. 10A through 10D show further results obtained using actual patient data.
Figure 10B:
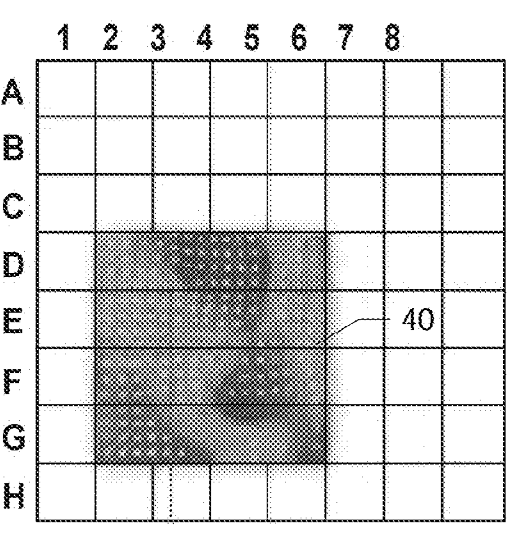
Figure 10C:
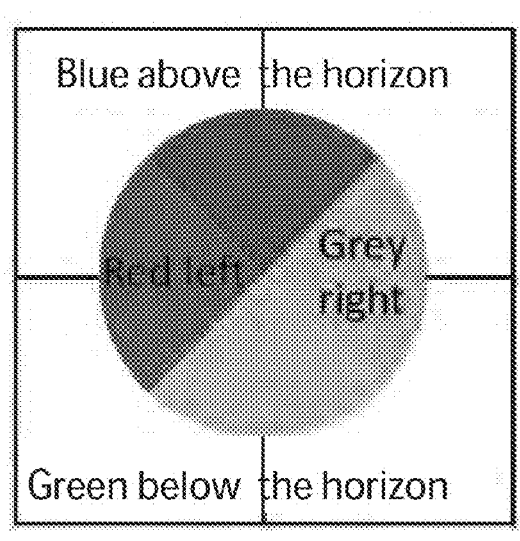
Figure 10D:
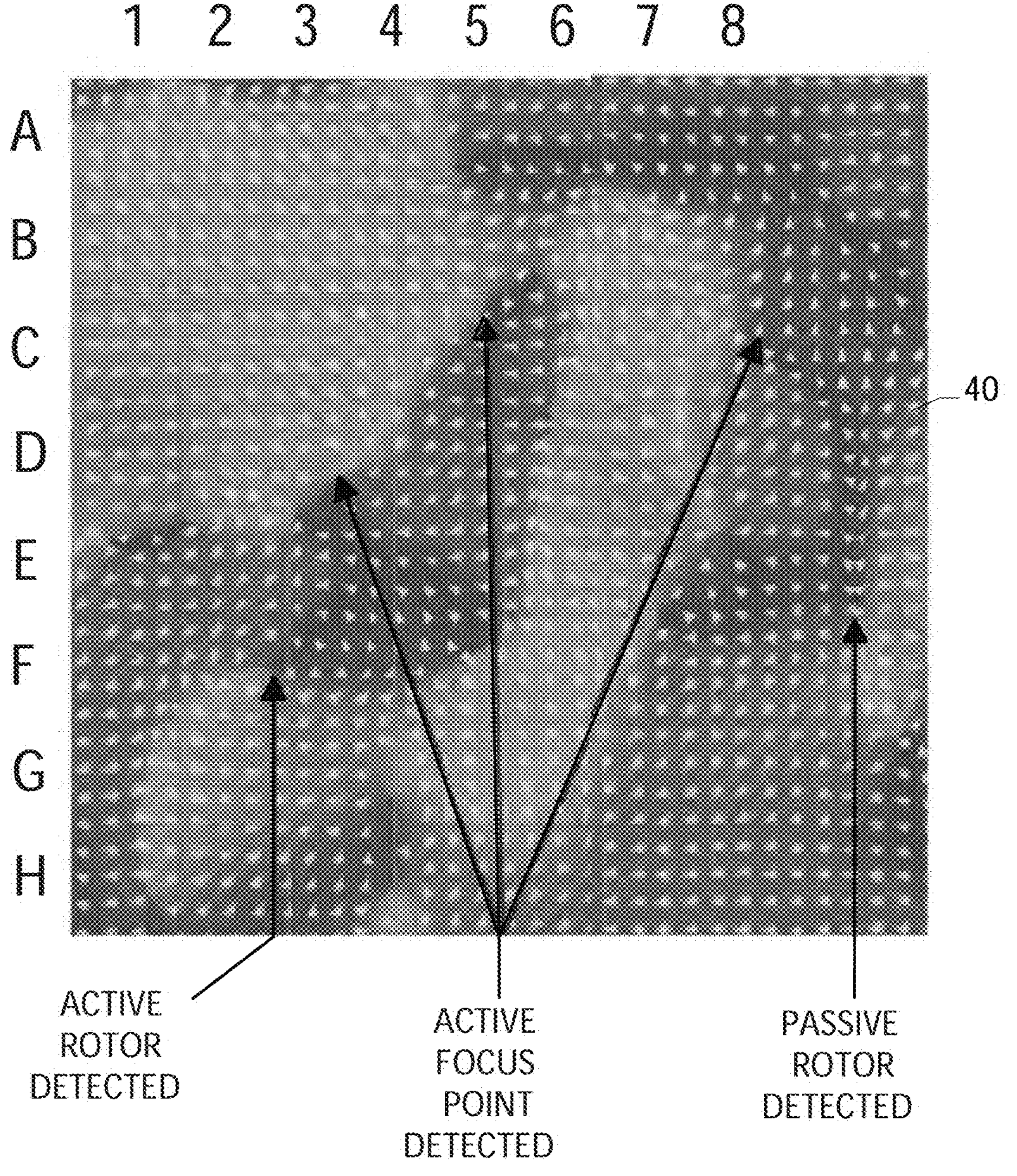

Referring now to FIGS. 10A through 10D, there are shown further results obtained using actual patient data. The raw data corresponding to FIGS. 10A through 10D were acquired from a single patient's right atrium using a 64-electrode basket catheter and corresponding EP mapping/recording system. Data were acquired at a 1 millisecond rate over a time period of 60 seconds in all 64 channels. FIGS. 10A and 10B correspond to one selected 2 second time window, and FIG. 10D corresponds to another time window from the same data set. FIG. 10D shows the color-schemes employed in FIGS. 10A, 10B, and 10D.

The vector velocity map of FIG. 10A generated using method 200 clearly reveals an active rotor located at chess board position DIE, 2/3. The vector velocity map of FIG. 10B was also generated using method 200, but using data acquired from only 16 electrodes in grid D-G, 2-5. As shown in FIG. 10B, the active rotor evident in FIG. 10A is nearly equally evident in FIG. 10B despite the significantly sparser data grid employed to produce the velocity vector map. These remarkable results obtained using a sparse electrode grid are due in large part to the robustness, stability and accuracy of method 200, as it has been applied to electrographical flow problems.

FIG. 100 shows another example of results obtained using method 200 and EP mapping data obtained from the same patient as in FIGS. 10A and 10B, but over a different time window. Note also that FIG. 10D shows that method 200 has successfully detected one active rotor (at chess board location F2/3), three active focus points, and one passive rotor (at chess board location F8).

It will now be seen that method 200 provides not only rotational direction information, but also provides high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of method 200 permits such shifts in rotor location to be detected.

In some embodiments, and as described above, multiple or different types of EP mapping and ablation catheters can be used sequentially or at the same time to diagnose and/or treat the patient. For example, a 64-electrode CONSTELLATION basket catheter can be used for EP mapping in conjunction with a PENTARAY16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in method 200 to provide enhanced estimates of the locations of the electrodes in the representations, maps or grids generated thereby, which in turn increases the accuracy and efficacy of the resulting velocity vector maps generated in method 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300. According to such a configuration, computing device 300 and data acquisition device 140 can remain galvanically isolated from one another, and the need to physically swap USB memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

In method 200, electrogram signals and processed data may be delivered or communicated to system 100, e.g., via a data carrier, after they have been acquired by the electrodes and stored for later processing. The various steps is recited in the claims, and the sub-steps recited in each step, need not necessarily be carried out in the precise order in which they are recited.

The various systems, devices, components and methods described and disclosed herein may also be adapted and configured for use in electrophysiological mapping applications other than those involving the interior of a patient's heart, more about which is said below. These alternative applications can include internal or external EP mapping and diagnosis of a patient's epicardium or other portions of the patient's heart, a patient's spinal cord or other nerves, or a patient's brain or portions thereof.

Referring now to FIGS. 1A through 10D, and also referring to the foregoing portions of the specification, it will now be seen that various embodiments of EGF techniques, methods, systems, devices, and components are described and disclosed herein, which can be employed to reveal the locations of sources of cardiac rhythm disorders in a patient's heart, including, but not limited to, rotors and sources that cause or contribute to AF.

Moreover, note that the various data processing steps described and disclosed above explicitly in connection with FIGS. 1A through 10D in furtherance of providing useful EGF results can be carried out using numerous permutations, combinations, variations, adaptations, and modifications, and signal conditioning and/or filtering techniques, which though they may not be specifically or explicitly mentioned in the specification hereof, are nonetheless contemplated and fall within the spirit and scope of the various inventions described and disclosed herein. By way of example, a variety of two-dimensional digital filtering, image filtering, and/or digital signal processing (DSP) techniques are also contemplated that may be employed in one or more the data conditioning and/or processing steps disclosed and described above, such as phase correlation, block-based methods, motion estimation, measuring visual motion, autocorrelation, cross-correlation, convolution, deconvolution, adaptive deconvolution, wavelet deconvolution, source deconvolution, and/or median filtering. By way of further example, at least some of these alternative signal processing techniques may be used to effect or aid in surface and/or data grid processing steps, and/or optical flow processing steps.

Referring now to FIGS. 11A through 13B, there are shown and illustrated various aspects of extracorporeal or body surface electrode EGF systems, devices, components, and methods, which may be employed, by way of non-limiting example, to pre-screen AF patients as described above, or as diagnostic tools for determining whether a patient has AF or AT before more complicated, involved, invasive, and/or time-consuming procedures might be employed (e.g., employing an intra-cardiac basket catheter to map a patient's atrium).

Figure 11A:
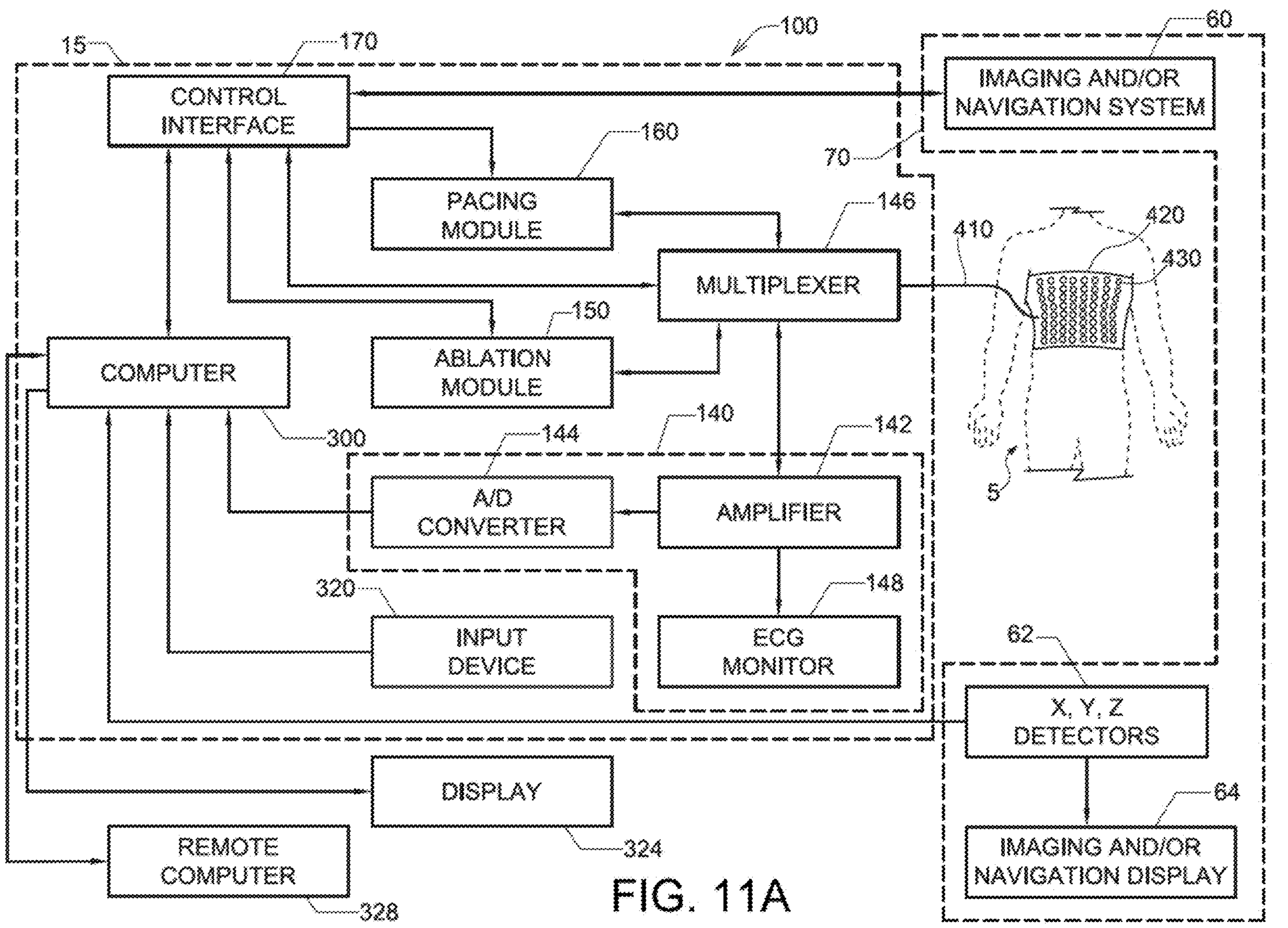
FIGS. 11A and 11B illustrate two different embodiments of a combined extracorporeal body surface electrode EGF and/or cardiac electrophysiological mapping (EP), pacing and ablation system 100.
Figure 11B:
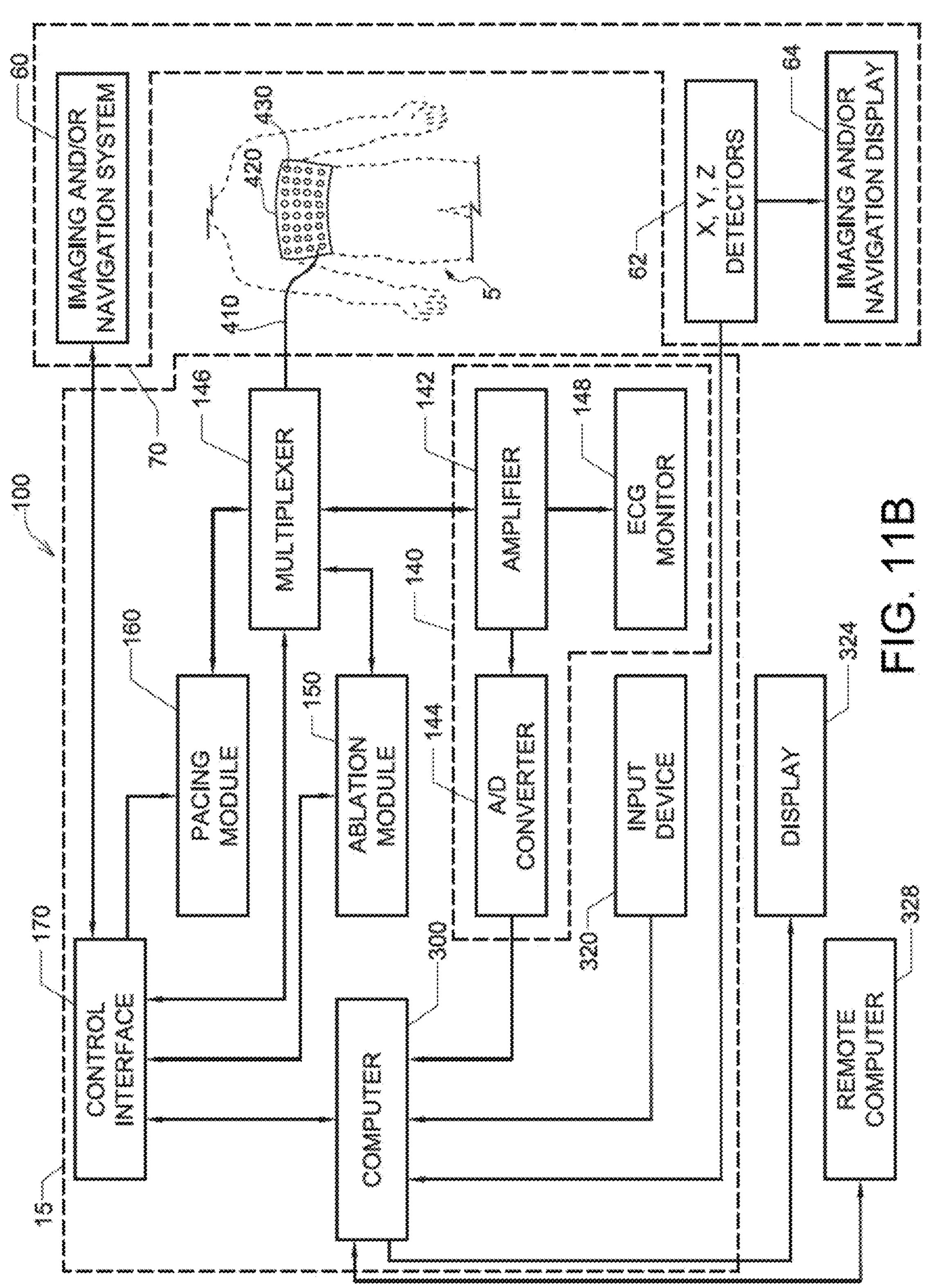

FIGS. 11A and 11B illustrate two different embodiments of a combined extracorporeal body surface electrode EGF and/or cardiac electrophysiological mapping (EP), pacing and ablation system 100. System 100 shown in FIGS. 11A and 11B shares many aspects and features with system 100 shown in FIG. 1A, where certain portions thereof may be interchanged, such as, by way of example, intra-cardiac pacing or ablation catheter 110 with external extracorporeal electrode vest 420, or may be removed, such as, by way of example, ablation module 150, pacing module 160, etc., depending of course on the particular application at hand. There is no need to repeat all the descriptions of the portions of systems 100 and 300 that are described above in connection with FIGS. 1A and 18, but that are shown in FIGS. 11A and 11B.

In FIGS. 11A and 11B there is shown a patient 5 wearing a body surface electrode vest 420 comprising a plurality of body surface electrodes 430, which are operably connected through electrical connection 410 to multiplexer 146, and thence to modules 140 and 300. Body surface electrodes 430 are configured to sense ECGs or body surface electrogram signals originating from the patient's heart. Module 140 is configured to receive such ECGs or electrogram signals through electrical connection or cable 410, and to condition such signals for further processing by computer 300. In some embodiments, electrical connection or cable 410 is replaced by a wireless connections, such as BLUETOOTH® connection.

In FIG. 11A, there are shown 64 body surface electrodes 430 mounted on the anterior portion of vest 420, which in turn is worn on or attached to the thorax of patient 5. In some embodiments, another 64 body surface electrodes 430 may be mounted on the posterior surface of vest 420 (not shown in FIG. 11A). Other numbers and configurations of body surface electrodes are also contemplated, such as individual patches, multiple or interconnected patches, patches and electrodes configured to cover only certain tailored portions of a patient's torso determined, calculated, or known to provide locations for sensing optimum heart signals, and numbers of electrodes ranging, by way of non-limiting example, between 1 electrode and 3 electrodes, 4 electrodes, 8 electrodes, 12 electrodes, 16 electrodes, 24 electrodes, 36 electrodes, 48 electrodes, 64 electrodes, 72 electrodes, 96 electrodes, 128 electrodes, 256 electrodes, 512 electrodes, and 1,024 electrodes.

Some examples of current manufacturers of cardiac monitoring patches include: (a) iRhythm® and their Zio XT® and Zio AT® Patch product offerings; (b) the Bardy Dx® Carnation Ambulatory Monitor (CAM™), and (c) the NUVANT® Mobile Cardiac Telemetry (MCT) Monitor, which communicates wirelessly with a cellular device. See, for example: (1) U.S. Pat. No. 10,123,703 entitled "Health monitoring apparatus with wireless capabilities for initiating a patient treatment with the aid of a digital computer" to Bardy et al. ("the '703 patent"); (2) U.S. Pat. No. 10,299,691 entitled "Wearable monitor with arrhythmia burden evaluation" to is Hughes et al. ("the '691 patent"); (3) U.S. Pat. No. 10,772,522 entitled "Disposable biometric patch device" to Zadig, and (4) "Cardiac Ambulatory Monitoring: New Wireless Device Validated Against Conventional Holter Monitoring in a Case Series" to Murali et al., Front. Cardiovasc. Med., 30 Nov. 2020 (https://doiLorg/10.3389/fcvm.2020.587945) describing the SmartCardia® wearable cardiac monitoring patch ("the Murali paper"). Those skilled in the art will realize that certain aspects and features disclosed and described in in the '703 patent, the '691 patent, the '522 patent, and the Murali paper can be employed in, or adapted and modified for use in, the systems, devices, components, and methods described and disclosed herein. The '703 patent, the '691 patent, the '522 patent, and the Murali paper incorporated by reference herein, each in its respective entirety. Apple iWatch®, FitBit®, Galaxy Watch3®, and Galaxy Watch Active2® are examples of watch or watch-like devices configured to acquire cardiac data from the wearer, such as ECGs, blood pressure, heart rate, etc. Such wearable devices likewise contain certain aspects and features that can be employed in, or adapted and modified for use in, the systems, devices, components, and methods described and disclosed herein.

In the example of FIG. 11B, there are shown 32 body surface electrodes 430 mounted on the anterior portion of vest 420, which in turn is worn on or attached to the thorax of patient 5. In some embodiments, by way of non-limiting example, another 32 body surface electrodes 430 may be mounted on a posterior surface of vest 420 (not shown in FIG. 11A).

Continuing to refer to FIGS. 11A and 11B, any suitable number of body surface electrodes 430 may be employed in system 100. Generally the more body surface electrodes 430 employed the better so as to improve resolution and avoid, for example, spatial aliasing of electrical signals originating from patient's heart 10 arriving at the surface of the patient's thorax. Other numbers, arrangements, configurations, and types of body surface electrodes 430 are also contemplated, however. In some embodiments, at least some body surface electrodes 430 and vest 420 are together configured to detect cardiac activation or electrical signals, and to generate electrocardiograms or body surface electrogram signals, which are then relayed by electrical conductors in cable 410 from the individual electrodes 430 to data acquisition device 140.

It is further contemplated that body surface electrodes 430 may be mounted, attached or coupled to the patient's thorax by means other than a vest, such as by patches, electrode strips, individually, or by other means known in the art. For example, electrode strips manufactured by Goltec GmbH of Cremlingen, Germany can be used. Carbon and metal body surface electrode strips are available from Goltec GmbH. Carbon electrode strips have the advantage of being radio-translucent, i.e., being transparent or substantially transparent during X-ray imaging.

Electrodes may be provided only on the anterior portion of the patient's thorax, only on the posterior portion of the patient's thorax, on side or lateral portions of the patient's thorax, or on any suitable combination of anterior, posterior and/or lateral portions of the patient's thorax.

Continuing to refer to FIGS. 11A and 11B, and as mentioned above, electrodes 430 are configured to sense electrical activity originating in patient's heart 10. In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60. Imaging and/or navigation system 60 may be employed used to help identify and determine the precise positions of the various electrodes 430 or position markers included in vest 430. Gels, adhesives, and liquids may be employed to improve electrical coupling of electrodes 430 with the patient's body, as is well known in the art.

Still referring to FIGS. 11A and 11B, electrodes 430 configured to sense electrical activity originating in patient's heart 10 may also be individual or interconnected cardiac monitoring patches, incorporated (or not) into a wearable structure such as a vest or band. Electrodes 430 may also form portions of standard or customized 1-lead ECG monitoring leads (which typically use 1 electrode on the torso), 3-lead ECG monitoring leads (which typically use 3 electrodes on the torso), 5-lead ECG monitoring leads (which typically use 5 electrodes on the torso), and/or 12-lead ECG monitoring leads (which typically use 10 electrodes on the torso and limbs). Cardiac monitoring patches and ECG monitoring leads may have electrodes attachable to a human torso, legs or other portions of the body using adhesives suitable for that purpose, and may also comprise circuitry required to telemeter or send data therefrom via BLUETOOTH or WiFi to system 100, eliminating the need for wired connections between electrodes 430 and system 100. Such circuitry may also be configured to receive instructions, data, and programs wirelessly from system 100 or another source.

In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60.

Note that in some embodiments, system 100 of FIGS. 11A and 11B may not include multiplexer 146, ablation module 150, pacing module 160, imaging and/or navigation system, 60, or other modules or components shown in FIGS. 11A and 11B. Among other things, the embodiments of system 100 shown in FIGS. 11A and 11B are configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques using body surface electrodes 430. In some embodiments, system 100 is further configured to treat the location of the source of the cardiac rhythm disorder or irregularity, for example by ablating the patient's heart at the detected source location.

The embodiment of system 100 shown in FIGS. 11A and 11B comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIGS. 11A and 11B. Computer 300 may also be operably connected to a remote computer or analytic database or server 323. At least each of components, devices, modules and systems 60, 110, 140, 146, 148, 150, 170, 300, 324 and 328 may be operably connected to other components or devices by wireless (e.g., BLUETOOTH) or wired means. Data may be transferred between components, devices, modules or systems through hardwiring, by wireless means, or by using portable memory devices such as USB memory sticks.

During body surface EP mapping or EGF analysis procedures, and as described above, body surface electrodes 430 are positioned on the thorax of patient 5, and by way of example may be mounted on a vest 420 that is configured to place individual electrodes 430 in predetermined positions on the patient's body. These predetermined electrode positions can also be provided to imaging and/or navigation system 60 and/or to computer 300 as a data file so that the spatial positions of body surface electrodes 430 are known (at least approximately), and so that EGF analysis can be carried out accordingly as described above in connection with intra-cardiac EGF analysis (e.g., as described above in connection with FIGS. 1A through 10D).

When system 100 of FIGS. 11A and 11B is operating in an EP mapping or EGF mode, body surface electrodes 430 function as detectors of electrocardiographic signals. In one embodiment, the analog signals obtained from body surface electrodes 430 are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, EGF analysis and graphical display (as described above).

Note that in some embodiments of system 100 shown in FIGS. 11A and 11B, and as described above, multiplexer 146 may not form a portion of system 100, In addition, in some embodiments computing device 300 may be combined or integrated with one or more of data acquisition device 140, ablation module 150, and/or pacing module 160.

Figure 11C:
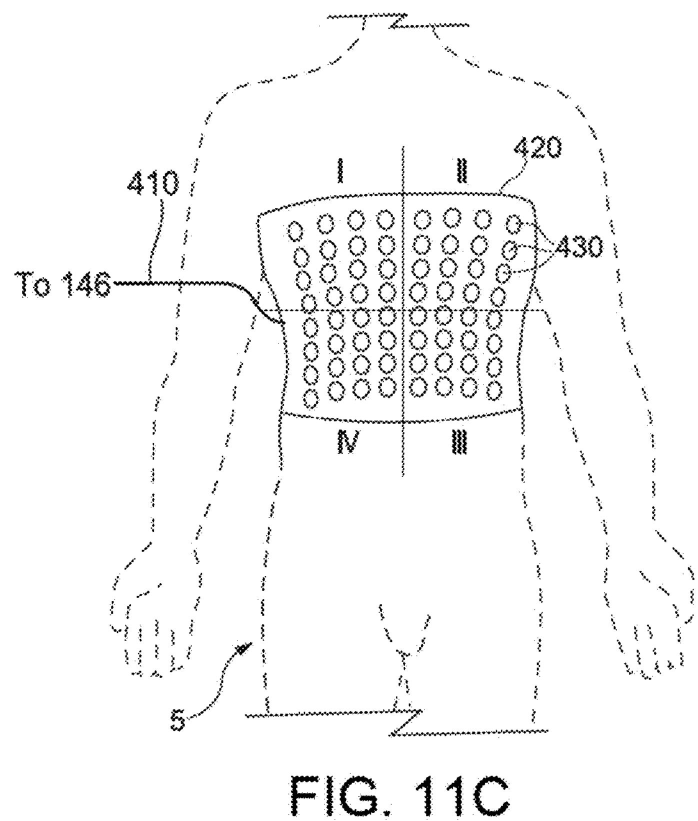
FIGS. 11C and 11D show respective anterior and posterior views of a patient's thorax with vest 420 worn on or attached thereto.
Figure 11D:
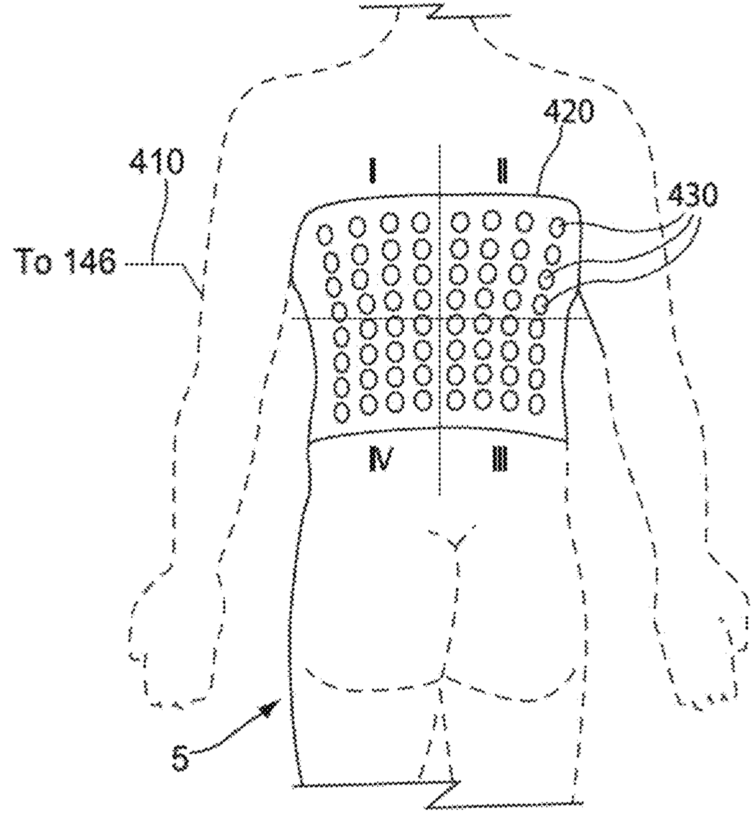

Referring now to FIGS. 11C and 11D, here are shown respective anterior and posterior views of patient 5's thorax with vest 420 worn on or attached thereto. Quadrants I, II, III, and IV are shown in each of FIGS. 11C and 11D, which delineate quadrants into which electrodes 430 fall. Some quadrants or portions of such quadrants may be more useful or suitable than others for purposes of acquiring body surface electrogram signals of sufficient fidelity that correspond to the patient's right or left atria, for example, or to any other portion of the patient's heart which is desired to analyzed using EGF or EP mapping techniques. See, for example, "Detailed Anatomical and Electrophysiological Models of Human Atria and Torso for the Simulation of Atrial Activation" to Ferrer et al, PLOS One, Nov. 2, 2015, DOI:10.1371/journal.pone.0141573 (hereafter "the Ferrer reference"), the entire disclosure of which is hereby incorporated by reference herein pursuant to an Information Disclosure Statement filed on even date herewith containing a complete copy of such publication. See also "Body surface localization of left and right atrial high-frequency rotors in atrial fibrillation patients: A clinical-computational study" to Rodrigo et al., *Heart Rhythm*, September, 2014, 11(9): 1584-1591, doi:10.1016/j.hrthm.2014.05.013 (hereafter "the Rodrigo reference"), the entire disclosure of which is hereby incorporated by reference herein pursuant to an Information Disclosure Statement filed on even date herewith containing a complete copy of such publication.

By way of non-limiting example, body surface electrodes 430 may be clustered or more densely positioned on those portions of a patient's thorax that are expected to yield, or that are measured to yield, the best or optimum fidelity body surface electrogram signals corresponding to signals originating in a patient's atrium, the two atria, or any other target portion of the patient's heart 10 that is to be analyzed. For example, body surface electrodes 430 can be concentrated on the anterior portion of the patient's thorax in the region where quadrants I, II, III and IV intersect near the middle of the thorax, or at a location slightly upwards from, or slightly upwards and to the left from, such intersection. Note that electrodes 430 can be arranged on the patient's thorax in any suitable pattern or configuration, including, but not limited to, an array of rows and columns (as shown in FIGS. 11A through 11D), a rectangular array, a square array, a circular or elliptical array, a cross-shaped array, a star-shaped array, and/or an array with varying electrode density or spacing where electrode spacing is finest in a region of maximum interest and least in a region of less interest. As body surface electrode data from a patient's thorax are analyzed using EGF techniques and/or machine learning techniques (more about which is said below), the locations of electrodes 430 on patient's thorax 5 may also be changed or adjusted so that body surface electrogram signals of the highest fidelity and/or lowest noise are acquired by system 100.

In one embodiment, body surface electrogram signal data are processed by computer 300 to produce a display showing the location(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to select interactively and quickly the electrodes 430 of vest 420 that are best detecting the location of the source(s) of the cardiac rhythm disorder or irregularity. Note that in some embodiments, EGF techniques are utilized to analyze body surface electrogram signal data without having to resort to complicated, lengthy and computationally-intensive tomographic or reverse modelling computations. In some applications, all that is required is to determine whether sources of AF and/or AT are present in a patient's atrium or atria, and whether those sources are stable or unstable. In other embodiments, and assuming sufficient computational power is available to process the acquired body surface electrogram signals, reverse modelling (e.g., "solving the reverse problem"), downward continuation, and/or employing tomographic techniques using a three-dimensional grid of voxels may be employed to yield higher fidelity and more accurate EGF results.

Referring once again to FIGS. 11A and 118, EP mapping system or data acquisition device 140 is configured to condition the analog body surface electrogram signals delivered by electrodes 430 to amplifier 142. Conditioning of the analog body surface electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

In some embodiments, the rate at which individual body surface electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM® PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN® amplifier, which is configured to amplify and condition electrocardiographic signals of biologic origin and pressure transducer input, and transmit such information to a host computer (e.g., computer 300 or another computer).

Computing device or computer 300 is suitably configured and programmed to receive or access the body surface electrogram signals provided by body surface electrodes 430. Computer 300 is further configured to analyze or process such electrogram signals in accordance with the methods, functions and logic disclosed and described herein so as to permit reconstruction of cardiac activation information from the electrogram signals using EGF techniques. This, in turn, makes it possible to locate with at least some reasonable degree of precision the location of the source of a heart rhythm disorder or irregularity. Once such a location has been discovered—or not discovered—the characteristics of the source(s) may be analyzed and the therapy, if any, that is to be delivered to the patient may be determined.

In one embodiment, and as shown in FIGS. 11A and 11B, system 100 may also comprise a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snapshot" pictures of the heart 10 of a patient (body not shown). A picture image is detected by a detector 62 along each axis of imaging, and can include a silhouette of the heart as well as a display of the positions of body surface electrodes 430 on the patient's thorax (more about which is said below), which is displayed on imaging or navigation display 64. Digitized image or navigation data may be provided to computer 300 for processing and integration into computer graphics that are subsequently displayed on monitor or display 64 and/or 324.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC®=STEALTHSTATION® system).

Figure 12:
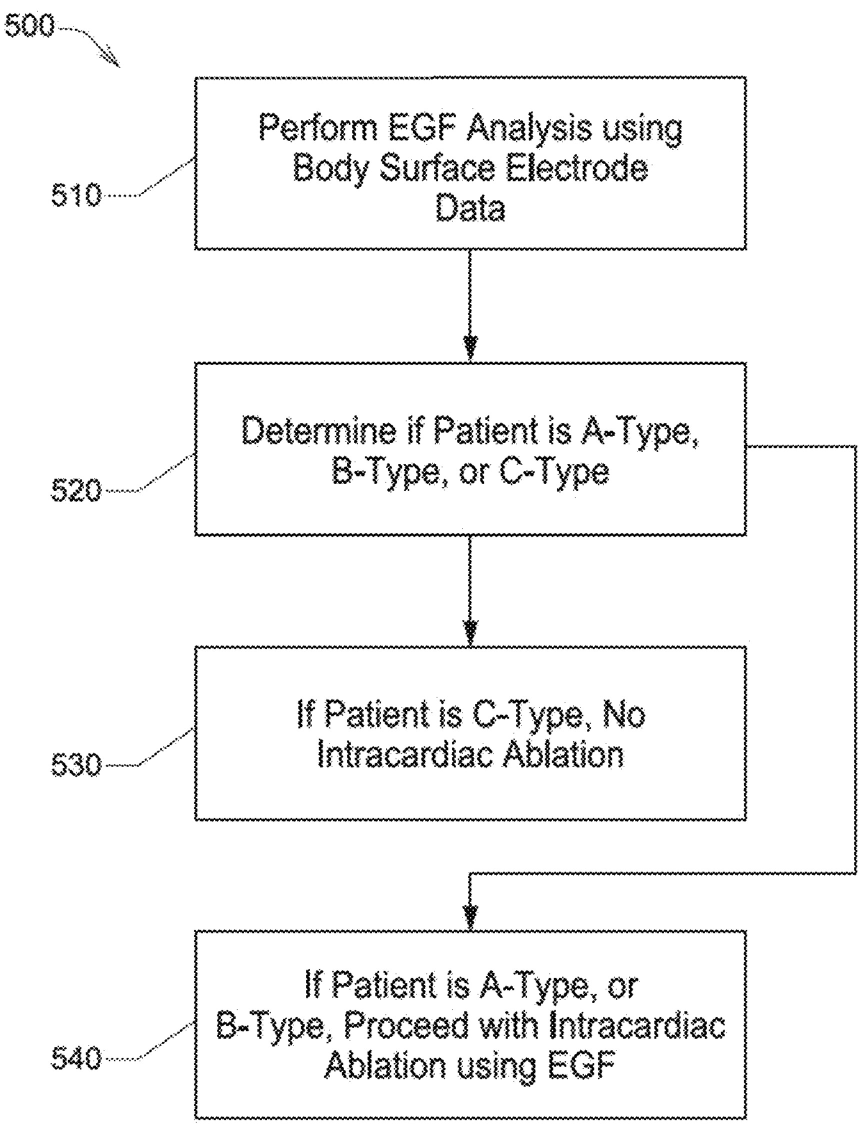
FIG. 12 shows a generalized method 500 of employing EGF techniques in conjunction with body surface electrodes 430.
Figure 12B:
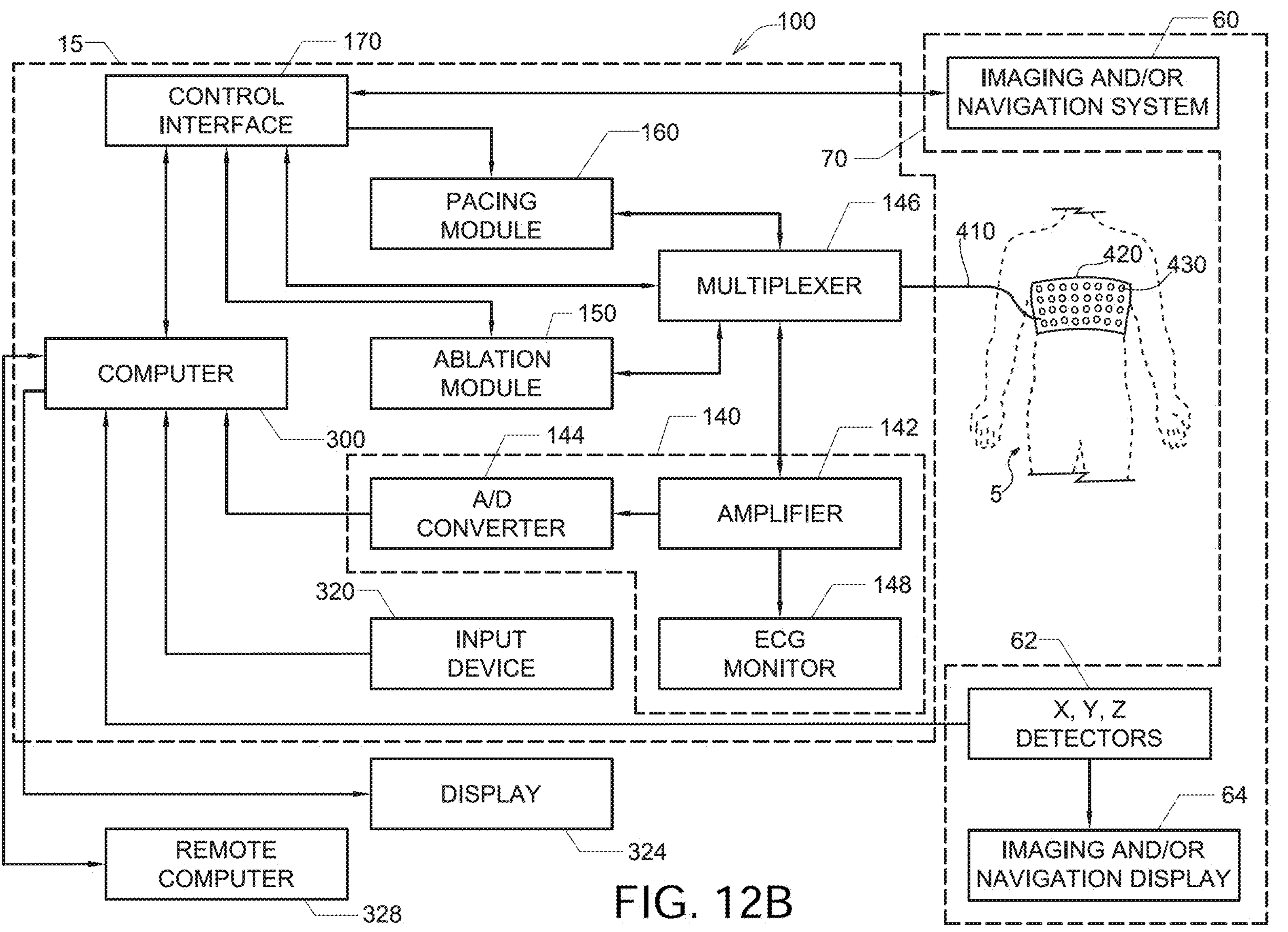
Figure 12C:
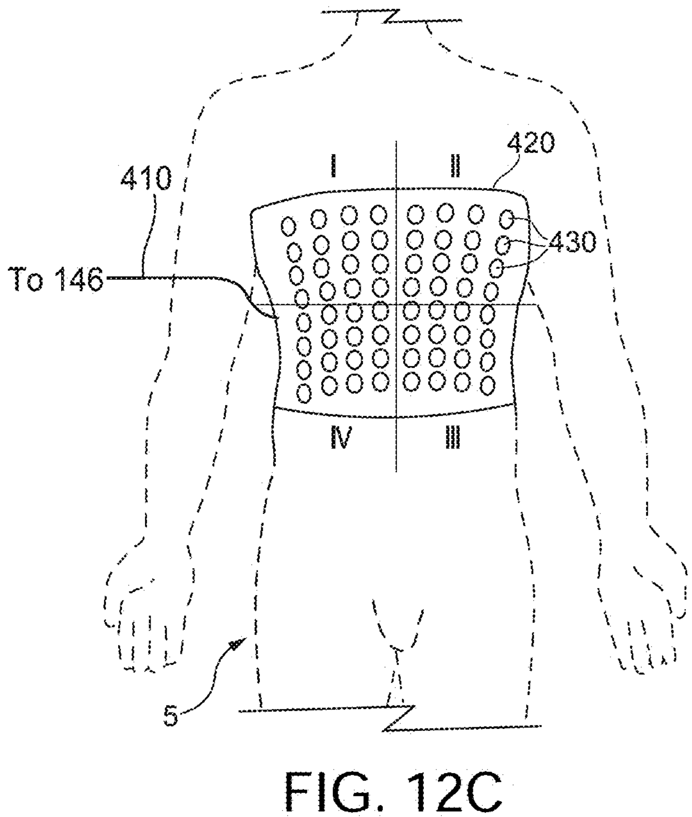
Figure 12D:
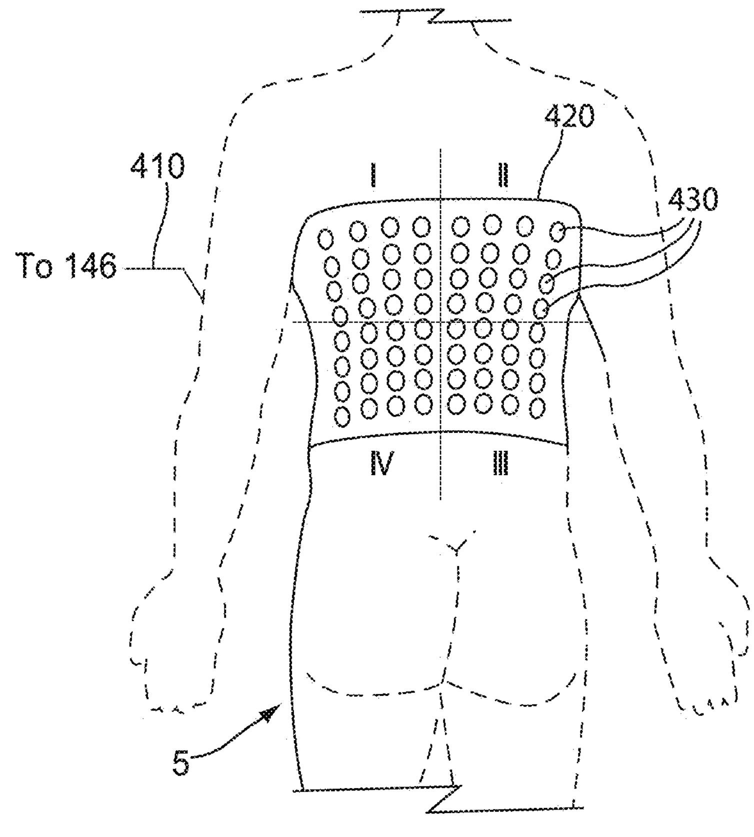

Referring now to FIG. 12, there is shown one embodiment of a generalized method 500 of employing EGF techniques in conjunction with body surface electrodes 430 to permit patients to be classified as A-type, B-type or C-type patients, which method comports with the EGF patient classification discussion set forth above. At step 510, EGF analysis is performed on body surface electrode data that have been acquired from a patient using, by way of non-limiting example, system 100 of FIG. 11A or 11B. EGF analysis can be carried out in accordance with the teachings set forth above that relate to, or are described in connection with, FIGS. 1 through 10D. In step 520, it is determined whether the patient is an A-type patient, a B-type patient, or a C-type patient, using EGF techniques (such as those described above in connection with FIGS. 7A through 7J). If the patient is determined to be an A- or B-type patient, intra-cardiac ablation of the detected source(s) can be carded out at step 540 with the benefit of the EGF techniques described in detail above. If the patient is determined to be a C-type patient at step 520, no intra-cardiac ablation is carried out at step 530, although PVI for that patient may be well advised depending on the EGF results. After having read and understood the present specification and drawings, those skilled in the art will understand that many variations, combinations, and permutations of method 500 are possible.

Figure 13A:
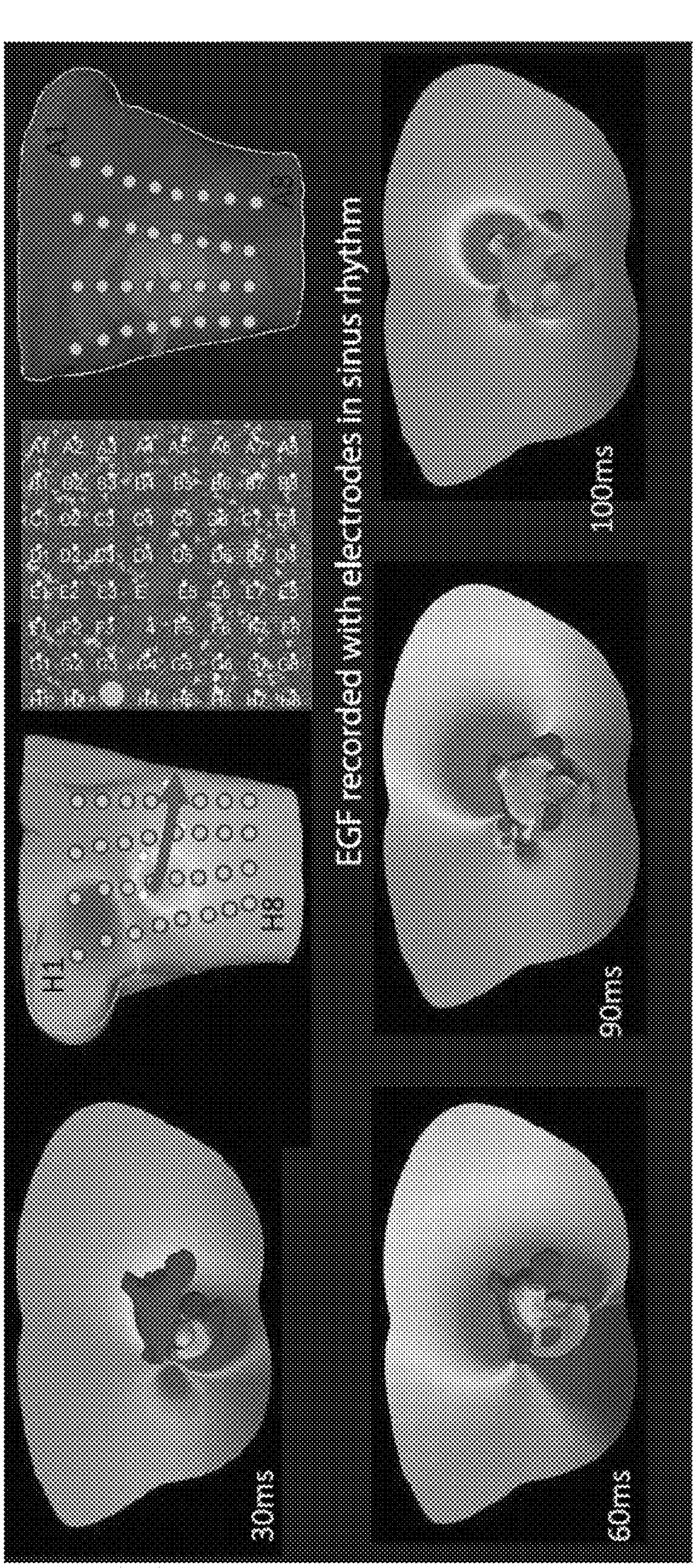
FIGS. 13A and 13B show examples of EGF analysis carried out using body surface electrodes 430 and EGF techniques
Figure 13B:
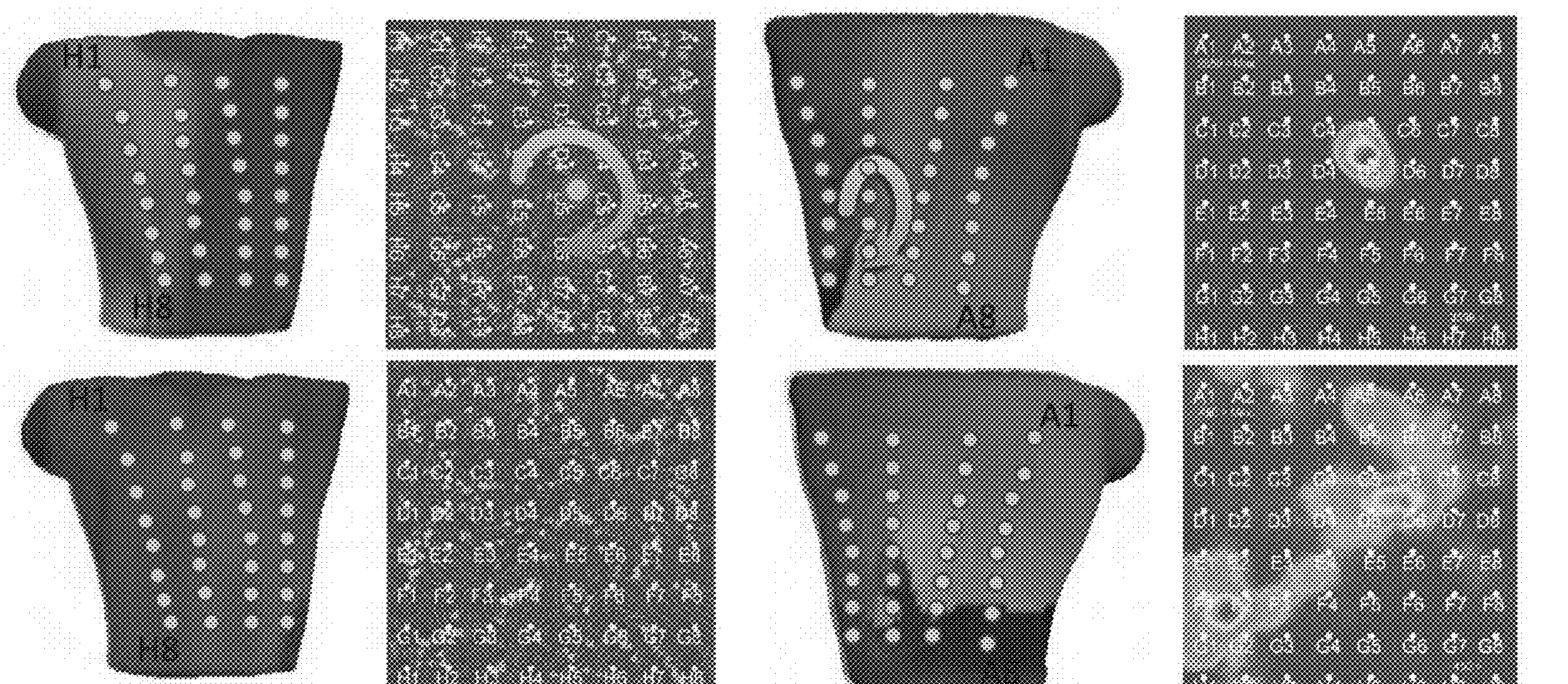

FIGS. 13A and 13B show examples of EGF analysis carried out using body surface electrodes and EGF techniques. In FIG. 14A, simulated electrical potential wave propagation from the heart to and across body surface electrodes is illustrated for calculated potential distributions occurring as a normal sinus rhythm P-wave propagates from its source outwardly to 30 msec, 60 msec, 90 msec, and 100 msec. EGF results obtained with surface body electrodes are shown in the upper right central portion of FIG. 13A, where no AF source is indicated or detected. In FIG. 13B, simulated electrical potential wave propagation from the heart to and across body surface electrodes is illustrated for calculated potential distributions occurring in a patient with AF. EGF results obtained from simulated body surface electrodes are shown in the four EGF panels of FIG. 13B, where an AF source is clearly indicated and has been detected. FIGS. 13A and 13B show body surface potential distributions sharing some similarities to those discussed above in the Ferrer and Rodrigo references.

Figure 14:
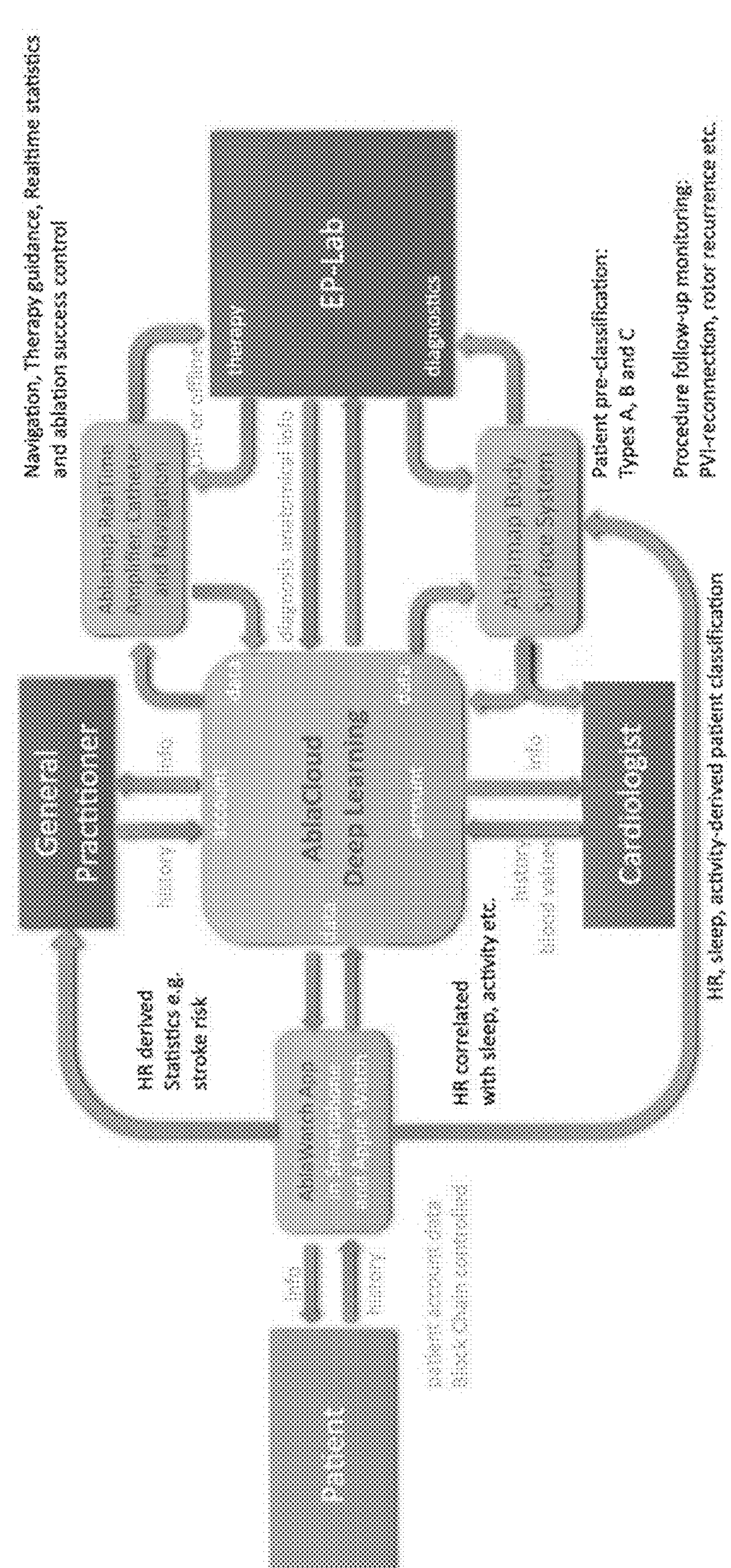
FIG. 14 shows some benefits accruing to one embodiment of an ABLACON EGF analysis system 700.

FIG. 14 shows some benefits accruing to one embodiment of an ABLACON EGF analysis system 700. As shown in the embodiment of FIG. 14, system 700 comprises patient 715, ABLAWATCH app 713, general practitioner 701, ABLAMAP amplifiers, catheters, and navigation systems 703, EP-Lab 705, ABLACLOUD deep learning 711, ABLAMAP body surface system 707, and cardiologist 709. Benefits 720 ("Keep patient safe and informed"), 730 ("Evaluate stroke risk, therapy success forecast, and AF burden (outcome)"), 740 ("Hit extra PV targets"), and 750 ("Avoid needless ablations") arise from use of EGF technology when employed in the integrated and holistic manner illustrated in FIG. 14. In system 700, one or more central servers and the internet can be employed to collect, analyze and disseminate or distribute the various types of information shown in FIG. 14. See, for example, "Association of Atrial Fibrillation Clinical Phenotypes With Treatment Patterns and Outcomes: A Multicenter Registry Study" to Taku Inohara et al., JAMA Cardiol. 2018; 3(1):54-63, the entirety of which is hereby incorporated by reference herein. Embodiments of system 700 other than that shown explicitly in FIG. 14 are also contemplated, such as systems 700 have more or fewer elements than those shown in FIG. 14.

Figure 15:
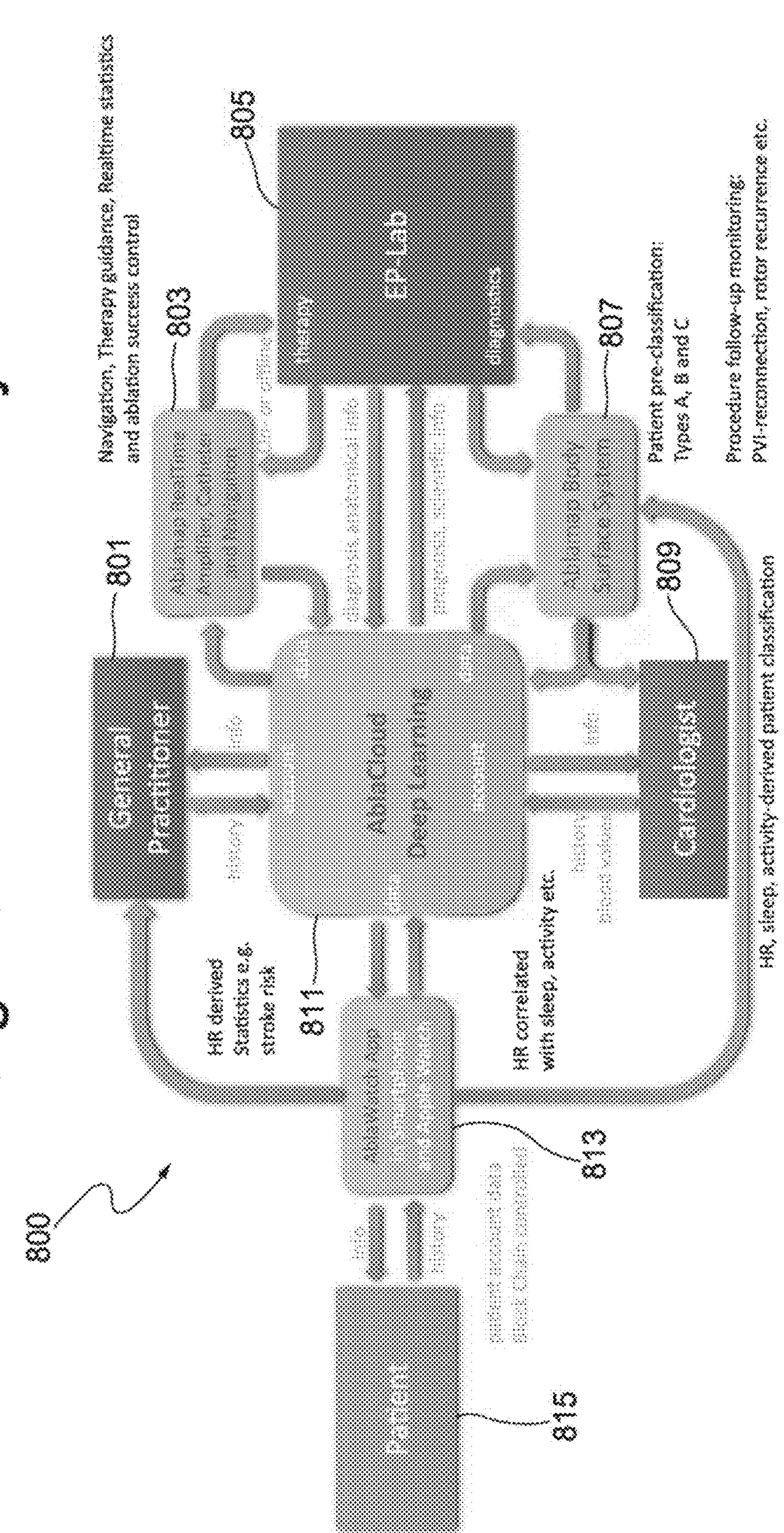
FIG. 15 shows one embodiment of an ABLACON diagnosis and treatment system 800.

FIG. 15 shows one embodiment of an ABLACON diagnosis and treatment system 800, which mirrors at least portions of system 700 shown in FIG. 14. System 800 illustrated in FIG. 15 denotes specific tasks that are carried out in, or results that are provided by, System 700 of FIG. 14 (e.g., history, HR derived statistics, HR correlated with sleep activity, etc.). The holistic and integrated systems illustrated in FIGS. 15 and 15 permit the centralized acquisition, storage, processing, and dissemination of remote information gleaned from hundreds or thousands of patients from around the world. Systems 700 and 800 are configured to permit continuous updating of EGF data and results based on anonymized patient data, and associated deep learning of the system so that EGF results can be improved and made more accurate over time. In addition, EGF results and/or raw or partially processed electrogram signal data from a particular patient can be uploaded to systems 700 and/or 800 for comparison to other data, or for the generation of a diagnosis of the data and/or therapy treatment recommendations or suggestions.

Figure 16:
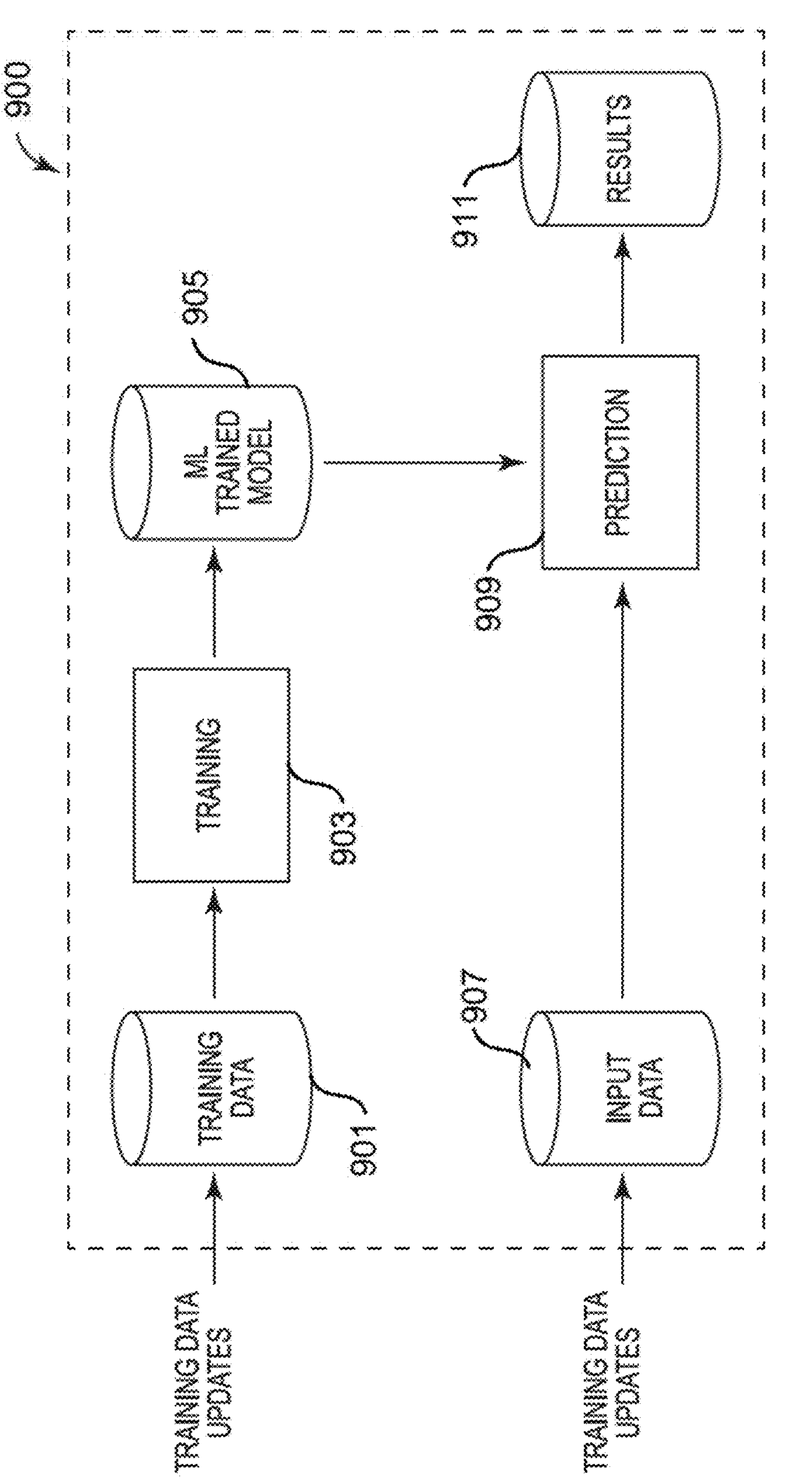
FIG. 16 shows one embodiment of a simplified machine learning system 900 and a corresponding generalized machine learning workflow.
Figure 17:
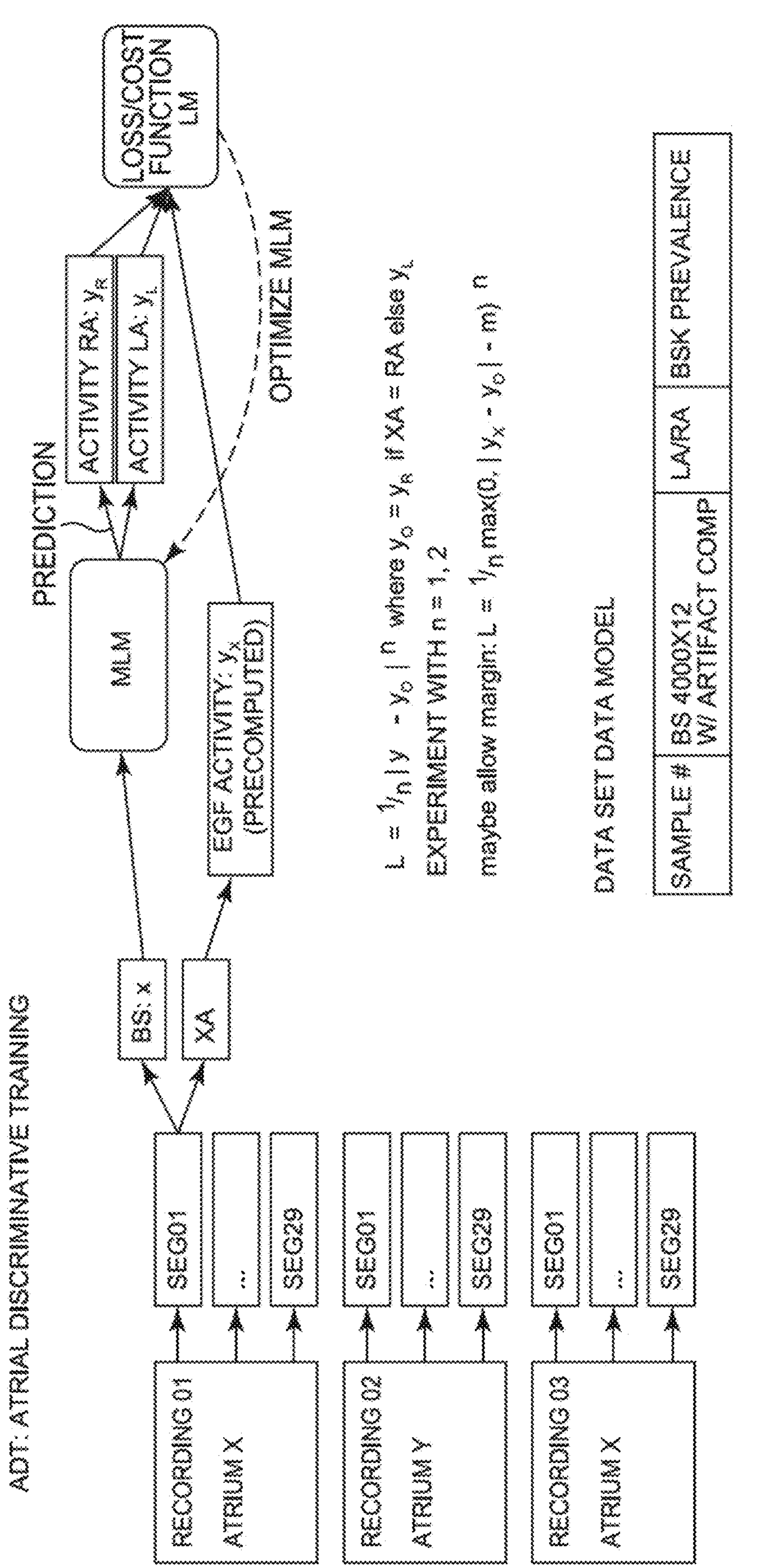
FIG. 17 shows a block diagram and data flow diagram according to one embodiment of a body surface and intracardiac electrode machine learning system that employs an atrial discriminative training (ADT) machine learning model (MLM) that works in combination with a loss or cost function module (LM)

Referring now to FIGS. 16 and 17, there are shown various aspects, features and components according to some embodiments of machine learning systems, devices, components, and methods that can be employed to leverage and enhance the benefits and advantages of the body surface electrode and EGF techniques and processes described above so that the natures and types of cardiac rhythm disorders characteristic of patients' hearts can more be more efficiently, accurately, quickly, and cost-effectively detected and diagnosed. In one such embodiment, where a trained atrial discriminative machine learning system is employed, body surface electrode data acquired from a patient serve as the inputs to the trained atrial discriminative machine learning system, which then provides as outputs predicted EGF flow fields or associated characteristics for the patient's heart and/or a predicted ABC classification of the patient's heart disorders, where such predicted outputs are based upon the body surface electrode and EGF techniques and processes described above in combination with machine learning techniques, as well as the use of intra-cardiac electrode data (more about which is said below).

FIG. 16 shows one embodiment of a simplified machine learning system 900 and a corresponding generalized machine learning workflow. Training data for system 900 initially comprises paired sets of EGF or optical flow results obtained from intra-cardiac electrode data and body surface electrode data, where such paired sets of data are acquired and recorded from the same patients at the same time. System 900 is first trained using a sufficiently large number of such sets of paired data until system 900 is capable of providing accurate optical flow predictions and/or ABC or other suitable patient classifications based upon new body surface electrode data from new patients that are provided later on as input data to system 900. System 900 is preferably configured so that it is continuously and/or periodically updated with new training data. Some generalized types of machine learning methods that can be employed in system 900 include, by way of illustrative but non-limiting example, supervised (e.g., classification or regression) methods, unsupervised (e.g., clustering and estimation of probability density function) methods, and semi-supervised learning (e.g., text/image retrieval system) methods.

Now described are more specific examples of machine learning systems, methods applied to the problem of accurately predicting the presence or classification of cardiac rhythm disorders in a patient's heart based upon input surface body electrode data only (in combination with a trained atrial discriminative machine learning model).

With reference now to FIG. 17, in one embodiment a body surface and intra-cardiac electrode machine learning system and its various components and associated methods are employed to facilitate screening of patients for atrial fibrillation. The system is configured to determine, using only non-invasive body surface electrode data, how best to treat a patient in any subsequent procedures that might be carried out, such as acquiring and analyzing intra-cardiac EP data using a basket catheter, atrial ablation, or pulmonary vein isolation. Such systems and methods may also be employed to determine whether a particular patient is a good or poor candidate for undergoing a further intra-cardiac (e.g., atrial) electrophysiological (EP) mapping diagnostic procedure and/or for an intra-cardiac atrial ablation or PVI procedure. In some embodiments, such a machine learning system and its various components and associated methods are can be used to classify patients potentially suffering from AF as A-, B-, or C-type patients.

In accordance with the teachings and disclosures set forth above and in the Figures, patients who are determined to be C-type patients using the body surface and intracardiac electrode machine learning system described and disclosed herein can be spared the trouble, risk, cost and expense associated with undergoing very likely unnecessary but expensive intra-cardiac EP mapping and/or ablation or PVI procedures that would be unlikely to do anything to improve their state of health. Further in accordance with the teachings and disclosures set forth above and in the Figures, and in contrast, patients who are determined to be A- or B-type patients using the body surface and intracardiac electrode machine learning system described and disclosed herein would be good candidates for intra-cardiac EP mapping and/or ablation or PVI procedures that are very likely to provide them with beneficial results.

FIG. 17 shows a block diagram and data flow diagram according to one embodiment of a body surface and intra-cardiac electrode machine learning system, which employs an atrial discriminative training (ADT) machine learning model (or MLM) that works in combination with a loss or cost function module (or LM). The ADT MLM is configured to provide its results or predictions to the LM, and in turn the LM is configured to provide outputs based on the ADT MLM's results or predictions back to the ADT MLM (more about which is said below). The ADT MLM can be any suitable type of machine learning module or network, such as one or more of the following types of networks or modules: convolutional neural network (CNN), decision tree, support vector machine, logistic regression, mixture of Gaussian, a feedforward neural network or artificial neuron network, a radial basis function neural network, a Kohonen self-organizing neural network, a recurrent neural network (RNN) or long short term memory network, and/or a modular neural network. The ADT MLM and/or the LM can also be configured to employ optimization techniques or schemes such as stochastic gradient descent schemes or decision tree schemes.

Continuing to refer to FIG. 17, in one embodiment of a body surface and intracardiac electrode machine learning system and its various components and associated methods, a goal is to estimate the properties of EGF using body surface electrodes only. EGF can help identify action potential flow patterns for improved understanding and treatment of AF. In some of the embodiments described above, EGF is estimated using intracardiac unipolar electrodes, which is costly and invasive. By using and leveraging body surface electrode data in combination with intra-cardiac electrode data and EGF results obtained therewith, initial patient evaluation or classification, PVI outcome prediction, coarse or general localization of AF drivers, and more precise follow-up quantification (e.g., "recurrence of AF likely to occur, yes or no) can be carried out at much lower cost, and with essentially no risk to the patient, as compared to conventional invasive intra-cardiac basket catheter EP mapping methods.

Still continuing to refer to FIG. 17, in one embodiment an atrial discriminative trained (ADT) machine learning model is trained to estimate the correlation of body surface electrode signals to EGF properties and characteristics derived from intracardiac electrodes. By way of non-limiting example, such a machine learning model can be a feature extraction method that employs wavelet decomposition and amplitude histograms in combination with a regression or classification model such as a support vector machine, a decision tree or logistic regression, an end-to-end model such as a deep neural network, and/or any combination or permutation of the foregoing.

As shown in FIG. 17, an input signal x to the machine learning model ADT comprises data recorded from body surface electrodes BS (x). In some embodiments, signal x potentially undergoes preprocessing steps, such as a high/low/band-pass filtering or for the compensation of ventricular artifacts (e.g., removing the QRST complex). The desired output(s) y of the machine learning model provides an estimate(s) for one or more properties of EGF in a patients heart, such as activity or flow angle stability. Training data (x, y) is obtained from simultaneous recordings from body surface electrodes (x) and intracardiac electrodes (y). In one embodiment, the machine learning model is parametrized with parameters W. These can be weights of neural network connections, etc.

The prediction of the machine learning model is then $\hat{y}=fW(x)$ (or "f of x, parametrized by W"). This prediction should be as close as possible to y. During training, parameters W are optimized so as to minimize the error in estimating y. Such an error can be described as a loss function $L(y, \hat{y})$, for example the modulus of the difference $L(y, \hat{y})=\|y-\hat{y}\|$. Which is carried out in block LM, as described above.

Since the target values y are derived from intracardiac electrodes located in only one atrium, but body surface electrodes pick up signals x from both atria, a mechanism is needed to compensate for this. The idea behind atrial discriminative training (ADT) is to ask the machine learning model to make two predictions: $fW(x)=(\hat{y}L, \hat{y}R)$, one for each atrium. However, the ground truth y from the intracardiac recording is only known for one atrium ($y=yL$ or $y=yR$). The cost function therefore separates the two predictions into $L(y, \hat{y})=\alpha\ L(yL, \hat{y}L)+-\beta L(yR, \hat{y}R)$ and the coefficients are set according to the locations of the intracardiac recordings: $(\alpha, \beta)=(1, 0)$ if $y=yL$ and $(\alpha, \beta)=(0, 1)$ if $y=yR$.

As a result, at training time, the machine learning model does not know which atrium it is supposed to predict, and predictions for the atrium that was not measured intracardially are not penalized. At test time, the machine learning model will be able to make predictions for both atria simultaneously. Consequently, the foregoing systems and methods can be used to localize and quantify drivers of AF.

It will now be seen that an ADT MLI can be trained to directly predict optical flow from two different input images, which correspond to: (a) optical flow images derived from intra-cardiac EP data; and (b) optical flow images derived from body surface EP data acquired at the same time and from the same patients. Training data need not be perfect or noise free.

After having read and understood the present specification, drawings and claims, those skilled in the art will now understand that configurations and architectures of MLMs other than those explicitly described and disclosed herein can also be used obtain similarly useful results. Moreover, and with reference to FIGS. 14, 15, and 16, the ADT MLM used to provide optical flow predictions from body surface electrode data can be continuously or periodically updated using intra-cardiac data and/or body surface electrode data. See, for example, Deep Learning blocks 711 and 811 in FIGS. 14 and 15. In addition, and with further reference to FIGS. 15, 15, and 15 and the text corresponding thereto in the present specification, in some embodiments the ADT MLM may also be configured, adapted and used to provide optical flow predictions from: (a) body surface electrodes; (b) electrodes included in cardiac monitoring patches; (c) electrodes included in ECG monitoring leads, and/or (d) in addition to any of the foregoing body surface electrode configurations, intracardiac electrodes, depending on the particular application at hand (more about which is said below). Whether located in a remote "cloud" server, a health care facility, or another type of location, machine learning training, updating, computations, and analyses can be are carried out using hardware and computer systems 300 similar those shown in FIGS. 1A and 1B, or using other individual, portable, stationary, conventional, network-based, and/or cloud-based hardware and computer systems, as those skilled in the art will understand.

With respect to the foregoing atrial discriminative machine learning models, and the systems, devices, components, and methods associated therewith, the following additional embodiments, features, and aspects are also contemplated.

Below we now describe various systems, devices, components, and methods that may be employed to enhance the resolution of EGF maps. Note that the above-described methods, techniques, systems, devices and components, as further elucidated in FIGS. 1A through 17, may, in whole or in part, be applied to the systems, devices, components, and methods described below.

Introduction: Atrial Fibrillation and Electrographic Flow

Atrial Fibrillation

Atrial Fibrillation (AF) is a prevalent human cardiac arrhythmia that can lead to severe illness. In addition to pharmaceutical treatments, catheter-based atrial ablation is a commonly used therapy for AF. AF is characterized by chaotic irregular patterns of excitation-wave propagation in the atria which lead to an absolute arrhythmic heartbeat.

In many patients, circular ablation of the pulmonary veins (pulmonary vein isolation or PVI) is effective in achieving freedom from AF. However, in about 40% of patients, it is necessary to ablate additional targets in the atrial wall that are thought to represent ectopic sources of excitation which compete with the sinus node (SN), the pacemaker of normal sinus rhythm (NSR). Ablation of putative sources has been shown to improve therapeutic outcome and often leads to acute termination of AF to NSR or sometimes atrial flutter (AFL) a more regular arrhythmia which can be treated by another systematic ablation strategy. To identify and locate ectopic sources of excitation it is necessary to analyze the electrical behavior of the atrial surface i.e., the traveling of excitation waves, also designated as the electrographic flow (EGF).

Electrographic Flow

Excitation waves in the human atrium in AF when recorded with extracellular unipolar electrodes are characterized by a rapid voltage decrease (RVD) and a subsequent increase after a time delay. Voltage amplitude, time course and steepness of the RVD can be very variable (see, e.g., FIG. 19), and among other factors depend on the individual AF-cycle, the density of the excitable cells, the size of the electrode, and its distance to the tissue.

FIG. 18 shows two seconds of unipolar electrograms recorded from five electrodes of the G-spline of a basket catheter, positioned in the left atrium of a patient in AF. The unipolar signal shapes are variable in time and between electrodes. In FIG. 18, the scale is 5 mV and 100 ms. The grey box represents ventricular far-field signals; a QRST artifact is superimposed caused by the heartbeat.

Basket catheters with 64 unipolar electrodes have typically been used to simultaneously record unipolar electrograms from multiple locations of the inner atrial surface to map EGF, and ultimately to determine and locate ectopic sources. For the purpose of EGF analysis, it is noteworthy that unipolar electrograms are recorded extracellularly, which means they represent a partially differentiated transformation of intracellularly recorded action potentials. The relevant component for EGF analysis is typically the RVD of the electrogram, which corresponds to the time point of the up-stroke of the intracellular action potential with good approximation. However, technically it does not matter for EGF analysis whether the slope of a signal is positive or negative. Any pattern that appears in multiple electrode signals, but that is time-shifted, can be used to detect flow.

One method currently applied to identify sources of AF from basket catheter recordings is based on a modified Horn-Schunck algorithm (HSA) applied to normalized and QRST-compensated recordings (Haines et at, J Interv Card Electrophysiol. 2022 Aug. 15. doi: 101007/s10840-022-01308-8). In one example, this technology starts from individual frames created by compressing 19 millisecond chunks of recorded data each into one 2D frame matrix. The HSA-based EGF method then determines sources of excitation from the average EGF calculated by HSA from frame to frame over segments of two seconds and finally creates summary maps of many segments. Diagnostic relevance of the observed sources is only reached after summarizing those maps over at least one minute.

Figure 19:
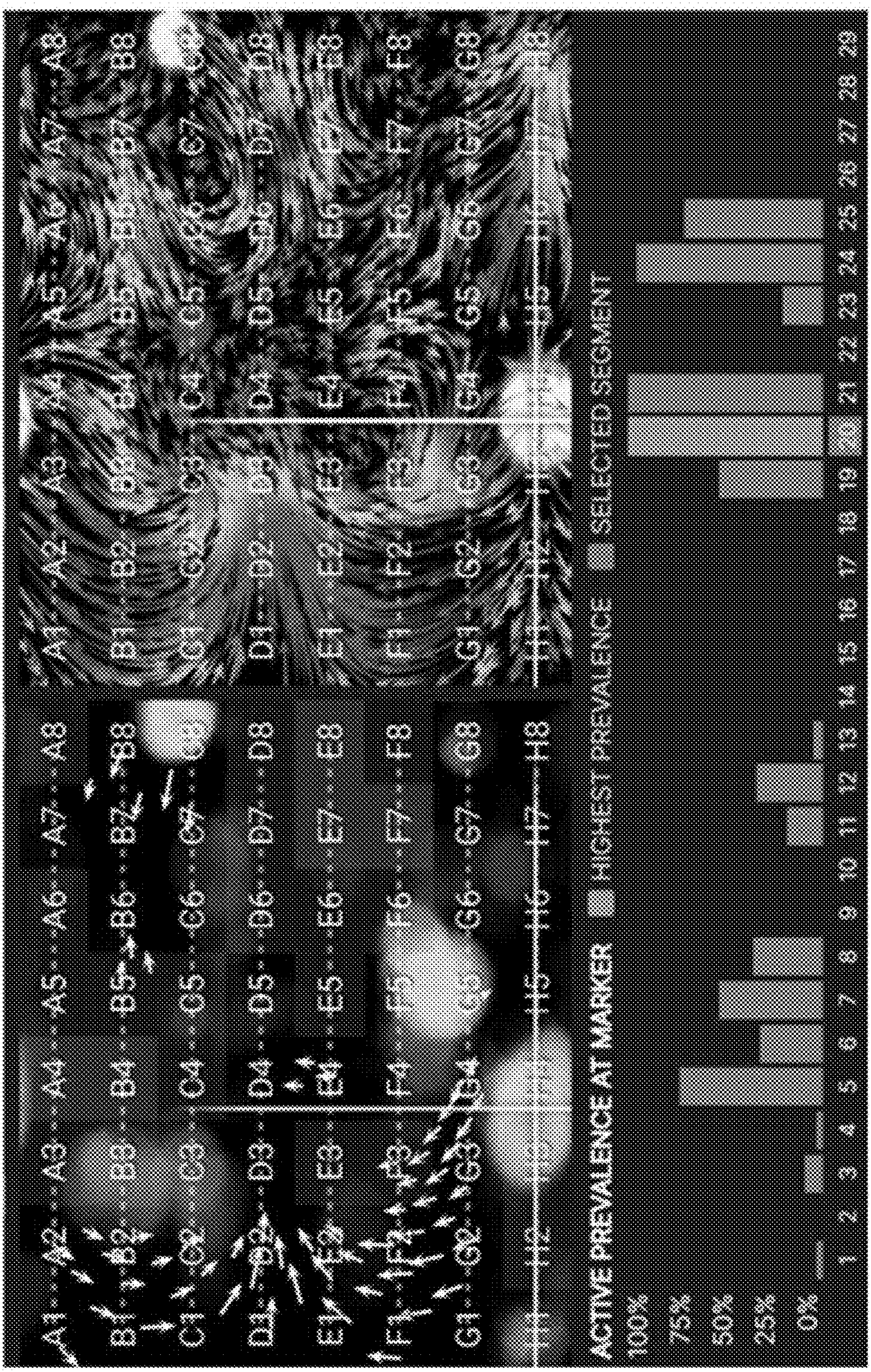
FIG. 19 shows results obtained using the data shown in FIG. 18.

FIG. 19 shows results obtained using the same data set as in FIG. 18. The source at H4 had 100% activity in segment 20, which is displayed in the segment flow map on the right. The left side of FIG. 19 shows the summary map over 60 seconds in which the source at H4 was active (or "prevalent") only for 24% and is therefore just below the threshold of being therapeutically relevant with high certainty. The source at GF5 is alternatively active for example in the segments 1 and 9 (not shown). Note that "activity" is sometimes referred to as prevalence, since activity is defined only during or over a recording.

In one embodiment, and by way of non-limiting example, therapeutically relevant sources can be most effectively discriminated from irrelevant ones by analyzing a minimum of 60 seconds to 180 seconds of recordings. Such sources are in fact reproducible in subsequent one minute recordings, which allows validation of their disappearance upon ablation (thereby indicating effective ablation). A recent clinical trial, FLOW-AF (NCT04473963), has shown that ablation of these sources, which were active at least 26% of the time before effective ablation, significantly improves procedural outcomes when compared to PVI alone.

Sources identified through HSA-based (Horn-Schunck analysis-based) EF mapping are believed to be the origins of excitation waves and can be localized in relation to the basket electrode grid, as demonstrated in FIG. 19. The exact mechanism of these sources may vary significantly, ranging from autonomous focal sources of excitation, to focal activations, spreading excitation previously conducted to the site of the source by independent conducting structures (such as epi-endo breakthroughs, tiny slow conduction pathways, septal activation, or Bachmann's bundle), micro or macro reentry-mediated rotational sources, and still other mechanisms.

The precise mechanism of individual EGF-identified sources is generally not clarified by current HSA-based EGF mapping for lack of sufficient spatiotemporal resolution, while its understanding is believed to be of potential therapeutic importance. In addition, and by design, in some embodiments HSA-based EGF aggregates observations in a way such that random components, as are often present in AF, are smoothed out. On the downside, doing so can hide some of the fine structure. Currently, ablations are effective in many cases, but in some instances the leading source moves away from the original location upon ablation and disappears only after a significant surface area has been ablated while hunting for the source. In rare cases, EGF-guided ablations are not effective at all. Since the effectiveness of ablation can always be checked directly after ablation in EGF-guided procedures, a more detailed understanding of the mechanisms of sources may not be deemed necessary. However, in the interest of shortening procedures and keeping ablations minimally invasive, determining the mechanism during pre-ablation analysis may be desirable in order to optimize ablation strategy. Moreover, in the case of macro-reentry as a mechanism the knowledge of the exact circuit is assumed to be necessary for effective treatment. In summary, there is a medical need for a strategy that can accurately resolve the detailed EGF pattern of a source with high spatial and temporal resolution.

Spatiotemporal Constraint Reconstruction of Unipolar Recordings

Introduction to Spatiotemporal Constraint Reconstruction (STCR)

Spatiotemporal constraint reconstruction (STCR) involves reconstructing an object or scene from multiple image frames to understand both its spatial and temporal aspects (see, e.g., Oswald et al.; ECCV 2014: Computer Vision—ECCV 2014 pp 32-46; Yer et al.; Magn Reson Imaging. 2012 June; 30(5): 610-619. doi:10.1016/j.mri.2011.12.021, and Liang and Pelc; U.S. Pat. No. 7,602,183). This can be useful in a range of applications, where it can create dynamic 3D models of organs or tissues for analysis and visualization. For example, STCR was used on angularly under-sampled (sparse) radial dynamic MRI myocardial perfusion data, and was able to reconstruct images with high accuracy using as little as 15% of full data. Additionally, the contrast to noise ratio was improved by 30%. (see Adluru et al.; 2007 4$^{th}$ IEEE International Symposium on Biomedical Imaging).

The mathematical principles and techniques used in STCR depend on the specific system being analyzed and the data available. These may include techniques such as optimization, machine learning, and/or spectral analysis to identify patterns and trends in the data and reconstruct the underlying constraints that govern the system's behavior. The goal of STCR is to identify these patterns and trends to understand the behavior of the system and make predictions about its future behavior.

Examples of STCR algorithms that may be adapted for use in EGF is applications include, but are not limited to: k-t TV-FOCUSS, k-t GRAPPA, k-t SENSE, k-t SLR, k-t PCA-GRID and k-t BLAST. They may all be used to improve the temporal and spatial resolution of dynamic MRI sequences. All such algorithms use k-space data as an input (which can be the electrogram data acquired from, e.g., a basket catheter), and aim to improve the quality of the images by taking into account additional information or constraints. All these techniques employ some type of an iterative reconstruction process, which comprises a set of mathematical steps that iteratively refines the estimated images until a predefined convergence criterion is met. They all have a similar goal, which is to improve the quality of EGF data by incorporating spatiotemporal information and constraints.

STCR Applied to Cardiac Electrophysiology

Here we show for the first time that the STCR principle can not only be used for image reconstruction (as, for example, in MRI data), but also surprisingly can serve to enhance the spatial resolution of recorded electrophysiological data (e.g., using a basket catheter in the right or left atrium of the human heart). In one embodiment, this is achieved by using constraints derived from the behaviour of unipolar electrograms and action potential wave propagation. It has been discovered that the resulting STCR-enhanced EGF maps are of significantly higher and enhanced spatial and temporal resolution than HSA-based EGF maps.

In AF, individual cycles of excitation wave traveling can be very variable and some sources which are only temporarily active are irrelevant for therapeutic outcome. Therefore, the main application of STCR enhanced EGF mapping in AF is the analysis of the mechanism of HSA-based EGF identified sources, which matter by being active over the long term and relevant to procedural outcomes.

Two independent fields of application of STCR enhanced EGF mapping include: (i) the analysis of atrial tachycardias and AFL where every individual cycle is very similar to all others and STCR enhanced EGF mapping can provide a complete highly resolved EGF map from any single cycle which indicates the exact mechanism of the arrhythmia, including the full pathway and potential slow conduction zones (or "isthmuses") of mechanistic relevance because the exact velocity of conduction (in most cases indicated by direction and magnitude) is a parameter resolved by this method.

The second new application of EGF enabled by the STCR enhancement includes. (ii) the detection of highly resolved velocity maps in normal sinus rhythm (NSR). This is a new type of analysis not yet clinically validated but with the potential to identify fibrotic areas in the atrial wall based on their arrhythmically most relevant parameter: slow conduction. This may eventually be superior to the commonly used parameter of voltage amplitude and synergistic with the novel approach of mapping of HSA-based EGF flow-consistency. Velocity maps in NSR can be obtained from a single beat which would save significant procedure time compared to common voltage maps.

Theoretical Basis of STCR-Enhanced EGF

Data recorded from a 64-electrode basket catheter typically consist of unipolar electrograms with variable recording quality which are mixed with ECG signals, noise, and electrostatic fluctuations. For the use in STCR-enhanced EGF mapping, at first data must be preprocessed to improve and isolate the unipolar electrograms and normalize their amplitudes as described in the Unipolar Reconstruction section below.

In improved and normalized data, the amplitude is now called Intensity (1), which relates to the state of the excitation and in one embodiment is scaled between −0.5 and 0.5 (amplitude of unity) at a given point on the surface. Such atrial surface points which are actively participating in the excitation waves change is their intensity repeatedly between −0.5 and 0.5. Those which are permanently (not touching excitable tissue) or temporarily (in refractory period) inactive have an intensity kept near zero.

Following sections refer to a short interval of these data; namely, the time needed for an excitation wave to travel at least once to every active electrode. This interval is called "one Cycle" and normally has a duration of 140 to 230 ms. In AF, every cycle is at least slightly different, and in AFL or SR cycles are rather stereotypically all the same or are clustered in groups with identical or near-identical duration and shape.

Mathematically, the intensity function I(x, y) describes the surface, where (x, y) are the coordinates of a point on the surface in a two-dimensional Cartesian coordinate system. The gradient h of this function is a vector field given by the vector:

$$h = \nabla(I(x, y)) = (\partial I/\partial x, \partial I/\partial y) \tag{1}$$

The gradient vector points into the direction of the steepest increase (when the components are positive) or steepest decrease (when the components are negative) of the intensity surface at a given point. When excitation waves travel, gradient vector field h travels with time. Each point of h thereby travels with its own velocity and into its own direction defining another vector field of velocities:

$$F(x, y, t) = u(t), v(t)) \tag{2}$$

with u and v representing the two velocity components in X- and Y-directions at each point in time during a Cycle.

Figure 20:
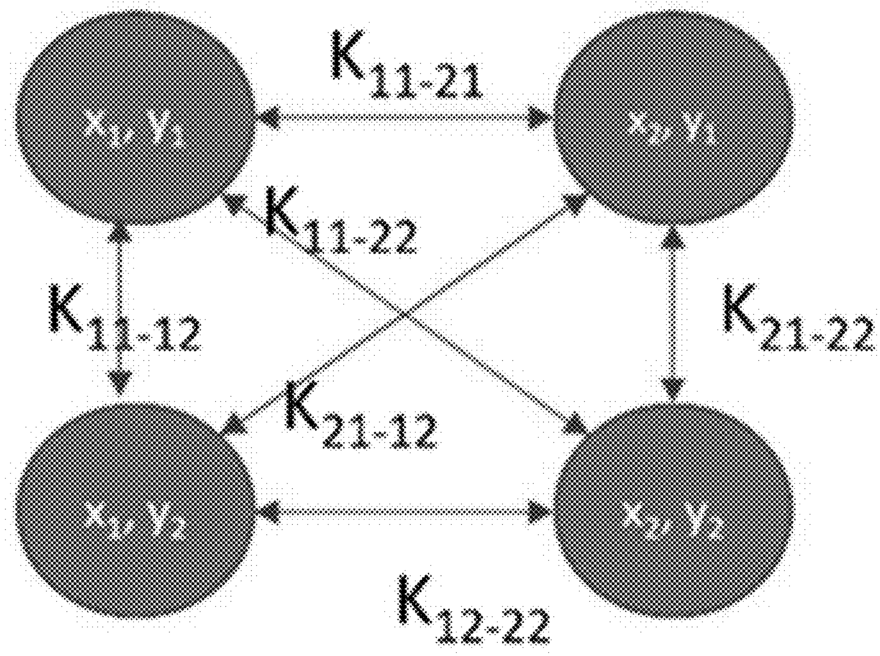
FIG. 20 shows a Unit Domain formed by neighboring electrodes.

FIG. 20 shows a Unit Domain formed by four neighboring electrodes, which as illustrated permit or allow six correlations. By measuring I(x, y, t) for every electrode in recordings from a basket catheter, we only receive sparse points for x and y—but at a very good time resolution (e.g., 1 or 2 msec. sample rates). To understand how best to deal with this situation, we focus on an array of only four electrodes we call a Unit Domain in which we want to know $I(x_i, y_i, t_0)$ at a given time (t=zero). In a Unit Domain the four electrodes are $x_1, y_1$; $x_2, y_1$; $x_1, y_2$ and $x_2, y_2$. $I(x_1, y_1, t)$ therefore refers to the intensity profile of one full Cycle from the first electrode and $I(x_2\text{: } y_2, t)$ refers to the intensity profile from the second electrode, and so on. See FIG. 20. Generally, it is assumed that the wavelength of the excitation waves with 30 to 300 mm is larger than the size of a Unit Domain.

Hence, in the simplest possible (orthogonal) case where the velocity vector field between the first two electrodes in the Unit Domain, $F_{11\text{-}12}$=(a, 0), is constant and has only an x-component of constant magnitude $u_{11\text{-}12}(t)$=a and $v_{11\text{-}12}(t)$=0, and the correlation of these two electrodes' data $K_{11\text{-}21}$ given by:

$$K_{11-21}(d) = I(x_1, y_1, t) \otimes I(x_2, y_1, t), \tag{3}$$

which is maximal at a time shift d of Δt. We can further assume that the intensity gradient profile existing for t=0 at the points located in between $X_1, Y_1$ und $X_2, Y_1$ is very similar to both the past temporal intensity transient at $X_1, Y_1$ and to the future intensity transient at $X_2, Y_1$:

$$I(x_{1-2}, y_1, t_0) \sim I(x_1, y_1, t_{0-\Delta t}) \sim I(x_2, y_1, t_{0+\Delta t}) \tag{4}$$

where $I(x_{1\text{-}2}, y_1, t_0)$ is the spatial series of intensity values between $X_1$, $Y_1$, and $X_2$, $Y_1$, $I(x_1, y_1, t_{0\text{-}\Delta t})$ is the temporal series of intensity values measured between t=0 and t=Δt at $X_1$, $Y_1$ and $(x_2, y_1, t_{0\text{-}\Delta t})$ is the temporal series of intensity values measured between t=0 and t=Δt at $X_2$, $Y_1$.

In other words, the future temporal intensity profile at an early electrode as well as the past temporal profile at a late electrode can be projected along a homogenous velocity vector field to estimate the spatial profile between the electrodes.

The same pair of relationships can be formulated for each of the six neighborhood relationships in a Unit Domain. We call this process forward and backward Spatiotemporal Projection.

In any real case, the velocity vector field will mostly not be both constant and parallel to the direction of one electrode pair. The Unit Domain rather will be crossed by an excitation wave leading to intensity transients to be recorded, but with differential correlation time shifts because the time points at which the excitation crosses the individual electrodes will all be different.

In such a more complicated case, the time shifts in X- and Y-direction (d) are inversely related to the vector field direction:

$$d_y / d_x = u / v \tag{5}$$

If the electrode pair is oriented in a direction perpendicular to the vector field direction, the time shift will be zero because the wavefront passes the electrodes at the same time while it will be maximal if they are in line with the vectors.

Hence, if we apply the forward and backward Spatiotemporal Projection (3) to all six neighbor relationships of the Unit Domain and the flow field is still constant but not parallel to one electrode pair (constant Case), we will still get correct estimates for the individual vector components.

Forward and backward Spatiotemporal Projection applied to all six neighbor relationships of a Unit Domain yields 12 spatial intensity value data series, which in the constant Case are all consistent and show parts of the same picture.

In another more complicated case, spatially inconstant velocity fields, where F(x, y, t) depends on y and x by being divergent, convergent, or curled, and only being constant with respect to t within a cycle (linear Case), the projections are less good approximations at points that are not near or close to the projected electrode because the vectors are changing direction between the two electrodes. Still, this allows a reasonable approximation if one calculates one additional point each with the forward projection, and one with the backward projection near to the respective opposite electrodes, and determines one intensity value in the middle by weighted interpolation between the two projected results from the two electrodes. For an optimal result, the points mainly based on the forward and the backward projection may be weighted as follows:

$$I(x_{1.25}, y_1, t_0) \sim (3*I(x_1, y_1, t_{t-0.25\Delta t}) + I(x_2, y_1, t_{t+0.75\Delta t}))/4; \quad (6)$$

$$I(x_{1.75}, y_1, t_0) \sim (3*I(x_2, y_1, t_{t+0.25\Delta t}) + I(x_1, y_1, t_{t-0.75\Delta t}))/4$$

and $$I(x_{1.5}, y_1, t_0) \sim (I(x_1, y_1, t_{t-0.5\Delta t}) + I(x_2, y_1, t_{t+0.5\Delta t}))/2$$

Points calculated by this principle inside a Unit Domain are referred to herein as correlation derived values or CDVs. Based on the same principle, the CDV in the center of the Unit Domain is being determined as the average of four individual projections. Taking into account the spatially inconstant velocity fields in real data (such as shown in FIG. 21), we concluded that an increase by more than a factor of four of the density of the reconstructed Intensity matrix compared to the electrode resolution (i.e., more than three CDVs between two electrodes each) does not further improve resolution meaningfully.

Figure 21:
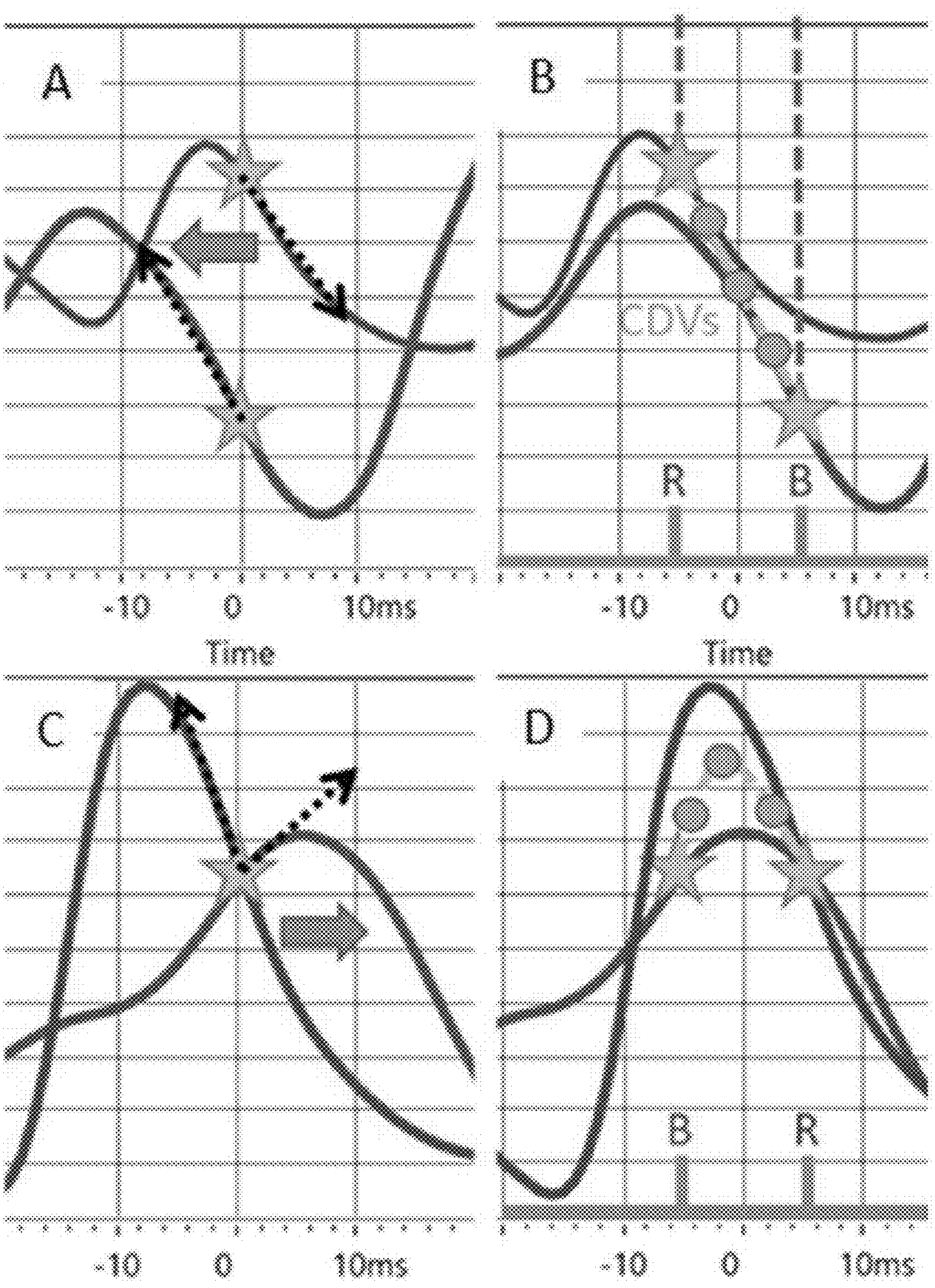
FIG. 21 illustrates the concept of spatially inconstant velocity fields that can occur in real data.

Referring now to FIG. 21, the principle of forward and backward so Spatiotemporal Projection from a linear case recorded in an AF patient is illustrated, where there are shown:

(A) Unipolar signals from two neighboring electrodes (blue and red) correlate with a time shift of red to blue of −10 ms. At time point zero (yellow star) the red (early) electrode is directly after the peak, while the blue (late) electrode is already 10 ms later downhill in the excitation wave cycle. The forward projection of the red, early electrode leads to roughly the same value as the backward projection of the blue (late) electrode;

(B) Forward and backward projection with weighted interpolation (yellow dotted line) yields an almost straight line on which the three CDVs are determined. Now, the time scale is converted into the spatial scale of electrode distances (orange) with the position of the red and blue electrode, respectively;

(C) Blue and red are now a different set of electrodes. This time red is after (late) and blue is before (early) the peak of the respective wave cycle, and the time shift red to blue is +10 ms. Both, backward projection and forward projection are now going into the direction of the peak of the wave, and (D) Forward and backward projection with weighted interpolation (yellow dotted line) yields now yields the spatial peak in between the electrodes on which the three CDVs are determined.

Forward and backward Spatiotemporal Projection reconstruction works well if the excitation wavefronts arrive at the earlier electrodes and leave the Unit Domain at the late ones. If this is not the case, however, because there is a singularity or a block inside the Unit Domain, those projections are unfortunately no longer meaningful. A singularity hereby means that the excitations are either arising from a source or vanishing in a sink in inside the Unit Domain.

Such cases are referred to as a non-linear Case and must be recognized and handled differently: In the case of a block with a lack of any correlation, a wave node with zero intensity is to be introduced as a zero level intensity value accounting for the end of a wave's traveling. In the case of a singularity, the electrodes show no or only a small time shift but at a relatively high correlation.

Fortunately, in most non-linear Cases most of the eight neighboring Unit Domains are linear. Hence, they provide intensity gradients (h) for all four boundaries of the Unit Domain. In the non-linear case the best estimate of the points inside the Unit Domain is a minimal bending energy fit of the boundary gradients into the Unit Domain. For a sink this will provide a minimum, for a source a maximum and for a block where a zero point or line is introduced the best fit for a wave node.

To reconstruct the Intensity surface in a non-linear Unit Domain between four gradients we minimize a cost function based on the biharmonic bending energy E of the surface defined as:

$$E = \int\int (I) * (\Delta^2 * f(x, y))^2 \, dh \quad (7)$$

where I refers to the adjacent Intensity values in the neighbor unit domains in X- and Y-direction defining the gradients (h), f(x, y) is the surface to be determined approximated by a radial basis function, and $\Delta^2$ is the biharmonic operator. The same optimization is also used to combine all reconstructed CDVs for the linear and constant Cases into one smooth surface by adding energy optimization derived values (EDVs).

The resulting smooth Intensity maps have still the original amplitude normalized between −0.5 and 0.5. Determining where the spatial gradient (h) is maximal yields maximal gradient lines for both the wavefront and for the wave-tail. The discrimination between front-lines and tail-lines results from the overlay of two subsequent Intensity maps:

$$h_{max}(x, y, t) = h_{max,front}(x, y, t) \quad (8)$$

$$\text{for } x, y$$

$$\text{and}$$

$$t \text{ if } I(x, y, t) > I(x, y, t+1)$$

where $h_{max}$(x,y,t) is the maximum gradient $h_{max,front}$(x,y,t) is the maximum gradient which at the same time corresponds to the wavefront and I(x,y,t+1) is the Intensity which decreased at the time t+1 vs the value at time t, I(x,y,t), because of the RVD.

The final STCR enhanced EGF map consists of all $h_{max,front}$ lines for a full Cycle, where the lines are sequentially colored from red=early to blue=late. In cc one embodiment, lines of neighbor color and therefore neighbor time normally have a time distance of 1 millisecond. Hence, their spatial distance is directly displaying the velocity in distance units per millisecond. In other words, slow conduction is indicated by narrow lines while rapid conduction and high velocity means large distances between lines.

In some embodiments, HSA-based EGF maps are not created from Individual Cycles but from longer time segments (e.g., 2 sec. to 60 sec.), to generate an average electrographic flow vector field that represents the average behavior of excitation waves over a such a longer period of time. In such EGF maps, the locations of sources of excitation are usually clearly identifiable, and the ablation of sources with more than 26% activity per one-minute has been shown to yield significant benefit for therapeutic outcome when compared to PVI alone.

The main limitation of the HSA-based EGF method had been the lack of resolution of excitation flow patterns of a source on a millisecond and millimeter scale. Although this is not necessary to identify a source or validate its disappearance in a control recording after ablation, it is beneficial to understand the exact mechanism of a source (e.g., if a source is an autonomously active spot or if excitation that spreads from a source re-enters the source as the aftermath of a previous cycle).

In some embodiments, an HSA-based EGF method starts from average data from each 19 msec. of recording, which is then condensed to the average flow information of 2 to 60 seconds. This is necessary since HSA requires consecutive frames with enough of a difference to converge. Hence, HAS-based EGF, although prognostically most powerful, discards the original information contained in 19 msec. of a recording made with 1 msec. resolution and can therefore not detect the detailed mechanism.

This is the capability of the STRC-enhanced EGF maps introduced here. Millisecond resolution and an up to four times higher spatial resolution allows the discrimination of mechanisms of electrophysiological phenomena like sources.

Detailed Description of Some Embodiments of Enhanced Resolution EGF

Recordings of cardiac unipolar electrograms obtained from a 64-pole basket catheter provide high time resolution due to the use of a high sampling frequency (1000 or 2000 Hz), but this is offset by a low spatial resolution of more than 1 cm between the basket catheter electrodes. This contrasts with the cellular level, where the myocardiocytes, which can spatially be only 100 micrometers in size, but may produce stereotyped action potentials at a low repetition frequency of 5 to 7 Hz. To analyze the detailed functional properties of the excitation patterns of the atrial wall with a basket catheter, it is useful to increase the spatial resolution using STCR. To achieve this, two constraints are applied: the stereotyped shape of unipolar electrograms and the property of excitation waves to propagate at a velocity between 50 and 500 mm/sec.

In one embodiment, the first steps comprise: (i) initial analysis and preprocessing of the Raw-Data to adapt the STCR hyperparameters to the properties of the atrial rhythm, followed by: (ii) reconstruction of the temporal shape of the unipolar electrograms and finally by: (iii) waveform spatial reconstruction and the generation of the activation time plot.

Initial Analysis

Figure 22:
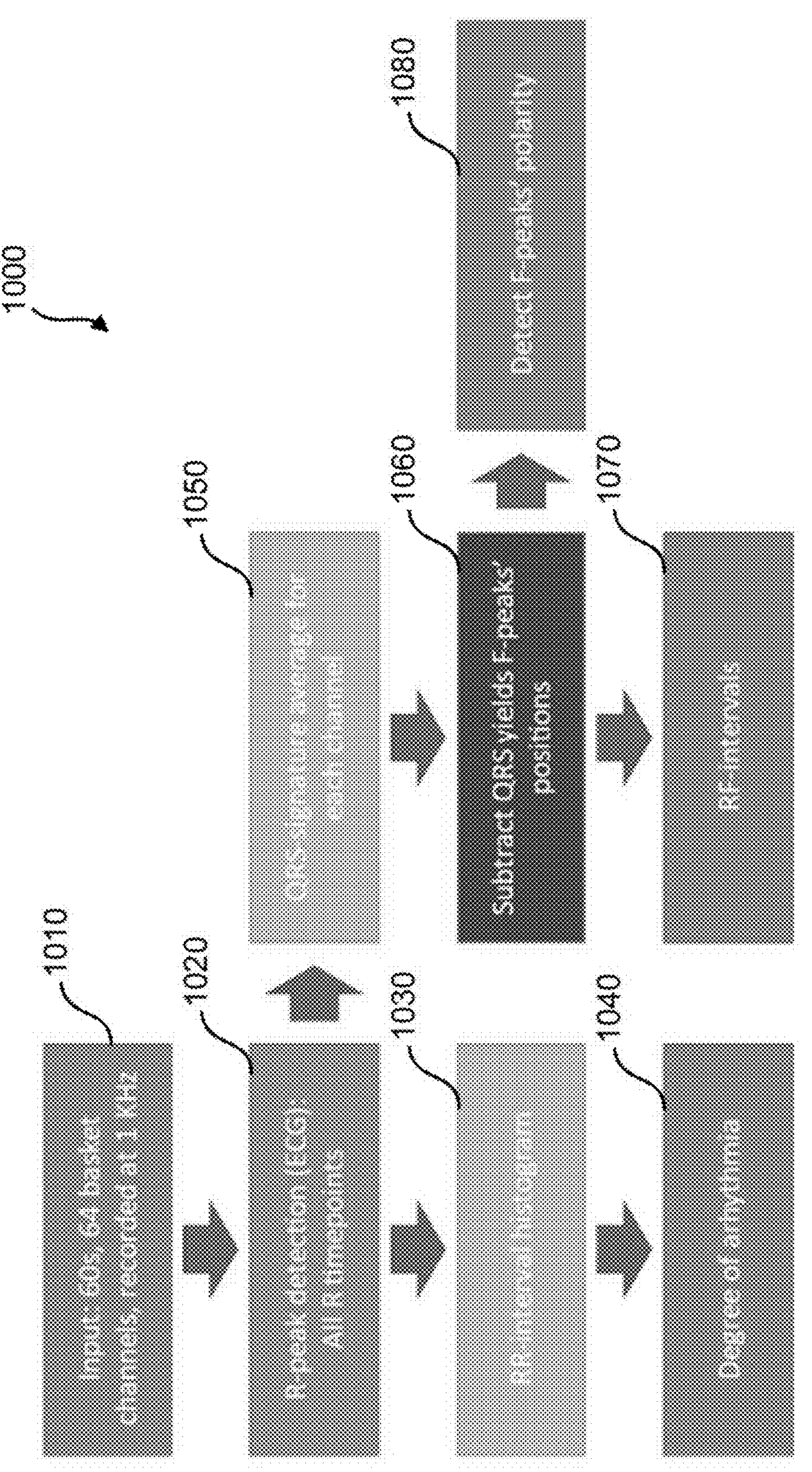
FIG. 22 illustrates one embodiment of a method for deriving initial parameters.

Method 1000 in FIG. 22 illustrates one embodiment of how initial parameters can be derived: Degree of arrhythmia, histogram of RF-intervals and F-wave polarity. In one embodiment and as an illustrative example, and continuing to refer to FIG. 23, 60 seconds of basket recordings composed of 64 channels from 64 evenly spaced electrodes sampled at 1 KHz are used as a data source in step 1010. In an initial analysis at step 1020, positions of all R-peaks are determined from a body surface ECG channel. A first parameter determined from this dataset is a histogram of all R-peak intervals at step 1030. The width of the peak of this histogram represents an objective measure of the rhythm: Atrial Fibrillation has a as broad histogram width, while more regular rhythms like Sinus Rhythm (SR), Atrial Flutter (AFL) and Atrial Tachycardia (AT) have a smaller histogram peak width (see step 1040).

Next, and with reference to steps 1050, 1060 and 1070, a short trace of voltage values recorded around each R-peak from each channel is being averaged and this averaged R-peak trace is subtracted from the same channel at each R-peak position (which eliminates about 90% of the QRS peaks' height from the unipolar recording). The purpose of this step is to enable detection of all F-wave peaks of the unipolar electrograms of the basket channels.

Next, at step 1080 all discernable F-wave peaks are detected. Peaks are associated with RVDs, which represent the time-point when sodium channels of the myocardiocytes open and mediate a sodium ion influx (action potential). The polarity of the steepest rapid slopes of the F-waves is detected to validate or if needed correct the polarity of the recording to determine the RVD positions. Next, the respective time points of the F-wave RVDs nearest to the R-peaks are determined and the average interval between the R-peaks and the subsequent F-wave peak is calculated. In SR this interval is larger than 400 ms while in all tachyarrhythmias like AF, AFL and AT it is shorter than the cycle length of the atrial electrograms (below 250 ms).

All parameters determined thus far are subsequently used to adapt the FTCR hyperparameters to the respective rhythm in the recording.

Unipolar Reconstruction

Figure 23:
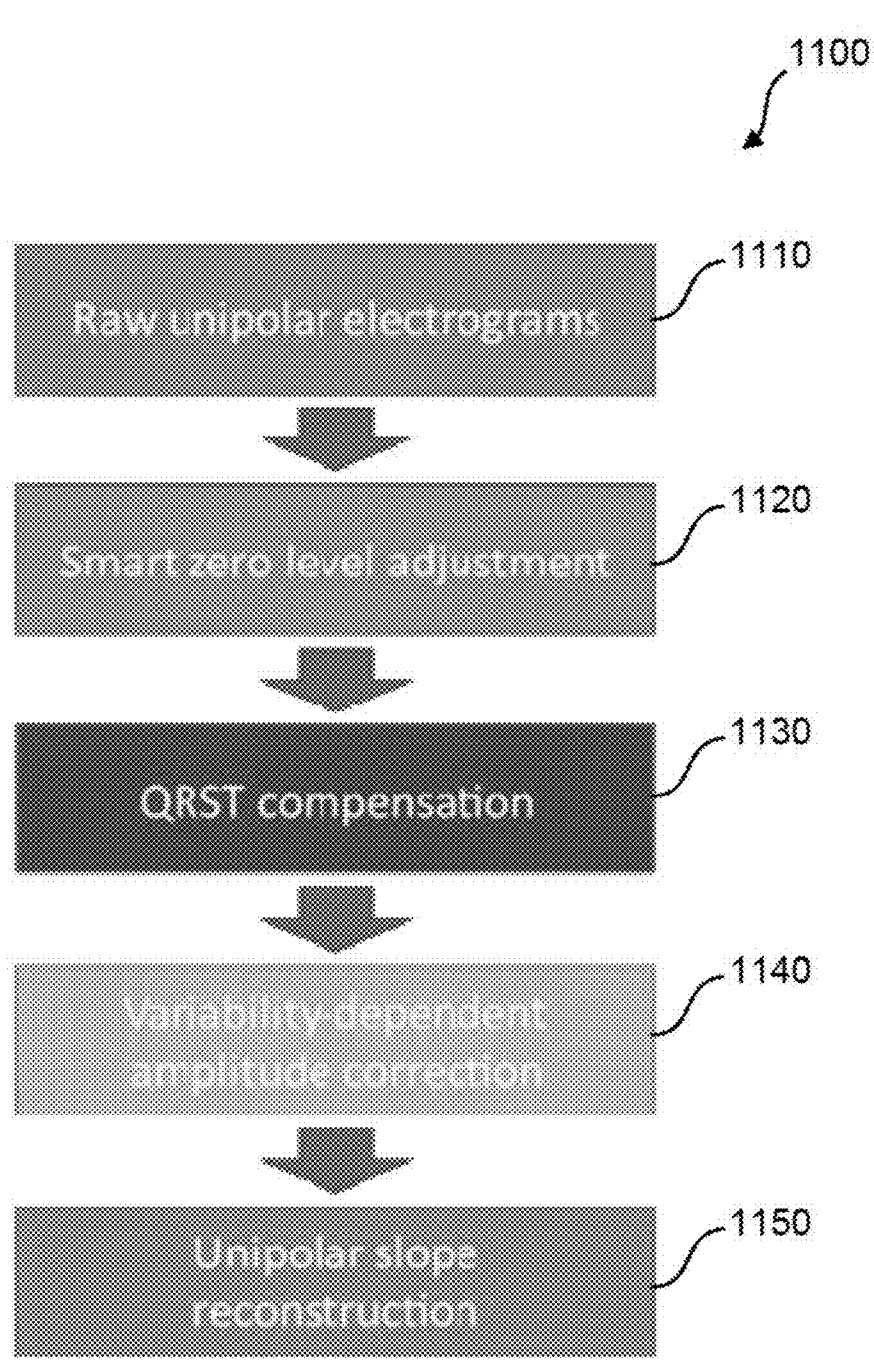
FIG. 23 illustrates one embodiment of a method for pre-processing and unipolar reconstruction based on initial parameters.

Method 1100 and steps 1110 through 1150 in FIG. 23 illustrate one embodiment of pre-processing and unipolar reconstruction based on initial parameters. Basket catheter recordings display a high variability depending on: (i) distance between electrode and atrial surface which influences amplitude and voltage slope, (ii) substrate healthiness and fibrosis influencing the amplitude and fractionation of the electrograms, and (iii) electrical and mechanical noise. To reconstruct uniform unipolar potential shapes from basket recordings three sets of smart filters may be used, as described below.

Raw data often display an inconstant zero level (step 1110). A smart baseline correction filter at step 1120 estimates the shifts of the baseline level by considering the F-wave peak positions and the average baseline of each cycle. This filter applies a spline fit to the F-wave peaks yielding baseline compensation even if the cycle length is inconsistent in AF.

Next, at step 1130 the complete QRST shape is subtracted from each channel, which is calculated as described for the QRS signature above. The main purpose at that point is the rather complete removal of the ventricular T-wave because the QRS component cannot be fully removed and the QRS contaminated parts of the signal are subsequently discarded.

In the next step (1140), the amplitude of each cycle is normalized by first shifting the zero-line of each cycle down to the two-Sigma level of the signal and then dividing by 4 Sigma of the datapoints of the cycle.

In the final step (step 1150) the RVDs of the unipolar electrograms are reconstructed by first low-pass filtering then correcting to a uniformly steep slope wherever the original slope has been consistent for three milliseconds or more. This largely improves the signal to noise ratio of the unipolar electrograms.

The hyperparameters of all steps of the Unipolar reconstruction are set in dependence from the results from the Initial Analysis above.

The intensity values obtained after Unipolar reconstruction represent an approximation of a convolution of all myocardiocytes' states in their individual action potential cycle below the respective electrode. Because propagation of excitation on the microscopic level is complex and composed of multiple layers of activity, such as endocardial and epicardial, those intensity values may sometimes follow chaotic time courses. Although, the wavelength of overlaying waves is generally in the range of 30-300 mm, because of this complexity, 64 electrodes are sparse and unipolar reconstruction and a potentially subsequently performed standard interpolation cannot sufficiently estimate a detailed intensity image of electrographic flow.

An electrode density of 2 to 4 mm has generally been accepted as sufficient to perfectly measure electrographic flow. However, such catheters are currently unavailable and would be very expensive to produce. An alternative is therefore to enhance spatial resolution by STCR using a correlation matrix to reconstruct spatial waveforms.

Correlation Matrix to Reconstruct Spatial Waveform

Figure 24:
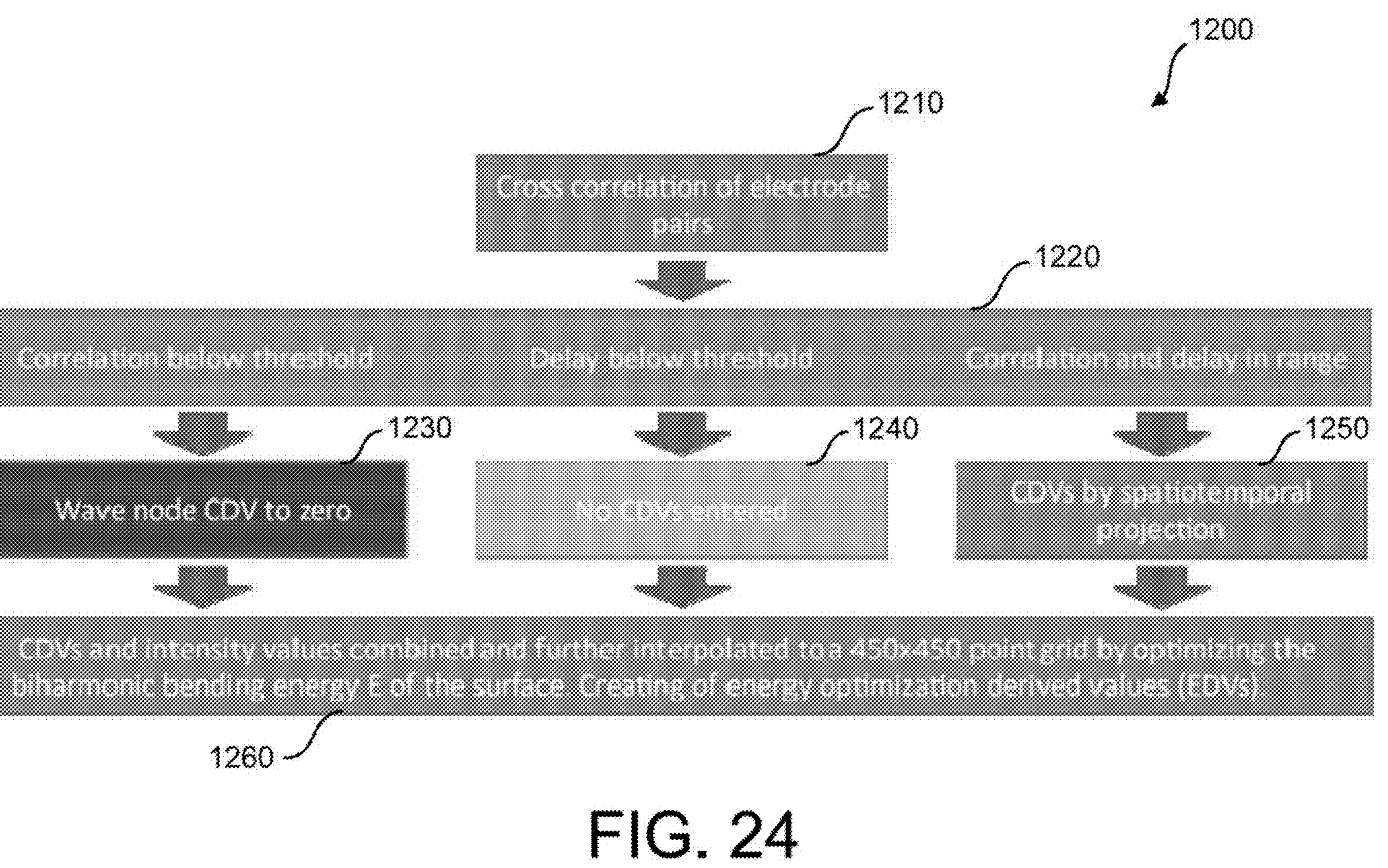
FIG. 24 illustrates one embodiment of using a correlation matrix calculation and spatiotemporal projection to create CDVs and derive a full STCR surface.

Method 1200 in FIG. 24 illustrates one embodiment of using a correlation matrix calculation and spatiotemporal projection to create CDVs and derive a full STCR surface by filling all gaps with energy optimization derived values.

The reconstruction of unipolar electrograms from raw recordings is described above. This step aims to generate a consistency in the data between recording channels, so that the recorded voltage levels at each millisecond and electrode can be interpreted as 64 sparse points from an image of the electrographic flow's wave pattern. In one embodiment, the resulting data from this reconstruction are no longer physically defined as voltage values, but as intensities on a scale between −0.5 and 0.5, an amplitude of unity, according to the all-or-nothing principle of action potentials.

In one embodiment of a final STCR approach, we enhance spatial resolution by using a correlation matrix-based projection of the time dependent intensity onto the intervals between the electrodes. This is based on the paradigm as that excitation that can be recorded in a time-dependent manner is always propagating from or to the point of recording, although in an unknown direction. Besides direction, three different possible behaviors of the waves can be discriminated: (i) regular wave propagation, (ii) wave origination due to a local source of excitation, and (iii) wave propagation block due to a lack of conducting substrate creating a wave node.

Although somewhat spherical in shape, standard basket catheters are usually represented by an eight-by-eight matrix because they comprise eight splines with eight electrodes each. The 64 electrodes of a basket catheter are traditionally numbered from A1 to H8 where A to H are the eight splines, and the A1 to H1 electrodes are situated around the north pole, and the A8 to H8 electrodes around the south pole. Any subarray of four electrodes (called Unit Domain n, n+1, m and m+1) has six neighbor relationshipships (to the left of FIG. 25) to be analyzed to generate three additional CDV data points for every millisecond sample. Referring to the center portion of FIG. 25, this Unit Domain of four electrodes can, by way of example, comprise electrodes or locations A5, A6, B5 and B6. The H electrodes have A electrodes as their next neighbors. A bit more complicated are the two poles (to the right of FIG. 25) because neighborhoods may cross the pole. For example G1, H1, C1 and D1 form one Unit.

Figure 25:
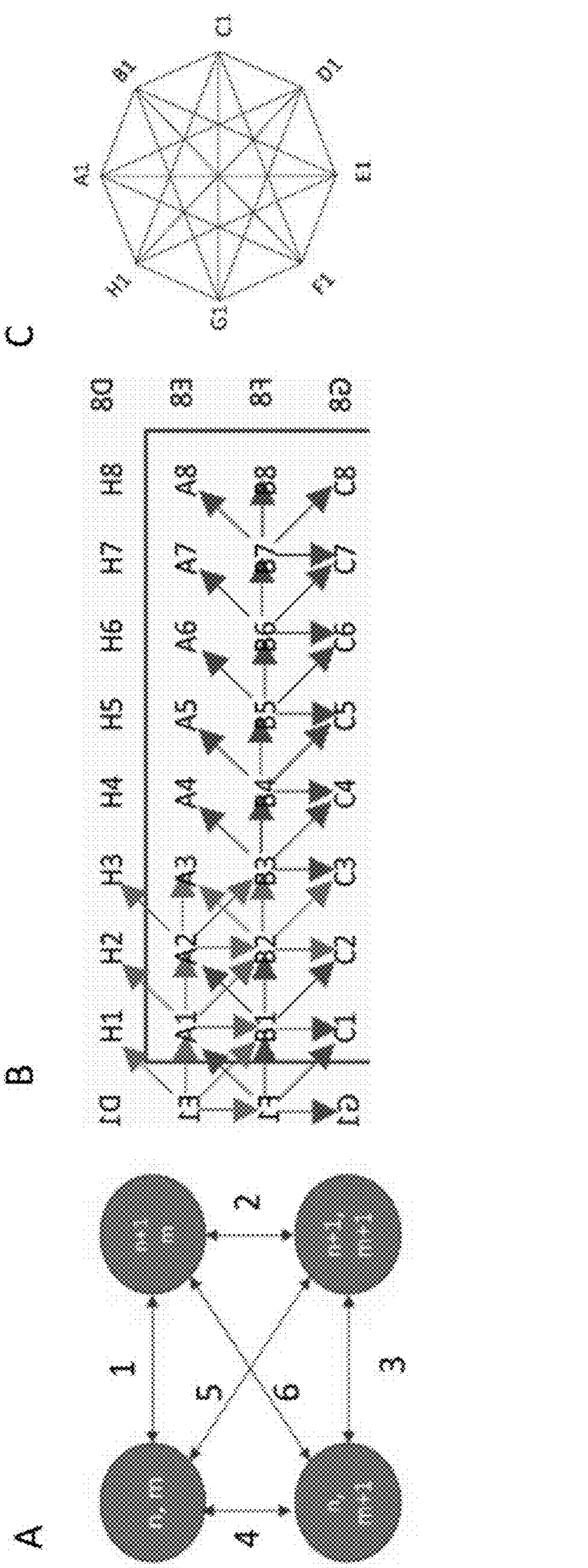
FIG. 25, illustration A denotes application of the Unit Domain concept; illustration 8 denotes stepwise processing of four correlation neighborhoods each throughout the 8×8 grid of the basket catheter, and illustration C denotes pole projection of the correlation neighborhoods as defined by the inversely extended 10×10 grid of Drawing B.

In FIG. 25, and according to one embodiment, Illustration A denotes application of the Unit Domain concept; Illustration B denotes stepwise processing of four correlation neighborhoods each throughout the 8×8 grid of the basket catheter, and Illustration C denotes pole projection of the correlation neighborhoods as defined by the inversely extended 10×10 grid of Drawing B. The CDV is a dataset which is built on top of the array of electrode intensity values calculated for each sample in time (e.g., every 1 ms).

For each neighbor relationship, the time dependent correlation is determined over at least plus-minus one Cycle length of time. The first maximum in each correlation provides a max amplitude (correlation) and a time point (time shift). These values from all relationships within a Unit Domain are used to reconstruct CDVs inside the Unit Domain based on the following decision tree:

(i) If the time shift is less than a given small percentage of the cycle length (the quasi-instantaneous case) the wavelength vector component in the addressed direction may be either much larger than the electrode distance or there may be synchronizing singularity (a source or sink) in such Unit Domain with small, similar run-times on all sides. No values are added to the CDVs in this case. Additional energy optimized Intensity points (EDFs) are to be generated in the second step from boundary gradients of the adjacent neighbor Unit Domains.

(ii) If the time shift is between the given minimum and half the cycle length (maximum) but the correlation is low, it is likely that the myocardium between the electrodes is non-conducting although both electrodes display electrograms. This indicates a wave node in which case the center between the electrodes is set to zero and EDFs approximating a standing wave are created from boundary slopes of the adjacent neighbor Unit Domains. If one of the non-correlating electrodes has a very low voltage which is below the normalization threshold (30%) this electrode area is left as non-active.

(iii) If both correlation and delay are in range the two electrodes are connected by a set of three CDVs created by forward and backward Spatiotemporal Projection.

Finally, all gaps in the intensity matrix are filled by EDFs.

Activation Time Plot

Figure 26A:
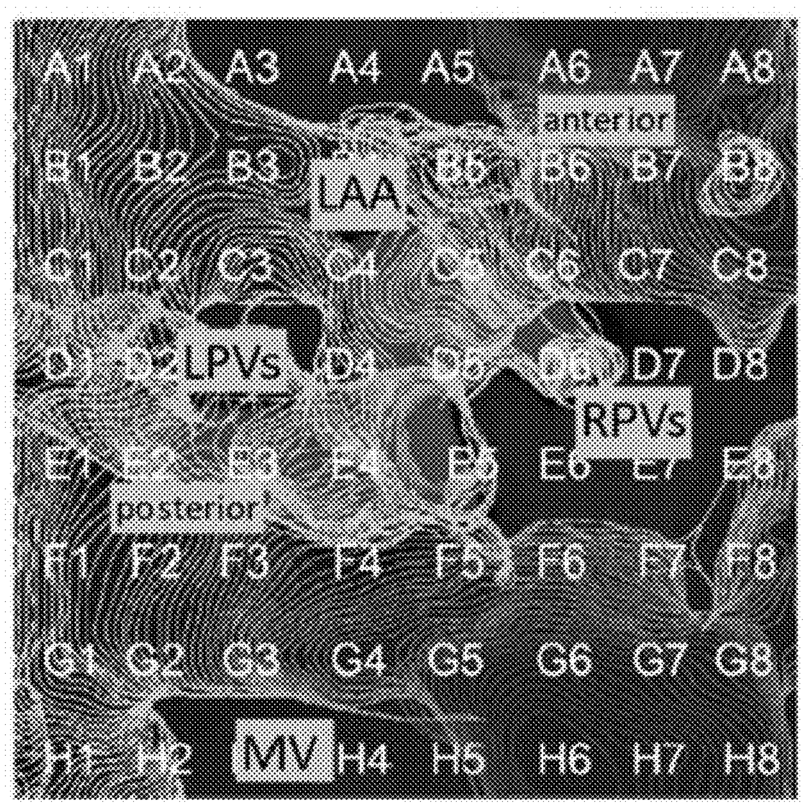
FIG. 26A shows an example of STCR-derived maximal gradient wavefront lines.
Figure 26B:
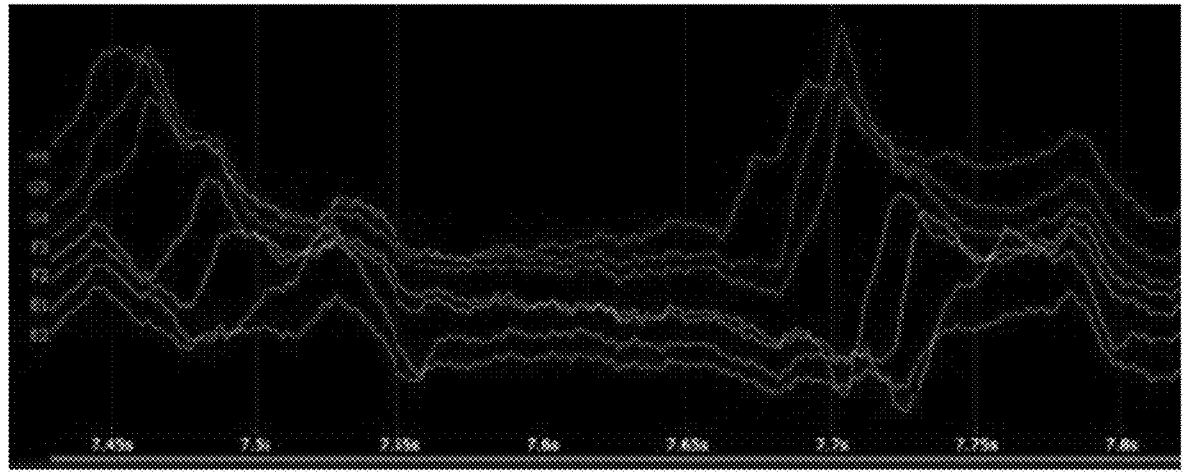
FIG. 26B shows corresponding original raw Unipolar Electrograms of the same cycle used to create FIG. 27A.

In one embodiment, after reconstructing the Intensity value matrix for each sample, maximal gradient lines are derived for both the wavefront and for the wave-tail. The discrimination between front-lines and tail-lines is then determined as described above from the overlay of two subsequent Intensity maps. The activation front for each sample is then plotted in a different color of the rainbow to indicate local activation time of the respective sample (from red=early to blue=late). The images in FIGS. 26A and 26B show an example of organized AF in the LA, where the RA is driving through a focal activation from Bachmann's Bundle (H6). The activation wave then travels on both sides around mitral valve AH34 anterior and on the bottom of LA to the posterior wall, where the excitation wave appears twice: once early coming from the bottom and once late coming around LAA and the LPVs.

FIG. 26A shows an example of STCR-derived maximal gradient wavefront lines, rainbow colored from red to blue (early to late) as the final representation of an STCR-enhanced EGF map from an AF patient. FIG. 26B shows the corresponding original raw Unipolar Electrograms of the same cycle used to create FIG. 26A, and displays the complexity and variability of an AF cycle, where the polarity of RVD=upward.

Results

1. STCR-Enhanced EGF Applied to Simulated Data

Figure 27C:
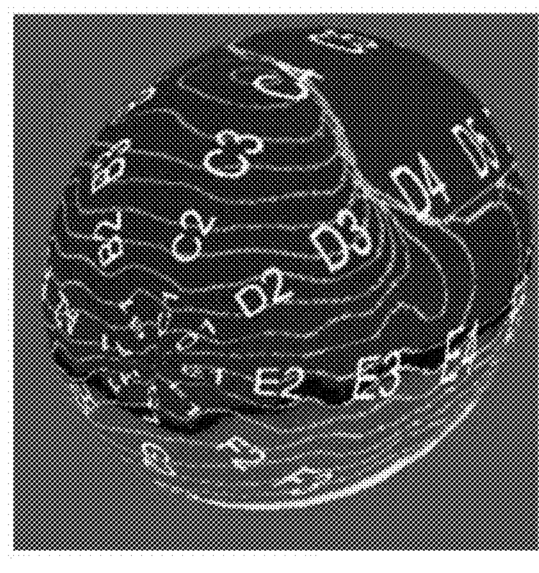
FIG. 27C displays pole projection of the correlation neighborhoods as defined by the grid of FIG. 278.
Figure 27B:
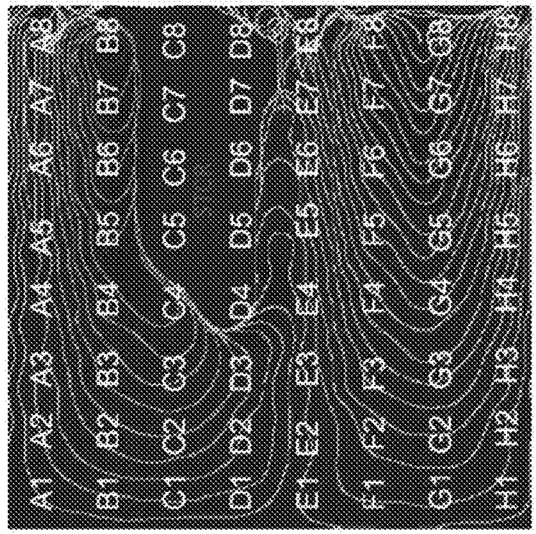
FIG. 27B displays stepwise processing of four correlation neighborhoods of a basket catheter.
Figure 27A:
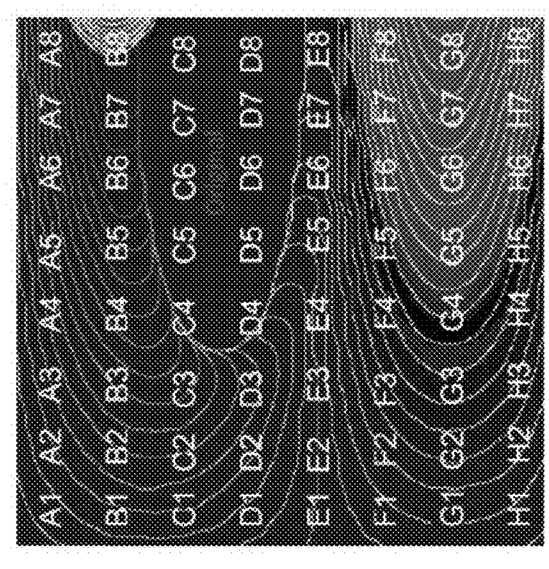
FIG. 27A shows simulation of an excitation wave re-entry circuit in a spherical 3D basket model analyzed using STCR-enhanced EGF methods.

For proof of principle, we tested an STCR-enhanced EGF method on simulated data, as shown in FIGS. 27A through 7C. FIG. 27A shows simulation of an excitation wave re-entry circuit in a spherical 3D basket model analyzed using STCR-enhanced EGF methods. The cycle duration is 141 ins, and the line distance is 3 ins. Each line shape in FIG. 27B displays stepwise processing of four correlation neighborhoods each throughout the 8×8 grid of the basket catheter, while FIG. 27C displays pole projection of the correlation neighborhoods as defined by the inversely extended 10×10 grid in 27B.

In FIG. 27C, a re-entry flow of excitation waves was simulated on a virtual sphere labeled with 64 basket electrodes. Starting at B8 the wave runs around a virtual valve (C4 to D8), goes over the northern pole (or distal portion of the basket catheter—see the upper portion of FIG. 27C), and then back on to the other side (electrodes E, F and G) of a virtual blocking line (situated between the A and H electrodes). The front hits the tail of the wave on the south pole (or the proximal of the basket catheter—see G8B8 in FIG. 27C). The reconstructed STCR picture created from only the 64 electrode signals (FIG. 28C) shows that even though they are highly curved most wavefront shapes are well reconstructed. Also, the distances between the wavefronts (velocities) are very similar between the two pictures in most areas. The biggest discrepancy is observed at the inner curvature of the valve (at C4, D4). The reconstructions of wave nodes (see above) have a resolution of only half an electrode distance because the algorithm always places a wave node in the center between two electrodes. To better visualize individual wavefronts, a 3 ms distance between lines was chosen, while in patients a higher resolution of 1 ms is typically preferred.

2. STCR-Enhanced EGF Applied to Animal Data

Figure 28:
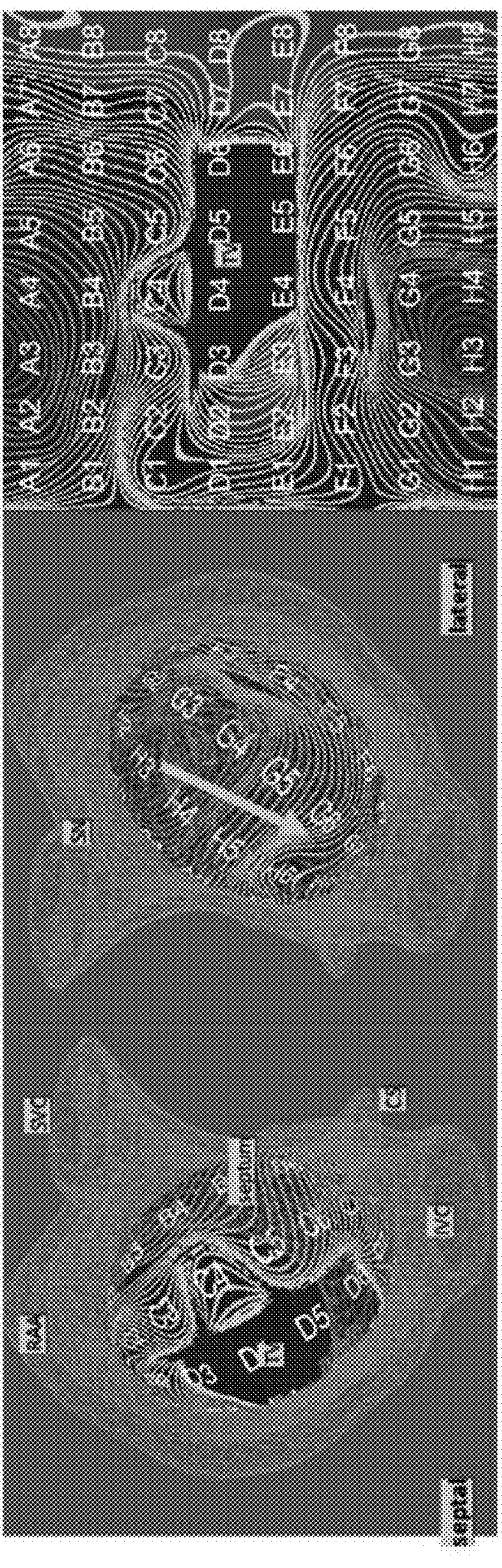
FIG. 28 shows an STCR-enhanced EGF map.
Figure 29:
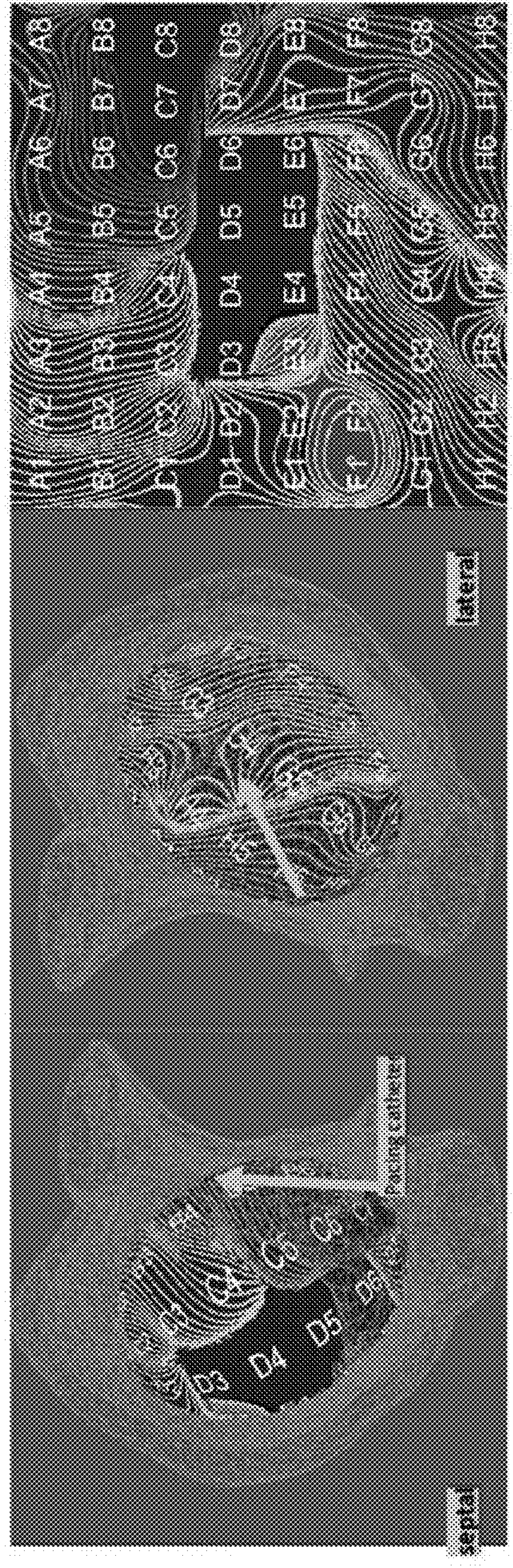
FIG. 29 shows an STCR-enhanced EGF map as in FIG. 28, but with a reversed direction of excitation waves.

Referring now to FIGS. 28 and 29, unipolar recordings from a basket catheter in the right atrium (RA) of a dog in NSR show excitation wave propagation from the SN (H3) downwards (yellow arrow).

FIG. 28 shows an STCR-enhanced EGF map corresponding to an animal right atrium in NSR. On the left side of FIG. 28, there is shown a septal view on a projection of a spherical 3D basket model positioned in a generic right atrial 2D model. Tricuspid valve (TV) shows no signal because no CDVs have been created due to the lack of correlation. In the middle of FIG. 28, there is shown a lateral projection of a source at H3, which is the SN, and where early wavefront lines go from red to yellow downwards in 1 ms steps. On the right side of FIG. 28 there is shown an orthogonal view exhibiting excitation homogenously spreading from the SN in all directions.

When pacing with an ablation catheter at A8 was performed, the direction of propagation reversed. The spherical images show the approximate position of the basket catheter in an atrial 3D model. FIG. 29 shows an STCR-enhanced EGF map as in FIG. 28, but now with a reversed direction of excitation waves due to pacing with an ablation catheter from electrode A8. On the left side of FIG. 29 there is shown a septal view, where excitation moves in an upward direction. The TV again shows no signal. In the middle portion of FIG. 29 there is shown a lateral projection, which also displays an upward direction of the waves. On the right side of FIG. 29 there is shown an orthogonal view that displays the origin of the excitation wave at 08, which is close to the assumed catheter position at A8.

In the same experiment, pacing converted the rhythm into atrial tachycardia (AT). As is evident in FIG. 29, AT is due to a re-entry loop around the superior vena cava (SVC). The tail of the wave (blue) meets the start (red) in a slow conduction zone at H6A5.

Figure 30:
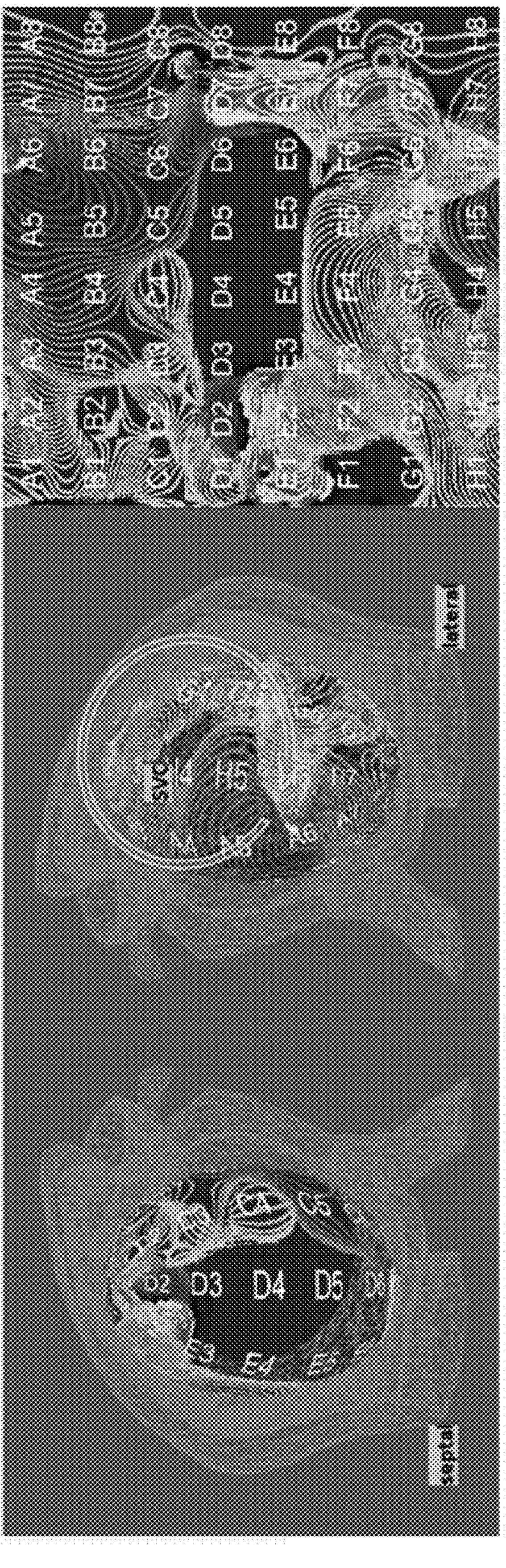

The inlay in FIG. 30 shows a source pattern from HSA-EGF: One rotational source is observed for the excitation circle around H4, while another source appears in a slow conduction velocity zone, where excitation rapidly spreads after having been delayed. FIG. 30 shows an STCR-enhanced EGF map from the same procedure as in FIG. 29, but now intensive pacing has converted the rhythm to AT. In the upper inlay, an HSA map reveals two sources: one circular at GH4 and another at AH6 (see the left panel in FIG. 30). Excitation flows in the same direction on both sides of the TV: Blue to red is from back to front in the displayed septal view. In the middle panel of FIG. 30, lateral projection reveals a circular re-entry around the SVC, with slowest velocity conduction between H6 and A5 where the blue to red transition was placed by defining the color scale. In the right panel of FIG. 30, an orthogonal view shows very dense wavefront lines between H6 and A6.

Figure 31:
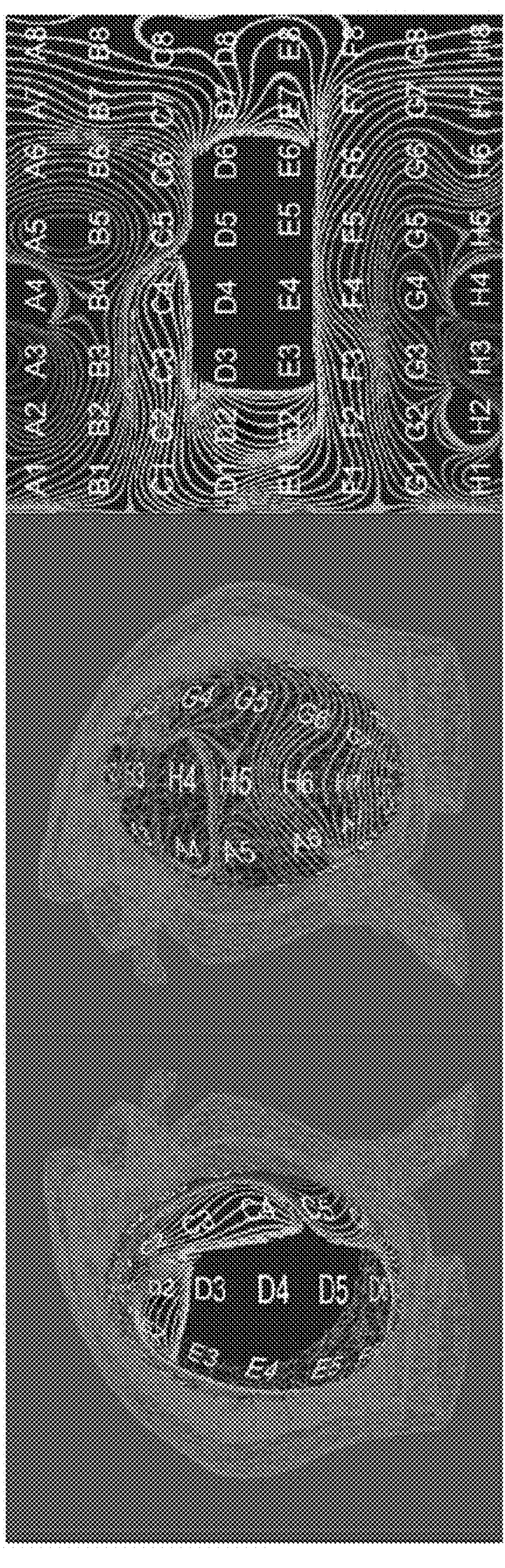
FIG. 31 shows an STCR-enhanced EGF map from the same procedure as in FIG. 30, but with NSR following ablation in the vicinity of A5.

In FIG. 31, subsequent ablation targeting the slow conduction velocity zone around A5 (visible as a source in the HSA-EGF inlay) leads to interruption of the feed-back and causes termination of AT into a NSR (images below). Some irregular conduction likely caused by ablation is now visible (AHB45). FIG. 31 shows an STCR-enhanced EGF map from the same procedure as in FIG. 30, but with NSR following ablation in the vicinity of A5. In the left panel of FIG. 31, a very similar image as in FIG. 28 before AT commenced. In the middle panel of FIG. 31, a lateral projection shows holes in excitation propagation due to ablation. In the right panel of FIG. 31, an orthogonal view shows that the SN is the sole origin of excitation.

Figure 32:
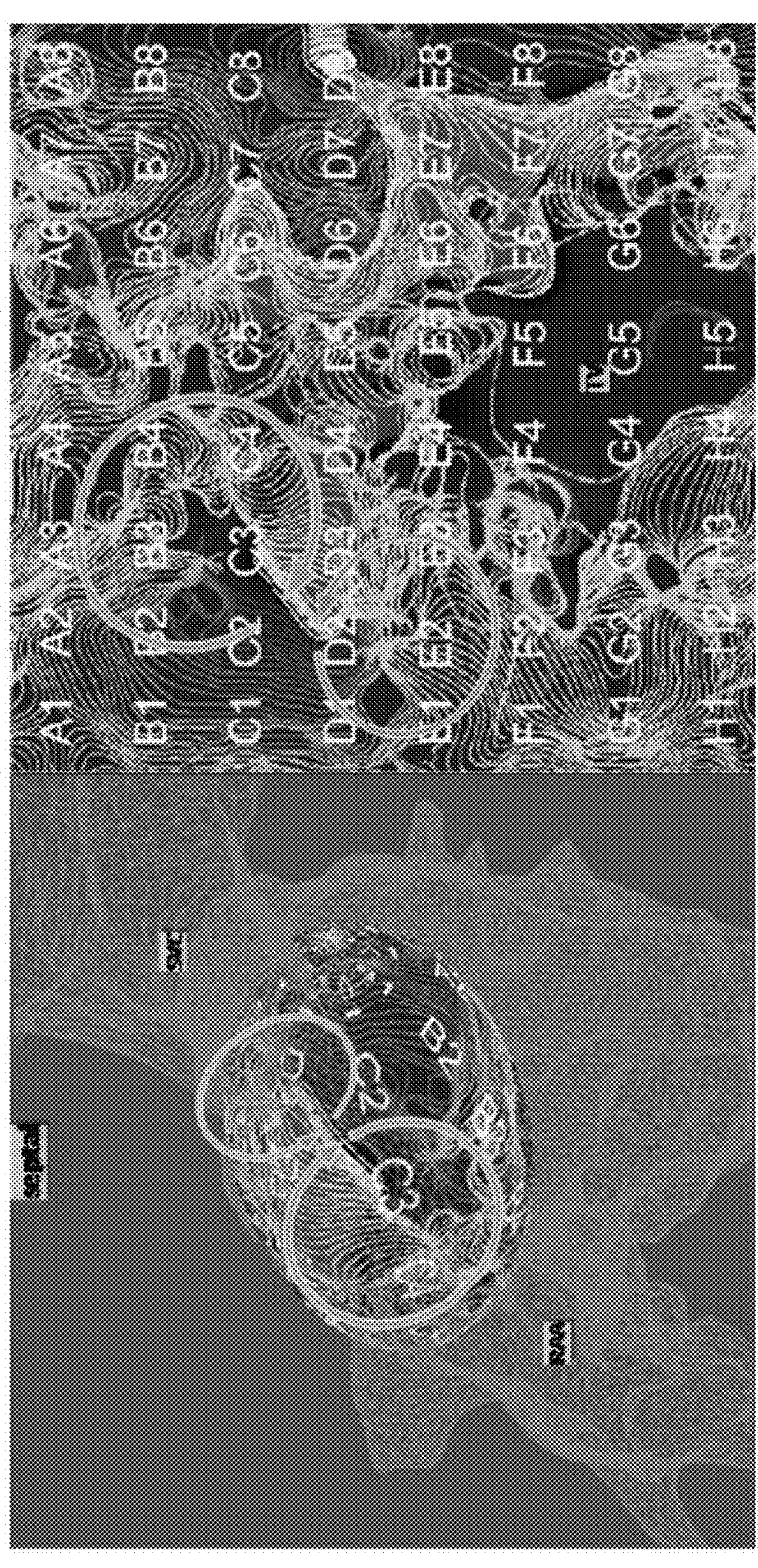
FIG. 32 shows an STCR-enhanced EGF map exhibiting chronic AF.

Referring now to FIG. 32, there is shown an STCR-enhanced EGF map from a similar placement of a basket catheter, but now in the RA of an animal exhibiting chronic AF. The map displays chaotic excitation wave propagation. There is significant variability between individual cycles (not shown in FIG. 32), and overall the map shows slower conduction (note how the lines are close together). The mechanism of AF shown in FIG. 32 indicates a twofold re-entry circle (or figure-of-eight) around the SVC and the RAA. The orthogonal view shown in FIG. 32 shows two singularities near C3 and E2.

3. STCR Applied to Patient Data Exhibiting NSR—Correlation with a Voltage Map

Figure 33:
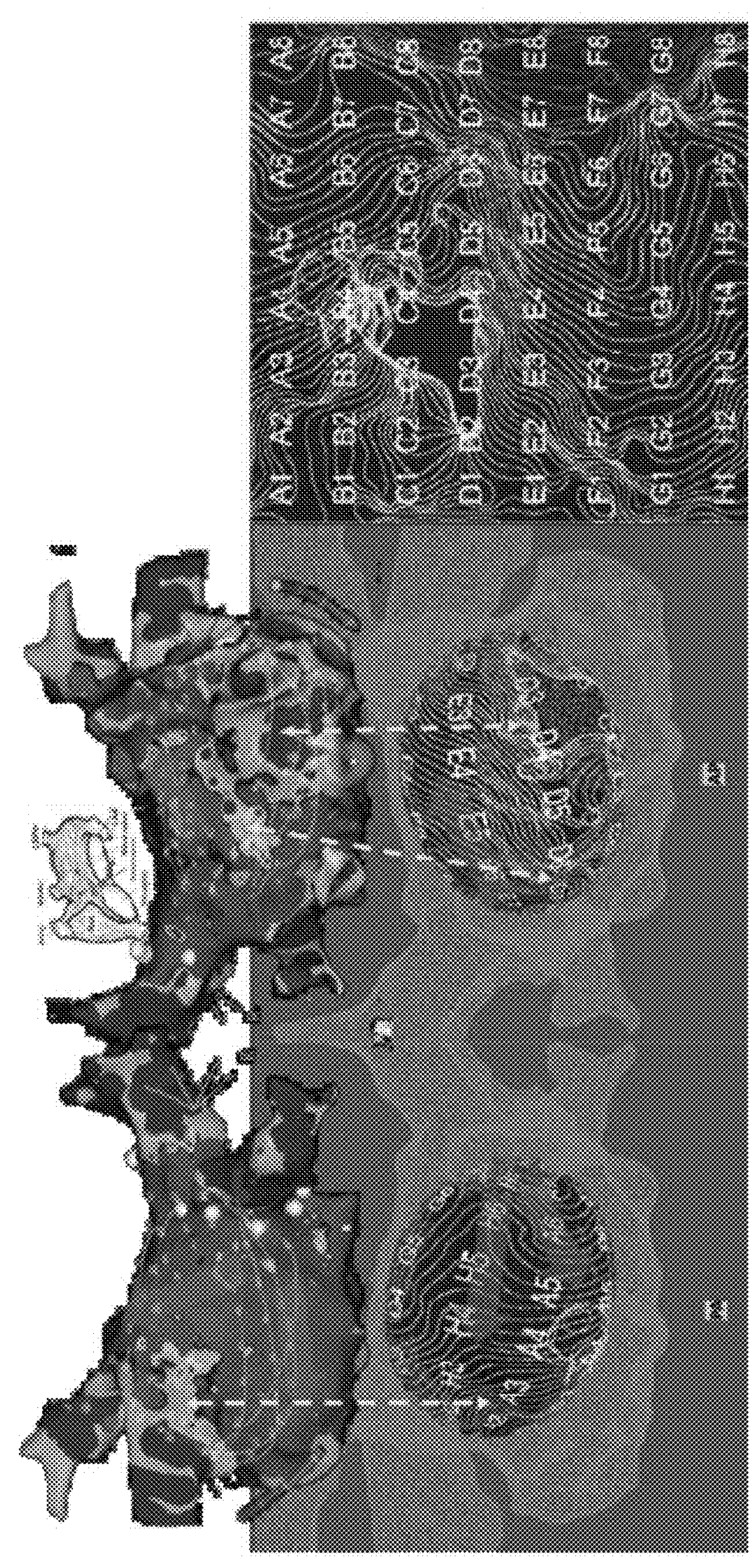
FIG. 33 shows unipolar recordings from a basket catheter in the left atrium of a patient in NSR.

Referring now to FIG. 33, there are shown unipolar recordings from a basket catheter in the left atrium of a patient in NSR, which displays excitation wave propagation from the Bachmann's bundle (EB) leftwards. In FIG. 33, STCR enhanced EGF maps are compared with voltage maps. Low voltage areas (green and red) are congruent with slow conduction (narrow lines in STCR image). In FIG. 33, there is shown a map corresponding to the left atrium (LA) of a patient in NSR. Velocity lines are significantly narrower in the area of the D and E electrodes, where a Carto voltage map shows red and green regions of low voltage in the areas of the A, H and G electrodes (purple in Carto). G8 is the origin of excitation in accordance with the position of Bachmann's bundle in the LA wall.

The advantage of detecting putative fibrotic areas with STCR-enhanced EGF is two-fold. Slow conduction may be a more valuable parameter than low voltage since it represents a known mechanism of arrhythmias, which can enable the generation of feedback loops occurring in the atrium because of the corresponding shorter wavelength of the excitation waves. STCR-enhanced EGF maps can also be created with a single recording in only a minute or less, while voltage maps require a sequential positioning of a catheter at multiple positions, a process requiring 20 minutes or longer.

Most patients being treated for paroxysmal AF and many persistent AF patients are arriving for treatment in NSR which up to now has been a good condition in which to perform standard PVI without inducing AF. Up to now, sources of AF, if they are located outside the PVs, could not been detected under NSR and this required induction of AF. The fact that STCR-enhanced EGF maps can reveal slow conduction zones (which are often associated with sources), even in NSR, strongly suggests that STCR-enhanced EGF maps may serve for diagnostic purposes in AF patients, even without the inducement of AF. This may further simplify AF procedures for persistent patients and may offer the chance to check for substrate related sources during an initial procedure (where up to now only PVI is performed).

4. STCR-Enhanced EGF Applied to Patient Data Exhibiting AT and AFL

STCR-enhanced EGF mapping is well adapted to detect rapid atrial arrhythmias like AT and AFL, which are generally characterized by a fixed ratio between atrial and ventricular beats, and where individual cycles are very similar to each other. Such arrhythmias are traditionally analyzed by characterizing their circular excitation flow pathways using activation mapping, where a catheter is moved along the pathway while measuring the local time of activation (LAT) point by point each time on a different beat. Like voltage mapping, this is a relatively demanding and slow process, which can be replaced by STCR-enhanced EGF and provide a panoramic approach that requires only one to three recordings with a basket catheter. Another alternative, which is also time rather time consuming, however, is the detection of the slow conducting critical isthmus by entrainment mapping.

Figure 34:
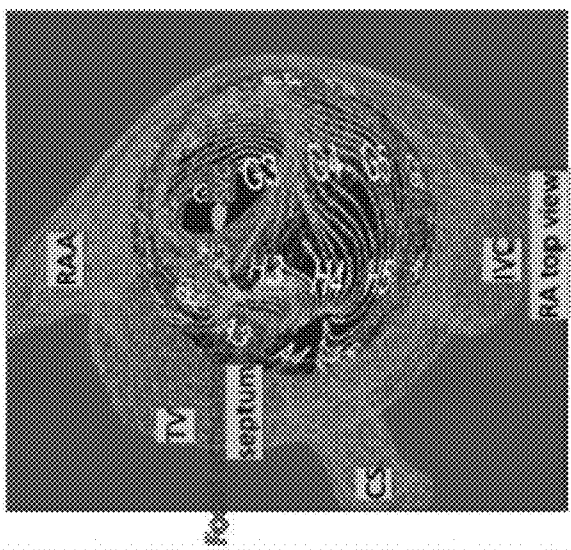
FIG. 34 shows results from unipolar recordings using a basket catheter in the LA of a patient in AFL.
Figure 34:
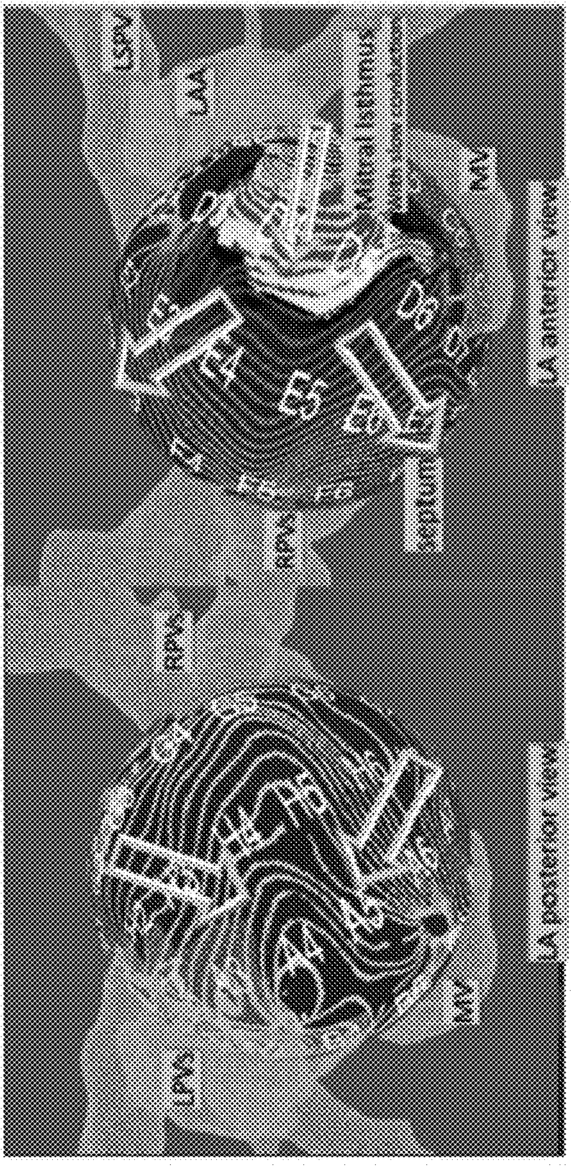

FIG. 34 shows results from unipolar recordings using a basket catheter in the LA of a patient in AFL. In FIG. 34, excitation wave propagation occurs in an obvious re-entry loop. The STCR enhanced EGF maps shows that slow conduction appears in the Mitral Isthmus, an ideal ablation target. A subsequent is recording in the RA shows that activation now comes from the left side and is appearing in the septum.

Continuing to refer to FIG. 34, there are maps from the LA and RA of a patient in AFL. In the left panel of FIG. 35, velocity lines are distant, indicating fast conduction on the posterior wall. In the middle panel of FIG. 34, lines are significantly narrower in the anterior view, in particular in the mitral isthmus area. A circular excitation flow pathway is evident (blue to red). In the right panel of FIG. 35, in the RA excitation begins at the septum (focal activation from the left) and spreads over the atrium without any indication of re-entry.

Mapping of AFL and AT with STCR-enhanced EGF has the two advantages already identified compared to the voltage mapping: (i) Identification of circular excitation flow pathways including slow conduction zones potentially serving as ablation target, and (ii) A single shot approach is at least 20 times faster than traditional LAT mapping.

A main application of STCR-enhanced EGF in standard HSA-based EGF procedures is that EGF guided ablation converts AF into AT or AFL. This is the case by a large percentage up to 30%, depending on the patient group. In this case the procedure can directly switch to the treatment of the tachycardia without changing any equipment. The same is true in patients known for variability of their arrhythmia between AF and AT, which advantageously may now both be addressed by one and the same set-up and equipment.

5. STCR Applied to Patient Data Exhibiting AF

AF patients who are showing recurrence after an initial PVI procedure can be successfully treated with HSA-based EGF guided ablation identifying the relevant sources in the atrial tissue (FLOW-AF study, NCT04473963). The exact mechanism of a source identified with this technology is not revealed by this procedure. In many cases this may be rather irrelevant for the doctor because ablation of the myocardial tissue at the exact location of the source works to eliminate the source, which has then disappeared on a subsequent recording.

In some patients, however, the mechanism matters because a re-entry pathway not destroyed completely by the ablation leads to the source escaping the effects of ablation. This sometimes ends up in time-consuming source hunting associated with a rather invasive series of ablations. Unfortunately, it is currently not easily possible to identify this subpopulation of patients in advance before an ablation procedure has been initiated so as to optimize ablation strategy in the first place (which suggests a medical need for a method providing an initial identification of the mechanism).

Figure 35:
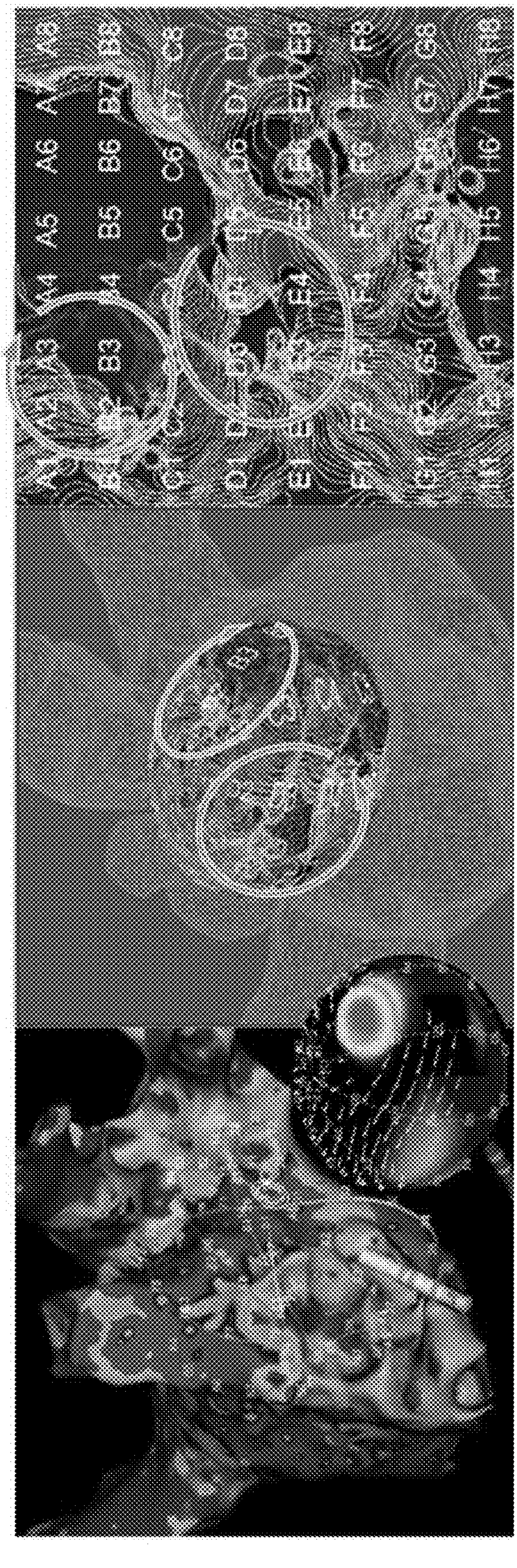
FIG. 35 shows
Figure 36:
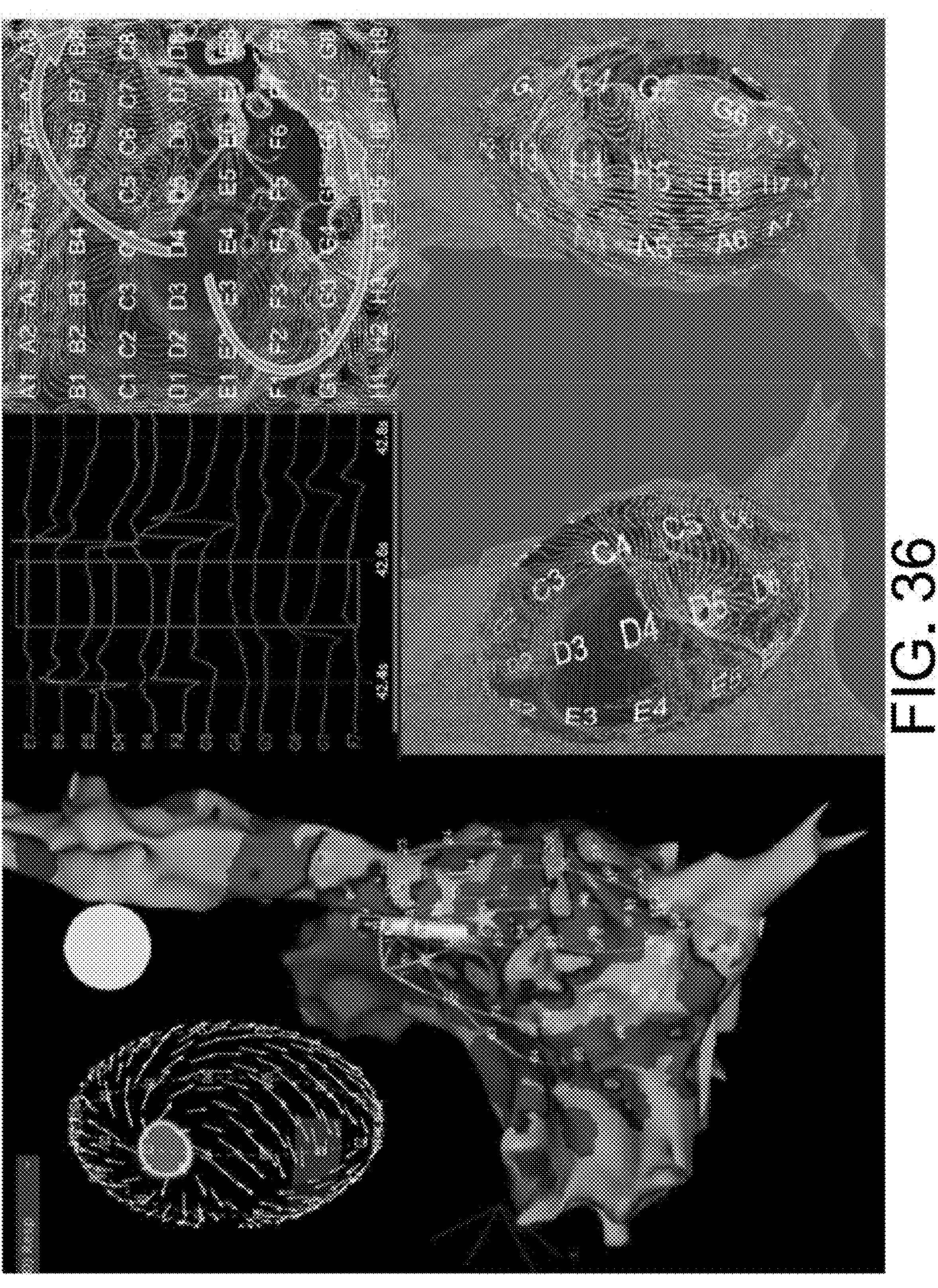
FIG. 36 shows the LA of a patient in AF with excitation wave propagation in a double re-entry loop around LAA and LPVs.
Figure 37:
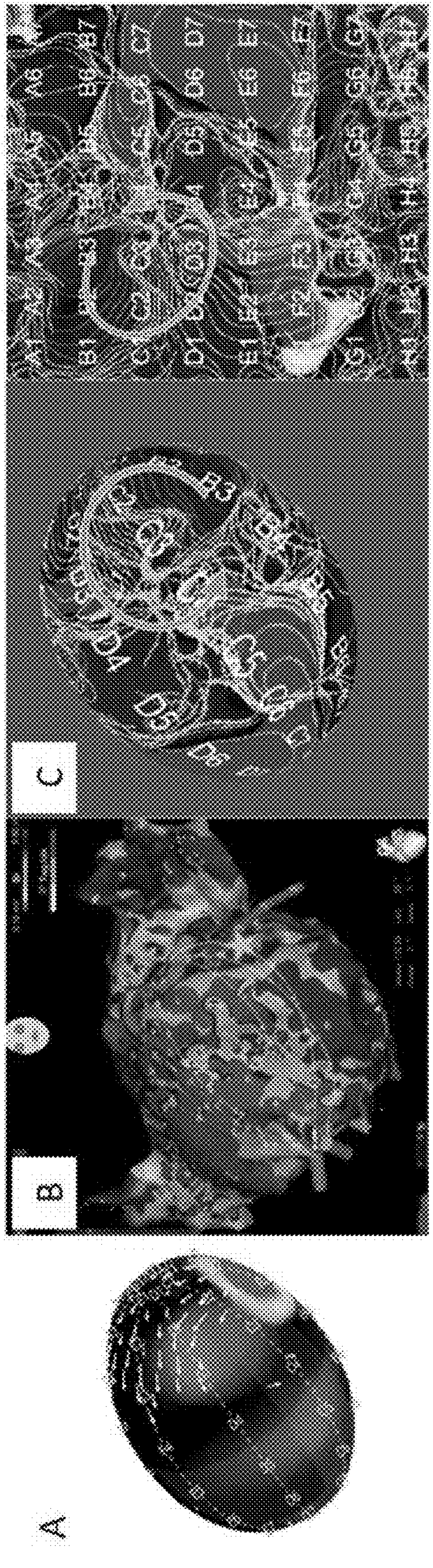
FIG. 37 shows a unipolar recording from a basket catheter in the left atrium of another patient exhibiting AF.

FIGS. 35, 36 and 37 show STCR enhanced EGF maps from three different AF patients exhibiting sources belonging to three different mechanistic subtypes.

FIG. 35 shows the left atrium (LA) of a patient in AF with excitation wave propagation in a double re-entry loop around LAA and LPVs, suggesting that the isthmus (C4) between the LPVs LAA and the mitral valve (MV) should be targeted (which is not obvious from the source spot BC23 originally identified being more in the center of the active rotor). In FIG. 35, enhanced EGF maps from the LA of the patient in AF are shown. In the left panel of FIG. 35, the HSA-EGF map indicates a rotational source at BC23. The corresponding voltage map shows that this area belongs to the LPVs, which are isolated. In the middle panel of FIG. 35, the STCR-EGF map indicates two rotational re-entries around LPVs and LAA. In the right panel of FIG. 35, both circles pass the isthmus at C4 between the LAA, LPVs and the MV.

Referring now to FIG. 36, there are shown unipolar recordings from the RA of another patient exhibiting AF, where excitation wave propagation from a focal source in the posterior wall at DE4 is displayed, and which represents a typical ablation target that can be addressed directly by point ablation. In FIG. 37, the left panel shows an HSA-EGF map indicating a source at E3. The corresponding voltage map shows that this area has some low voltage spots. In the middle panel of FIG. 36, the STCR-EGF map indicates a focal source originating excitation at D4. Excitation wavefronts travel from the source in both directions around the TV but do not circle back. The electrograms show a pause (see the blue square in the upper left of FIG. 36) before the next cycle starts. Typical source potentials are shown at D4 and E4. The right panel of FIG. 36 shows an anterior voltage map.

FIG. 37 shows a unipolar recording from a basket catheter in the left atrium of yet another patient exhibiting AF. The STCR map displays the excitation wave propagation from B3, but with a re-entry loop conducting the excitation back (see arrow) to a slow velocity conduction zone and re-entering 83 from C4. In such cases, HSA-based EGF identifies the source at the location where the excitation wave is divergent and spreads again encountering the isthmus in the slow velocity conduction area. The area of divergence may not be the ideal point of ablation, rather than the slow conduction zone itself, which is situated a bit offset to the location of the HSA-based EGF identified source. Ablation of a larger area around the source would certainly be successful in most cases, but a more focused targeting of the slow conduction velocity zone might be reasonable in terms of a providing a minimally invasive therapy. Continuing to refer to FIG. 37, panel A is an HSA-EGF map indicating a source at B3. In panel B of FIG. 38, a voltage map shows that this area is at the border between low and high voltage. Panel C of FIG. is an STCR-EGF map displaying a focal re-entry source with a slow conduction zone CD4. Behind the slow conduction area (shown in blue), excitation spreads from 83.

Note that the various embodiments of reconstructed EP mapping signal methods and techniques described and disclosed herein are not intended to be limited to SCTR methods and techniques, but may be carried out to reconstruct EP mapping signals at increased resolution using one or more of the following image reconstruction methods or techniques, alone or in combination: (a) spatio-temporal constraint reconstruction (STCR) methods or techniques; (b) Bayesian or extended Bayesian back-filtered projection methods or techniques; (c) machine learning methods or techniques; (d) deep learning or cascaded deep learning methods or techniques; (e) domain-transform manifold learning methods or techniques; (f) neural network methods or techniques; (g) convolutional neural network methods or techniques; (h) deep generative adversarial network methods or techniques; (i) dual domain cascading U-net methods or techniques; and/or (j) de-aliasing network methods or techniques.

EGF, in combination with STCR and other image reconstruction techniques enumerated and described herein, may also be used to map ventricular arrhythmias. EGF, in combination with STCR and other image reconstruction techniques enumerated and described herein, may also be used to map portions of the brain, stomach, spine, spinal cord, nerves, and other organs exhibiting electrical activity in the human body or in animals.

In view of the structural and functional descriptions provided herein, those skilled in the art will appreciate that portions of the described devices and methods may be configured as methods, data processing systems, or computer methods. Accordingly, these portions of the devices and methods described herein may take the form of a hardware embodiment, a software embodiment, or an embodiment combining software and hardware, such as shown and described with respect to computer system 300 illustrated in FIG. 18. Furthermore, portions of the devices and methods described herein may be a computer method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer methods. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 1B:
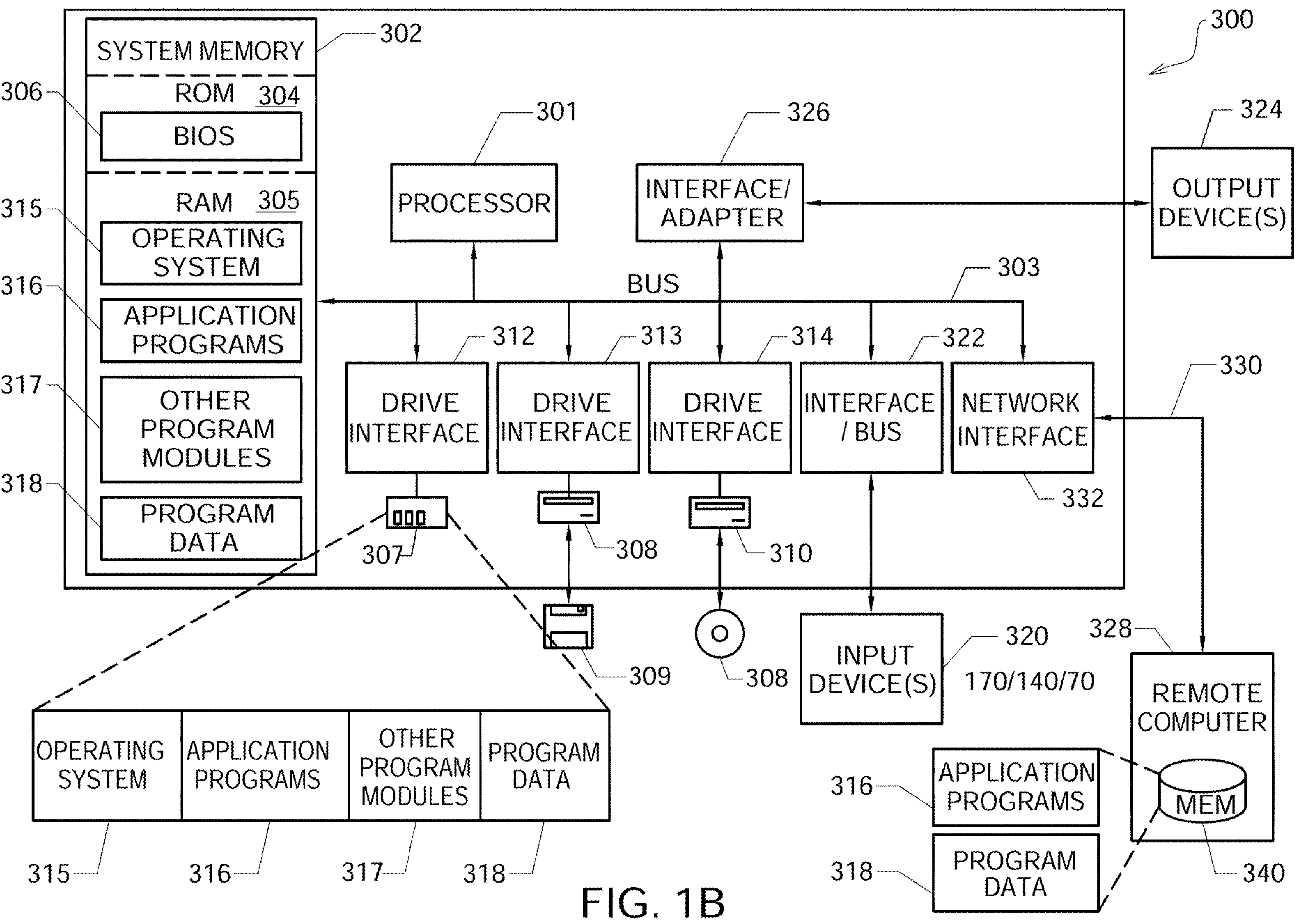
FIG. 1B shows one embodiment of a computer system 300.

In this regard, FIG. 1B illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of the systems, devices, components and methods described and disclosed herein fall within the scope of the various embodiments. Those skilled in the art should appreciate that they may readily use the present disclosure as a basis for designing or modifying other processes and structures for carrying out the same purposes and/or achieving the same advantages of the embodiments introduced herein, Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

We claim:

1. A system configured to detect at least one location of: (a) at least one intracardiac source or rotational phenomenon; and (b) at least one intracardiac zone or area of slow electrical conduction velocity, such source, phenomenon, zone or area being associated with at least one cardiac rhythm disorder in a patient's heart, the system comprising:

(a) at least one computing device;

(b) at least one data acquisition device operably connected to the at least one computing device or configured to provide as outputs therefrom at least one of intracardiac electrophysiological EP mapping signals and/or body surface electrophysiological EP mapping signals (EP mapping signals);

(c) a display or monitor operably connected to the at least one computing device and configured to visually display to the user one or more maps generated by the at least one computing device;

wherein the computing device comprises at least one non-transitory computer readable medium configured to store instructions executable by at least one processor to determine the at least one location of the at least one source, rotational phenomenon, and/or zone of slow electrical conduction, associated with the at least one cardiac rhythm disorder in the patient's heart, the computing device being configured to: (i) receive the EP mapping signals from at least one of a plurality of intracardiac electrodes located inside the patient's heart and/or the body surface electrodes located on the surface of the patient's body (electrodes), the electrodes having spatial 2D and/or 3D positions on or in the patient's body associated therewith; (ii) preprocess the EP mapping signals; (iii) analyze the preprocessed EP mapping signals and determining reconstruction constraint parameters to apply thereto; (iv) apply the reconstruction constraint parameters to the EP mapping data and generating, using one or more correlation matrices, reconstructed EP mapping signals having spatial positions associated therewith and located between, or not at the same locations as, the spatial positions of the electrodes; (v) assign or relate positional data corresponding to spatial positions of: (a) the electrodes and their associated EP mapping signals, and (b) the reconstructed EP mapping signals; (vi) generate at least one spatial map of the electrode positions and the positions of the reconstructed EP mapping signals; (vii) for each or selected discrete times over which the EP mapping signals and the reconstructed EP mapping signals are being processed, process the EP mapping signals and the reconstructed EP mapping signals to generate a plurality of surfaces or data grids, each such surface or data grid corresponding at least partially to the at least one spatial map, at least one surface or data grid being generated for each such time, and (viii) using a multi-frame Horn-Schunck algorithm to process the plurality of surfaces or data grids through time to generate at least one enhanced resolution map corresponding at least partially to the spatial map, the at least one enhanced resolution map being configured to reveal the at least one location of the at least one source or rotational phenomenon or at least one zone or area of slow electrical conduction velocity associated with the at least one cardiac rhythm disorder, the at least one enhanced resolution map being shown to the user on the display or monitor.

2. The system of claim 1, wherein analyzing and determining the constraint reconstruction parameters to apply to the EP mapping signals is further based upon the shapes and velocities of the EP mapping signals.

3. The system of claim 1, wherein preprocessing of the EP mapping signals comprises generating at least one histogram of all R-peak intervals and determining the width(s) thereof.

4. The system of claim 3, further comprising subtracting averaged R-peak traces from all traces of the EP mapping signals.

5. The system of claim 4, further comprising detecting F-wave peaks in the EP mapping signals.

6. The system of claim 5, further comprising determining average intervals between R-peaks and F-waves before determining constraint reconstruction parameters.

7. The system of claim 1, wherein the intracardiac electrodes are mounted on or form a portion of a basket catheter.

8. The system of claim 7, wherein the basket catheter has between 32 and 64 electrodes.

9. The system of claim 1, wherein the surfaces or data grids are generated by the computing device using Green's function.

10. The system of claim 1, wherein the map generated by the computing device is configured to reveal a location in the patient's heart of one or more of: (a) an active rotor; (b) a passive rotor; (c) a breakthrough point, (d) a focal point, and (e) a slow electrical conduction velocity zone or area.

11. The system of claim 1, wherein the reconstructed EP mapping signals are generated using one or more of the following image reconstruction methods or techniques, alone or in combination: (a) spatio-temporal constraint reconstruction (STCR) methods or techniques; (b) Bayesian or extended Bayesian back-filtered projection methods or techniques; (c) machine learning methods or techniques; (d) deep learning or cascaded deep learning methods or techniques; (e) domain-transform manifold learning methods or techniques; (f) neural network methods or techniques; (g) convolutional neural network methods or techniques; (h) deep generative adversarial network methods or techniques; (i) dual domain cascading U-net methods or techniques; and/or (j) de-aliasing network methods or techniques.

12. The system of claim 1, wherein the at least one enhanced resolution map represents between 64 and 1,024 combined spatial positions of the electrodes and the reconstructed EP mapping signals.

13. The system of claim 1, wherein the enhanced resolution map comprises or displays optimized intensity points (EDFs).

14. A method of detecting at least one location of at least one intracardiac source or rotational phenomenon and/or at least one intracardiac zone or area of slow electrical conduction velocity, such source, phenomenon, zone or area being associated with at least one cardiac rhythm disorder in a patient's heart, the system comprising at least one computing device, at least one data acquisition device operably connected to the at least one computing device or configured to provide as outputs therefrom at least one of intracardiac electrophysiological EP mapping signals and/or body surface electrophysiological EP mapping signals (EP mapping signals), a display or monitor operably connected to the at least one computing device and configured to visually display to the user one or more maps generated by the at least one computing device, wherein the computing device comprises at least one non-transitory computer readable medium configured to store instructions executable by at least one processor to determine the at least one location of the at least one source, rotational phenomenon, and zone of slow electrical conduction associated with the at least one cardiac rhythm disorder in the patient's heart, the computing device being configured to: (i) receive the EP mapping signals from at least one of a plurality of intracardiac electrodes located inside the patient's heart and/or the body surface electrodes located on the surface of the patient's body (electrodes), the electrodes having spatial 2D and/or 3D positions on or in the patient's body associated therewith; (ii) preprocess the EP mapping signals; (iii) analyze the preprocessed EP mapping signals and determining reconstruction constraint parameters to apply thereto; (iv) apply the reconstruction constraint parameters to the EP mapping data and generate, using one or more correlation matrices, reconstructed EP mapping signals having spatial positions associated therewith and located between, or not at the same locations as, the spatial positions of the electrodes; (v) assign or relate positional data corresponding to spatial positions of: (a) the electrodes and their associated EP mapping signals, and (b) the reconstructed EP mapping signals; (vi) generate at least one spatial map of the electrode positions and the positions of the reconstructed EP mapping signals; (vii) for each or selected discrete times over which the EP mapping signals and the reconstructed EP mapping signals are being processed, process the EP mapping signals and the reconstructed EP mapping signals to generate a plurality of surfaces or data grids, each such surface or data grid corresponding at least partially to the at least one spatial map, at least one surface or data grid being generated for each such time, and (viii) using a multi-frame Horn-Schunck algorithm to process the plurality of surfaces or data grids through time to generate at least one enhanced resolution map corresponding at least partially to the spatial map, the at least one enhanced resolution map being configured to reveal the at least one location of the at least one source or rotational phenomenon or at least one zone or area of slow electrical conduction velocity associated with the at least one cardiac rhythm disorder, the at least one enhanced resolution map being shown to the user on the display or monitor, the method comprising:

(a) acquiring, using the data acquisition device, the EP mapping signals;

(b) using the computing device, assigning positions or identifiers for the electrodes and the reconstructed EP mapping signals;

(d) using the computing device and the assigned positions or identifiers, providing or generating a spatial map of the intracardiac electrode and reconstructed EP mapping signal positions;

(e) using the computing device, for each or selected discrete times over which the EP mapping signals are being processed, processing the EP mapping signals to generate a plurality of surfaces or data grids corresponding at least partially to the spatial map, one surface or data grid being generated for each such time, and (f) using the computing device to process the plurality of surfaces or data grids through time to generate an enhanced resolution map corresponding at least partially to the spatial map, the enhanced resolution map being configured to reveal on the monitor or display to a user the at least one location of the at least one source, phenomenon, zone or area associated with the at least one cardiac rhythm disorder.

15. The method of claim 14, further comprising using at least one of the computing device and the data acquisition device, at least one of conditioning, filtering, normalizing and adjusting the amplitudes of at least one of the acquired EP mapping signals.

16. The method of claim 14, further comprising generating the surfaces or data grids using Green's function.

17. The method of claim 14, wherein analyzing and determining the constraint reconstruction parameters to apply to the EP mapping signals is further based upon the shapes and velocities of the EP mapping signals.

18. The method of claim 14, wherein preprocessing of the EP mapping signals comprises generating at least one histogram of all R-peak intervals and determining the width(s) thereof.

19. The method of claim 18, further comprising subtracting averaged R-peak traces from all traces of the EP mapping signals.

20. The method of claim 19, further comprising detecting F-wave peaks in the EP mapping signals.

21. The method of claim 20, further comprising determining average intervals between R-peaks and F-waves before determining constraint reconstruction parameters.

22. The method of claim 14, wherein the intracardiac electrodes are mounted on or form a portion of a basket catheter.

23. The method of claim 22, wherein the basket catheter has between 32 and 64 electrodes.

24. The method of claim 14, wherein the enhanced resolution map generated by the computing device is configured to reveal a location in the patient's heart of one or more of: (a) an active rotor; (b) a passive rotor; (c) a breakthrough point, (d) a focal point, and (e) a slow electrical conduction velocity zone or area.

25. The method of claim 14, wherein the reconstructed EP mapping signals are generated using one or more of the following image reconstruction methods or techniques, alone or in combination: (a) spatio-temporal constraint reconstruction (STCR) methods or techniques; (b) Bayesian or extended Bayesian back-filtered projection methods or techniques; (c) machine learning methods or techniques; (d) deep learning or cascaded deep learning methods or techniques; (e) domain-transform manifold learning methods or techniques; (f) neural network methods or techniques; (g) convolutional neural network methods or techniques; (h) deep generative adversarial network methods or techniques; (i) dual domain cascading U-net methods or techniques; and/or (j) de-aliasing network methods or techniques.

26. The method of claim 14, wherein the at least one enhanced resolution map represents between 64 and 1,024 combined spatial positions of the electrodes and the reconstructed EP mapping signals.

27. The method of claim 14, wherein the enhanced resolution map comprises or displays optimized intensity points (EDFs).

* * * * *